United States Patent
Szyf et al.

(10) Patent No.: US 7,098,012 B1
(45) Date of Patent: Aug. 29, 2006

(54) DNA DEMETHYLASE, THERAPEUTIC AND DIAGNOSTIC USES THEREOF

(75) Inventors: Moshe Szyf, Côte St-Luc (CA); Sanjoy Bhattacharya, Montréal (CA); Shyam Ramchandani, Niagara Falls (CA)

(73) Assignee: McGill University, Montreal (CA)

( * ) Notice: Subject to any disclaimer, the term of this patent is extended or adjusted under 35 U.S.C. 154(b) by 0 days.

(21) Appl. No.: 09/554,414

(22) PCT Filed: Nov. 12, 1998

(86) PCT No.: PCT/CA98/01059

§ 371 (c)(1),
(2), (4) Date: Sep. 6, 2000

(87) PCT Pub. No.: WO99/24583

PCT Pub. Date: May 20, 1999

(30) Foreign Application Priority Data

Nov. 12, 1997 (CA) .................................. 2220805
May 11, 1998 (CA) .................................. 2230991

(51) Int. Cl.
*C12N 9/10* (2006.01)
*C12Q 1/48* (2006.01)
*C12Q 1/68* (2006.01)
*G01N 35/53* (2006.01)
*G01N 33/567* (2006.01)

(52) U.S. Cl. ............................ 435/193; 435/15; 435/6; 435/7.1; 435/7.21; 435/7.23

(58) Field of Classification Search ................ 435/193, 435/69.2, 15, 6, 7.1, 7.21, 7.23; 536/23.5, 536/23.2, 23.1, 24.5; 514/24; 424/147.1
See application file for complete search history.

(56) References Cited

OTHER PUBLICATIONS

Seppa N. Gene therapy for sickle-cell disease? Science News 2001, 160, 372.*
Weatherall D. J. et al. Inherited haemoglobin disorders: an increased global health problem, Bull. World Health Org. 2001, 78, 704.*
Hendrich B. et al. Identification and characterization of a family of mammalian methyl-CpG binding proteins, Mol. Cell. Bioll. 1998, 18, 6548-6547.*
Database GeneBank Accession No. AF72242, Oct. 28, 1998.*
Lewis J. D. et al. Purification, sequence, and cellular localization of a novel chromosomal protein that binds to methylated DNA, Cell, 1992, 69, 905-914.*
Szyf M. et al. Ras induces a general DNA demethylation activity in mouse embrional P19 cells, J. Biol. Chem. 1995, 270, 12690-12696.*

* cited by examiner

*Primary Examiner*—Rebecca E. Prouty
*Assistant Examiner*—Malgorzata A. Walicka
(74) *Attorney, Agent, or Firm*—Crowell & Moring LLP

(57) ABSTRACT

The present invention relates to a DNA demethylase enzyme having about 40 KDa, and wherein said DNA demethylase enzyme is overexpressed in cancer cells and not in normal cells. The present invention also relates to the therapeutic and diagnostic uses of the DNA demethylase.

6 Claims, 50 Drawing Sheets

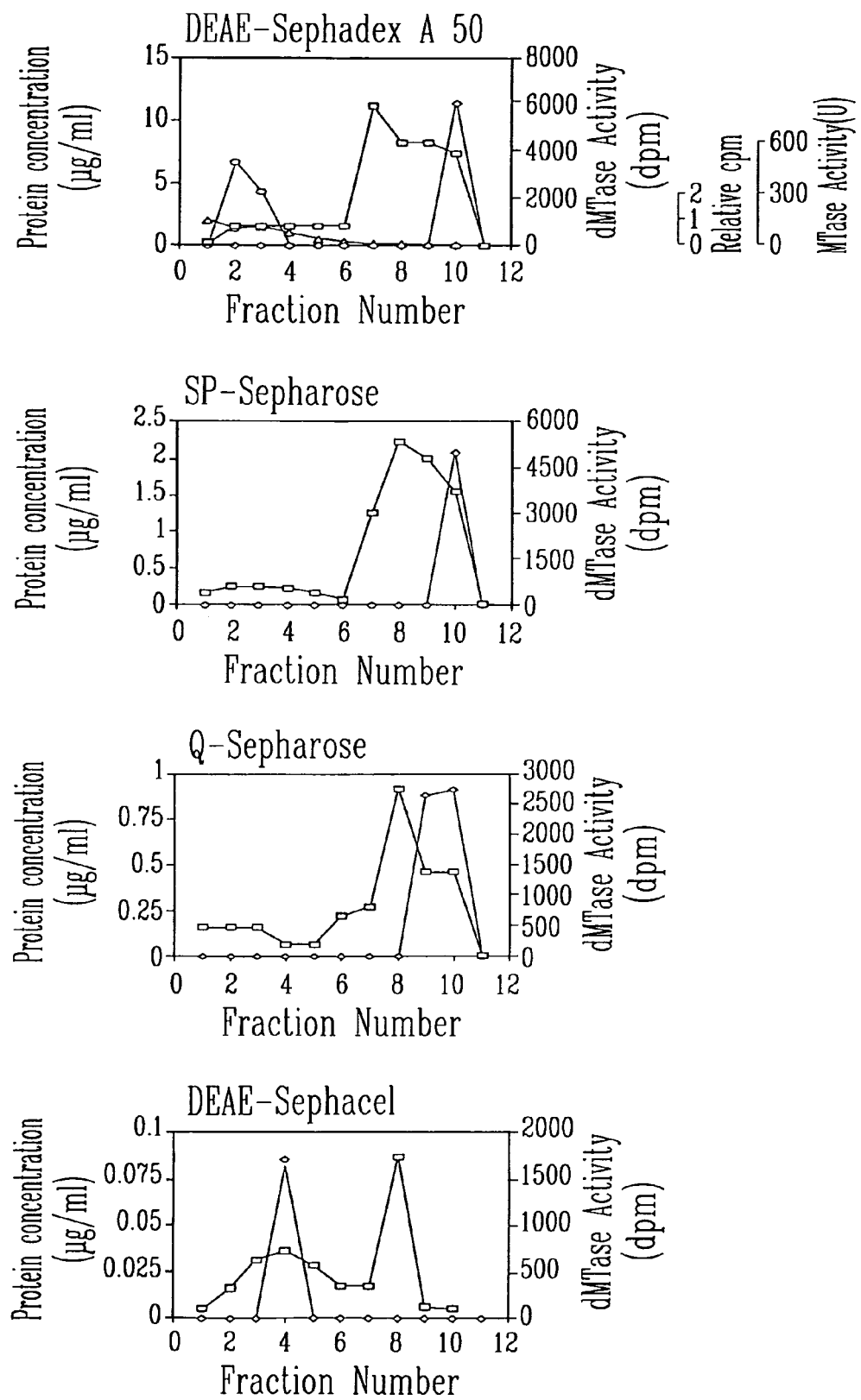
FIG_1B

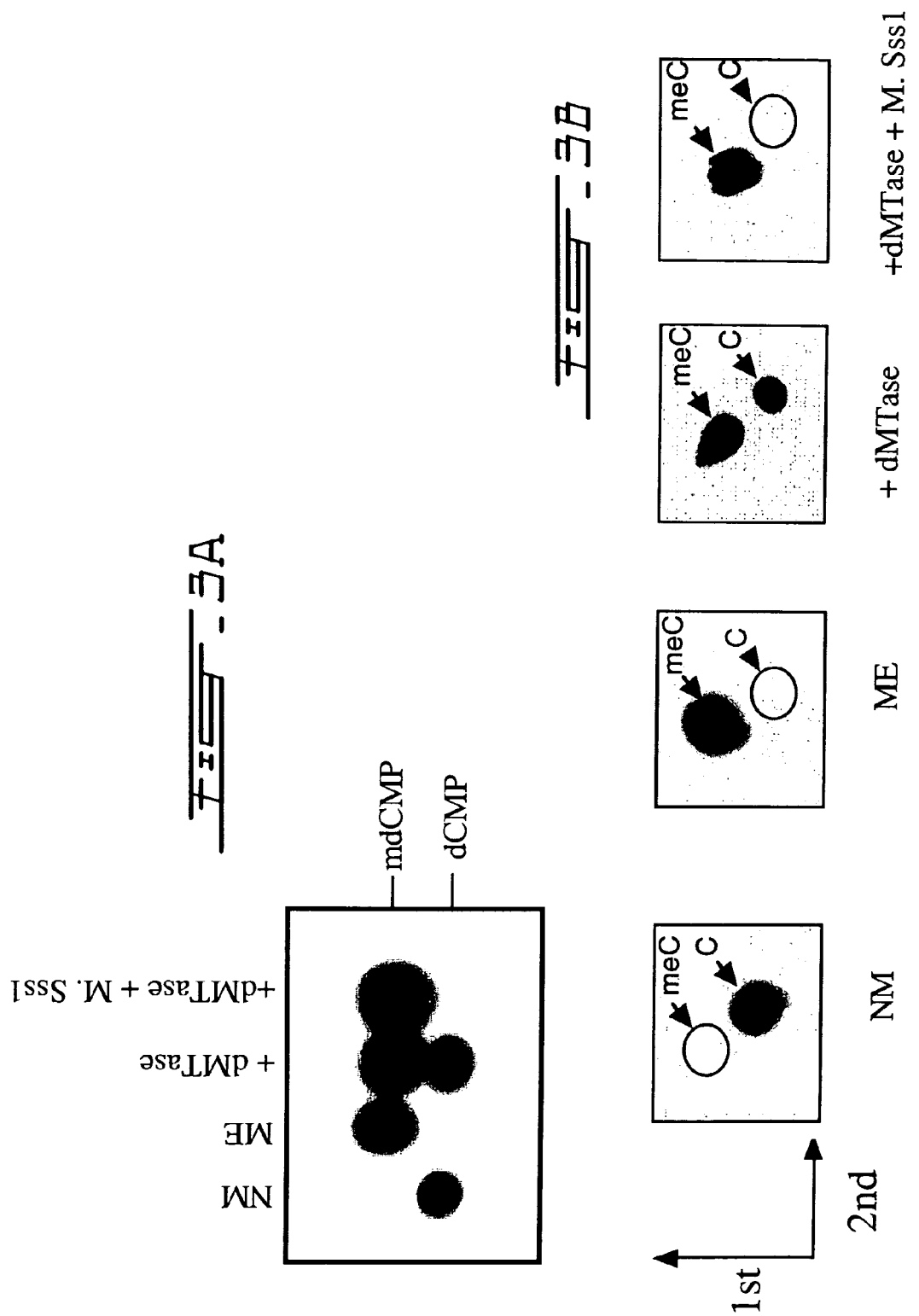

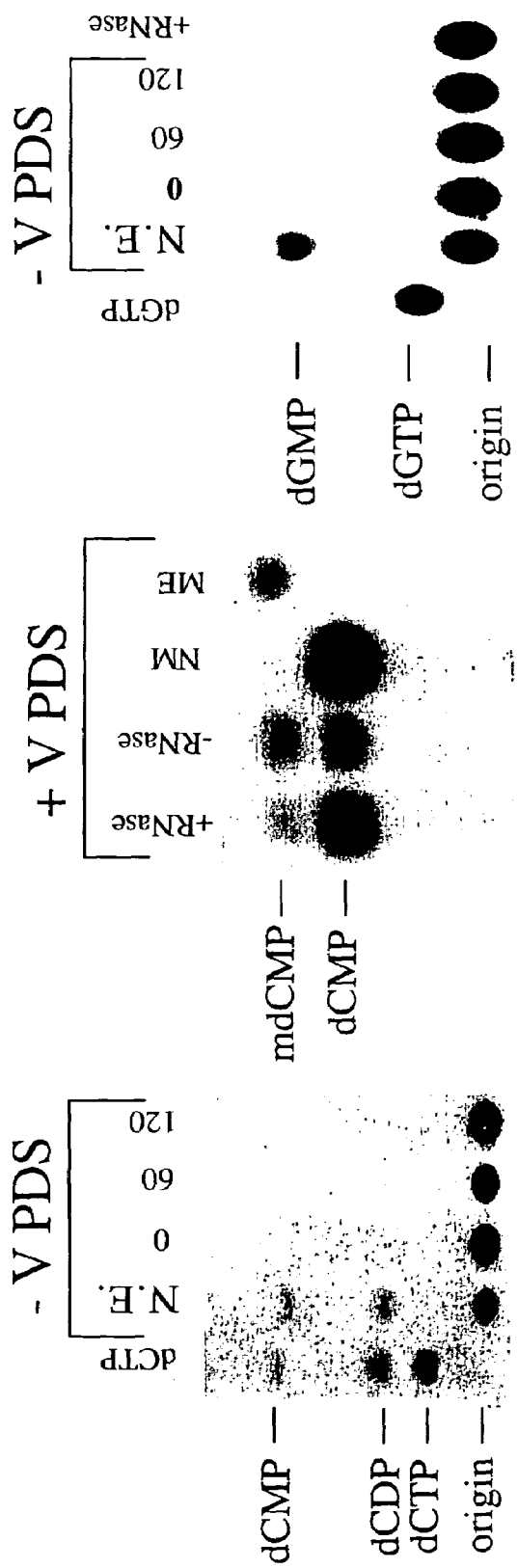

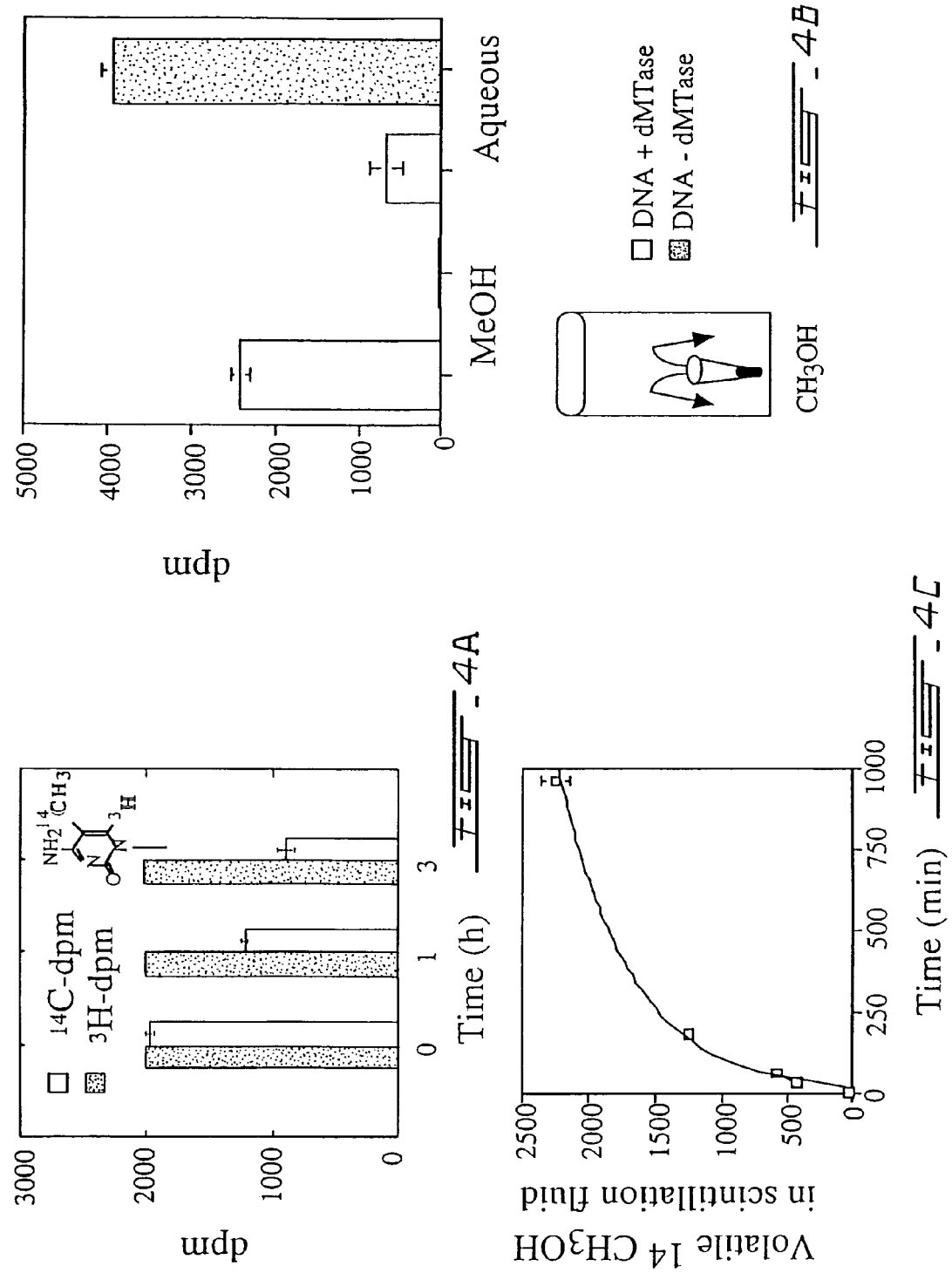

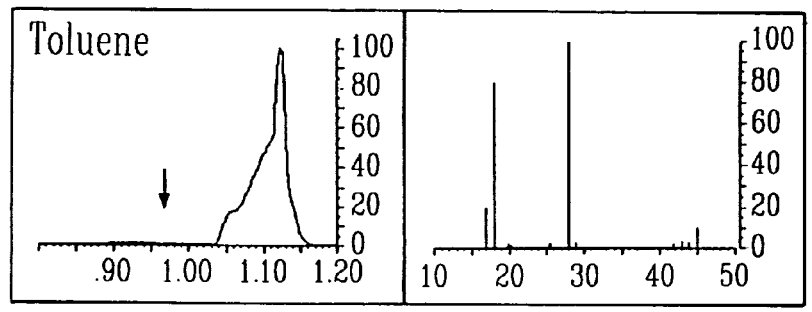
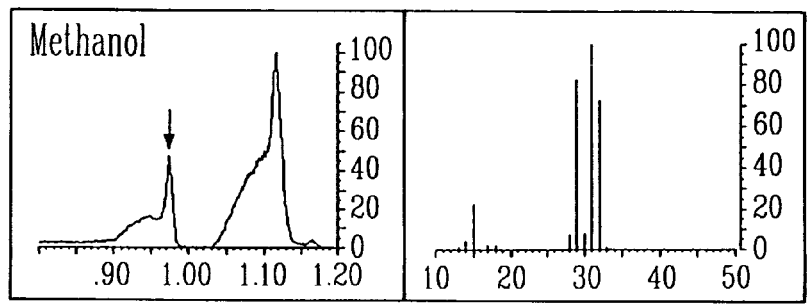
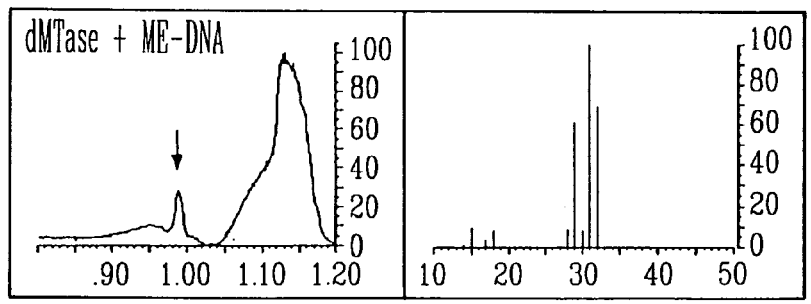
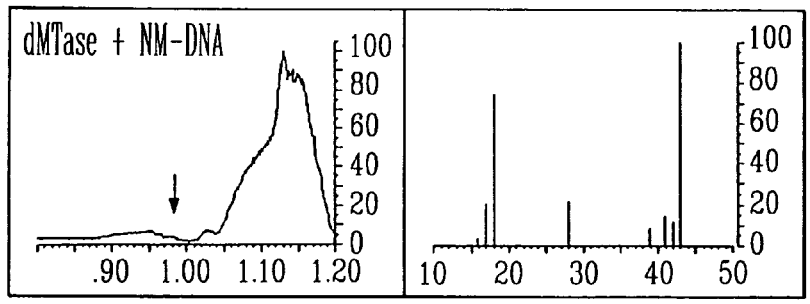
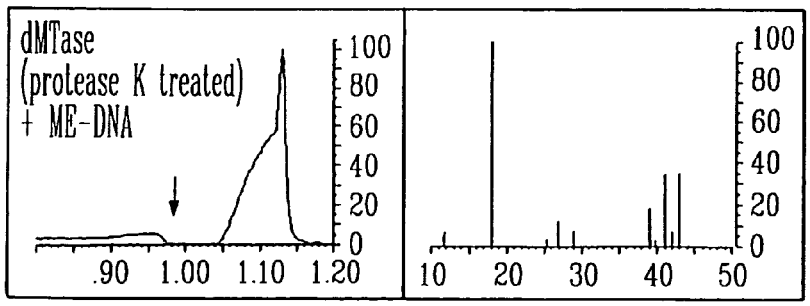
FIG. 4F

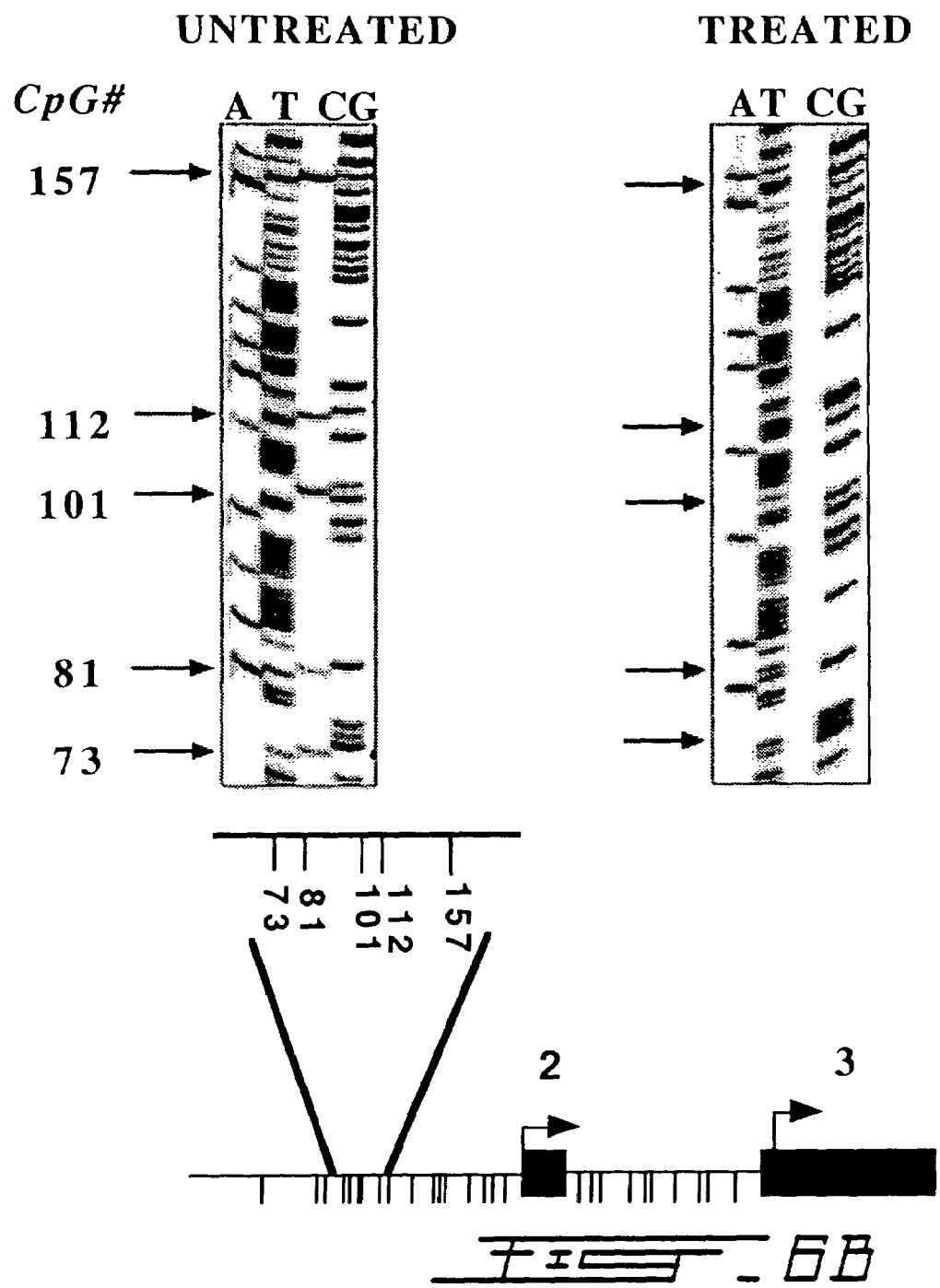

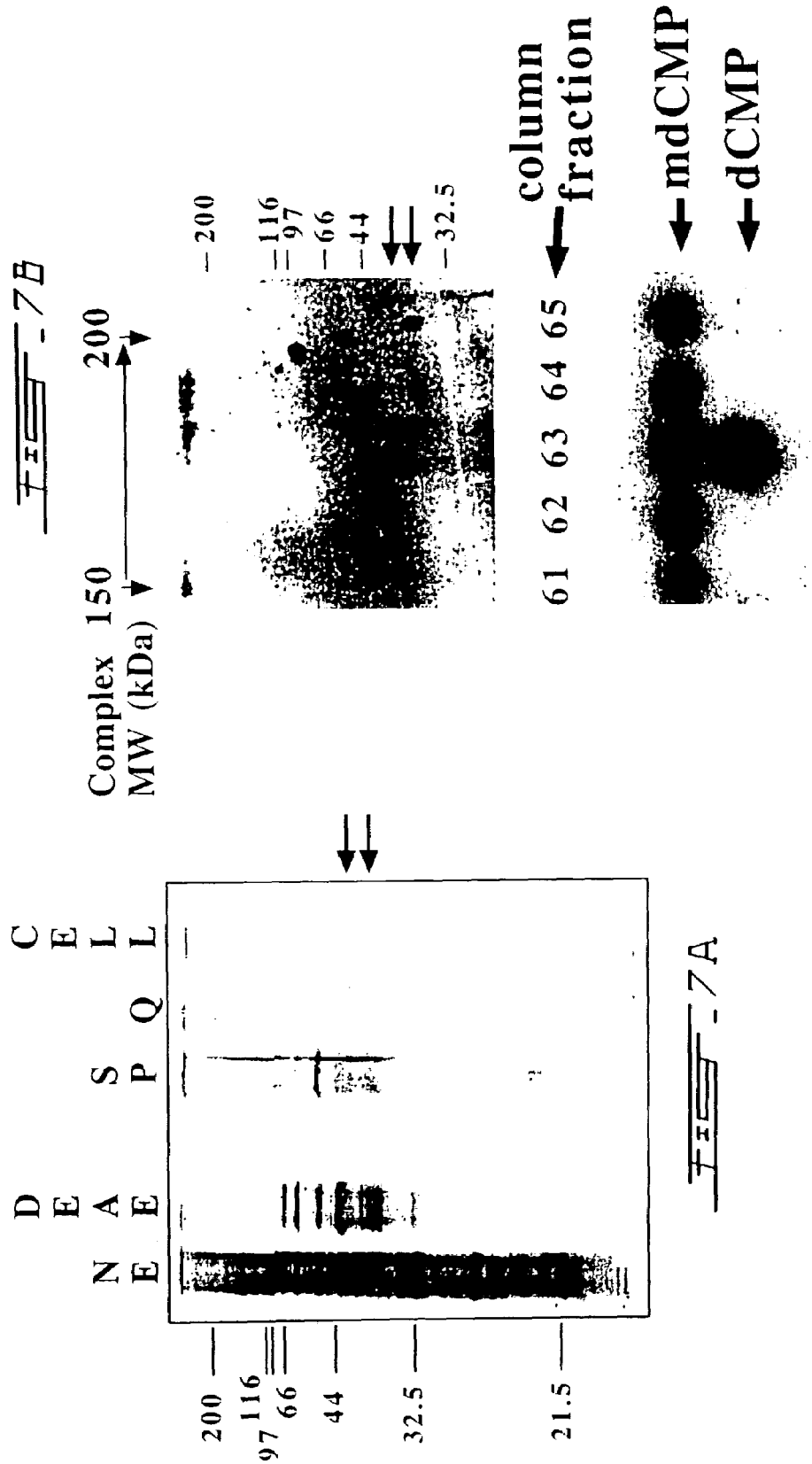

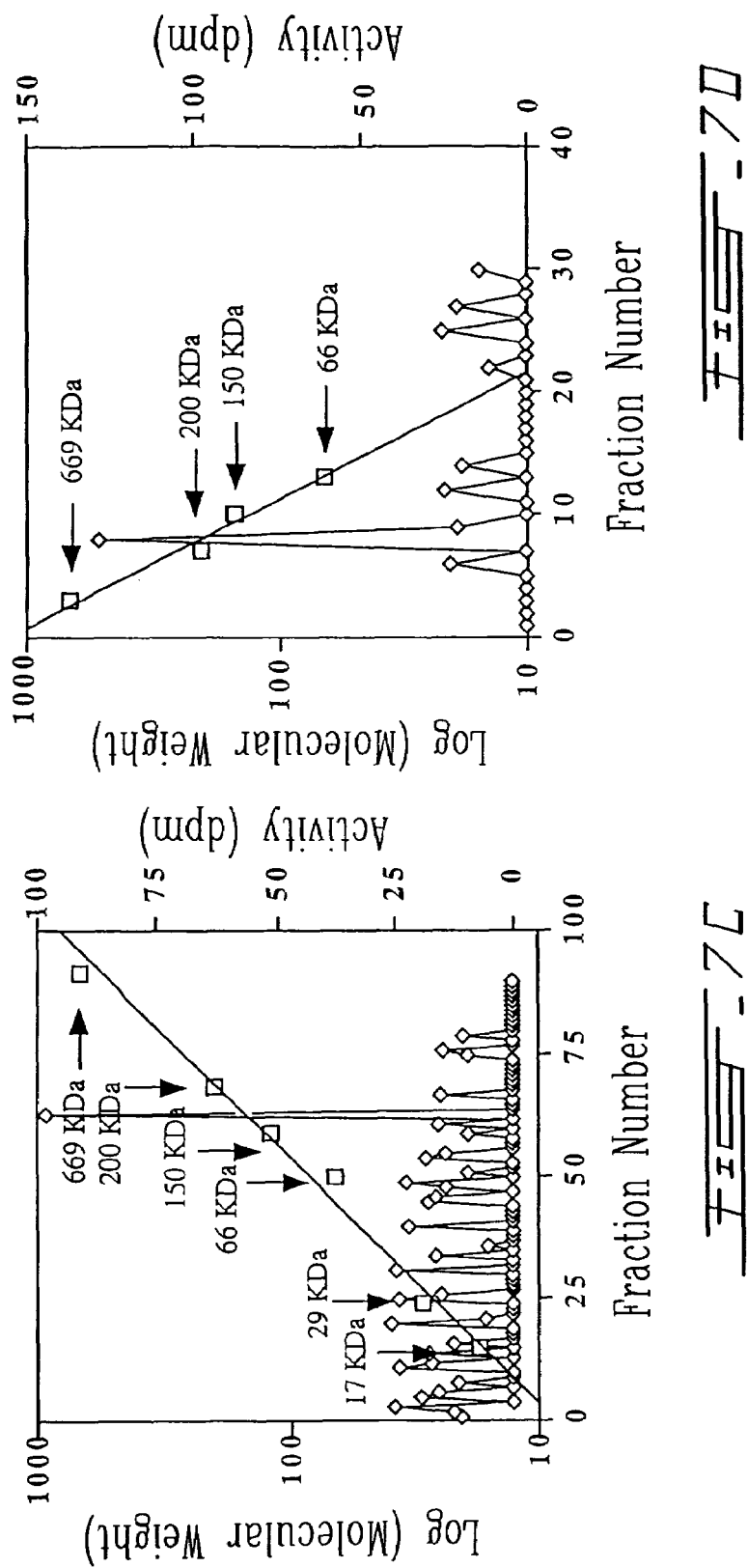

EST        DCPALPPGWKKEVIRKSGLSAGKSDVYYFSPSGKKFRSKPQLARYLGNTVDLS
           ||||  ||||  ||||||||||||||||||||||||  ||||||||||
           D P LP GW  ++    RKSG SAGK DVY  +P GK FRSK PQLARYLGN    DS
           ||||  ||||  ||||||||||||||||||||||||  ||||||||||||||||
MeCP2  15 DDPTLPEGWIRKLKQRKSGRSAGKYDVYLINPQGKAFRSKVELIAYFEKVGDTS 68

FIG-8A

MDCPALPPGW KKEEVIRKSG LSAGKSDVYY FSPSGKKFRS        40
KPQLARYLGN TVDLSSFDFR TGKMMPSKLQ KNKQRLRNDP        80
LNQNKGKPDL NTTLPIRQTA SIFKQPVTKV TNHPSNKVKS        120
DPQRMNEQPR QLFWEKRLQG LSASDVTEQI IKTMELPKGL        160
QGVGPGSNDE TLLSAVASAL HTSSAPITGQ VSAAVEKNPA        200
VWLNTSQPLC KAFIVTDEDI RKQEERVQQV RKILEDALMA        240
DILSRAADTE EMDIEMDSGD EA                          262

§§§ homology to methylated DNA binding domain
▨▨▨ homology to coiled coil domain

FIG-8B

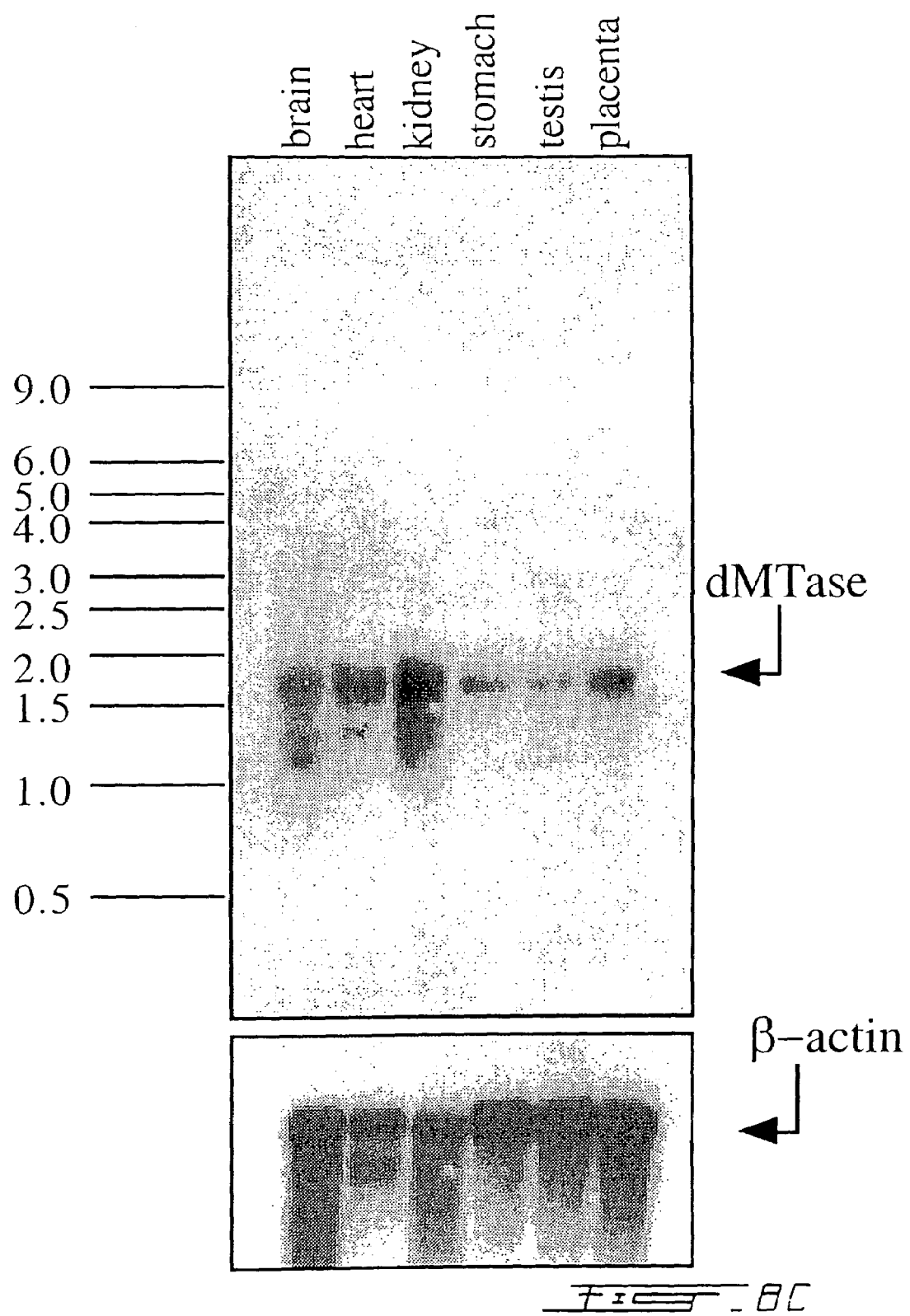

Human DNA demethylase cDNA-dMTase1 and predicted amino acid sequence

5' gggggcgtgg cccgagaag gcggagacaa gcggagccgc gatggccgcc catagcgctt ggaggaccta
agaggcggtg gcggggcca cgccccgggc aggaggccg gccgctcta
tgatgcttgc gccgtcccc cgcgcgccgc cgcgcggcg gctgcgggcg ggggtct ccggattcc
aaggctcgg ttacggaaga agcgcagcgc agcgcagcgc cggctgggga ggggctgga tgcgcgcgca
cccggggga ggccgctgct gcccggagca ggaggaggg gagagtgcgg cggggcggcag
cggcgctggc ggcgactccg ccatagagca gggggccag ggcagcgcgc tcgcccgtc
ccggtgagc ggcgtgcgca gggaaggcgc tcgggcggc tggccgtggc cgggcgtggcc ggggcggtg
gaagcaggcg ggccggggcg gcggcgtctg tggccgtggc cgggccgggg gccgtggccg
gggacgggga cggggccggg gccgggggcg gccgggggcg ccgccgtccc ccgagtggcg gcagcggcct
tggcggcgac ggcggcggct cctttcccgt gcggcggcgg cggcagcggt gcggccggcg ccccccggcg
ggagcgggtc cggggagcgc cggggagccg ggggccccg cctcccccc cccggggac cccgggccac
ggagagcggg aagaggatgg attgcccggc gtgctggcaa agcgatgtc ggatggaaga aggaggaagt
gatccgaaaa tctggctaa gtgctggcaa ctcagtggg aagtacctg tactacttca gtccaagtgg
taagaagttc agaagcaagc ctcagtggg gaaagatgat gccctagtaa ttacagaaga acaaacagag
cagtttgac ttcagaactg gaaagatgat atcaaaataa gggtaaacca gacttgaata caacattgcc
actgcgaaac gatcctctca atcaaaataa gggtaaacca gacttgaata caacattgcc
aattagacaa acagcatcaa tttcaaaaca accggtaacc aaagtcacaa atcatcctag

FIG-9A

```
taataaagtg aaatcagacc cacaacgaat gaatgaacag ccacgtcagc ttttctggga
gaagaggcta caaggactta gtgcatcaga tgtaacagaa caaattataa aaaccatgga
actacccaaa ggtcttcaag gagttggtcc aggtagcaat gatgagaccc ttttatctgc
tgttgccagt gctttgcaca caagctctgc gccaatcaca gggcaagtct ccgctgctgt
ggaaaagaac cctgctgttt ggcttaacac atctcaaccc ctctgcaaag cttttattgt
cacagatgaa gacatcagga aacaggagca gcgagtacga caagtacgca agaaattgga
agaagcactg atggcagaca tcttgtcgcg agctgctgat acagaagaga tggatattga
aatggacagt ggagatgaag cctaagaata tgatcaggta actttcgacc gactttcccc
aagrgaaaat tcctagaaat tgaacaaaaa tgtttccact ggcttttgcc tgtaagaaaa
aaaatgtacc cgagcacata gagcttttta atagcactaa ccaatgcctt tttagatgta
tttttgatgt atatatctat tattcaaaaa atcatgttta ttttgagtcc taggacttaa
aattagtctt ttgtaatatc aagcaggacc ctaagatgaa gctgagcttt tgatgccagg
tgcaatctac tggaaatgta gcacttacgt aaaacatttg ttcccccac agttttaata
agaacagatc aggaattcta aataaatttc ccagttaaag attattgtga cttcactgta
tataaacata tttttatact ttattgaaag gggacacctg tacattcttc catcatcact
gtaaagacaa ataaatgatt atattcacaa atattcacaa aaaaaa           3'
```

SEQ ID NO:1

*FIG. 9B*

MRAHPGGGRCCPEQEEGESAAGGSGAGGDSAIEQGGQGSALAPSPVSGVR
REGARGGGRGRGRWKQAGRGGVCGRGRGRGRGRGRGRGRGRGRGRPPSG
GSGLGGDGGGGSGGGGAPRREPVFPSGSAGPGRGPRATESGKRM
DCPALPPGWKKEEVIRKSGLSAGKSDVYFSPSGKKFRSKPQLARYLGNT
VDLSSFDFRTGKMMPSKLQKNKQRLRNDPLNQNKGKPDLNTTLPIRQTAS
IFKQPVTKVTNHPSNKVKSDPQRMNEQPRQLFWEKRLQGLSASDVTEQII
KTMELPKGLQGVGPGSNDETLLSAVASALHTSSAPITGQVSAAVEKNPAV
WLNTSQPLCKAFIVTDEDIRKQEERVQQVRKKLEEALMADILSRAADTEE
MDIEMDSGDEA

SEQ ID NO:2

FIG. 9C

Human DNA demethylase homologue-dMTase2 and predicted amino acid sequence

```
5' agcgggccga ggagccgggc gcaatggagc ggaagaggtg ggagtgccgc gcgctcccgc
    agggctggga gaggaagaa gtgccagagc gggaagaagt tccgcagcaa gccgcagctg gcgcgctacc
    tcttttacta tagcccgagc agcaccttcg acttccgcac gggcaagatg ctgatgagca
    tgggcggctc catggacctg agccgccag cgcgtgcgct acgactcctc caaccaggtc aagggcaagc
    agatgaacaa gagccgcctg cgcgtgcgcc cccgtgcgcc agacgcgtc catcttcaag cagccggtga
    ccgacctgaa caccaccccc agcaacaagg tcaagagcga cccgcagaag gcggtggacc
    ccaagattac gctcttctgg gagaagaagc tgagcggcct gaacgccttc gacattgctg
    agccgcgcca caagaccatg gaccttcccca agggcctgca gggggtggga cctggctgca
    aggagctggt gctgctgtcg gccatccgca gcgccctgca cactagcacc atgcccatca
    cggatgagac ctcggccgcc gtggagaaga accccgcgt atggctcaac accacgcagc
    ccctgtgcaa agccttcatg gtgaccgacg aggacatcag gaagcaggaa gagctggtgc
    agcaggtgcg gaagcggctg gaggaggcgc tgatgccga caaggcctg catgctggcg cacgtggagg
    agctggcccg tgacggggag gaggaggag gccgcgctgg cgccgacccc gccgccgga cacgtctagg
    aagacgagga ggaggaggag ccgtgctgcc tgctggagcc gcctgcagag gcctgcctcg
    gcagaggccc tgccgagagc aaccaggtc gcggcgaag ccagccttg gagacaccca ggaggaaggc
    gccccacgtg aaccaggctc ctccctcct cggcccgtcc ccacttcccg gggcctcggg gcacacagct
    cgtgctcctg gctcctcct gtccctcct ccactttccg gtccttccg tacagagtcc gcttcggga
    ggggctgccc ccaccccgaa gaccctccac gctcgtcctc tacagagtcc ggcttcggga
    agtgccgggt gctcctgggc cctgcctggc ccctgcctgg tccctacgac ctttgggctc gaggccagct
```

FIG. 90

```
cctcccatg  ccgctgtcc  cagctccttg  agactggaga  gcagccagca  ggtgccggc
agctcggcgc  cacggcttgc  tgacagctgg  gagggtttct  cggtctggag  gcgtagttt
gaaactcaca  tcacccactg  tgcagcgtga  ggacgggact  ctggtctgct  gtggggca
tgcaggacgg  cgccactctc  tgccctgcca  tgcggctggt  ggtgccacag  agcctcaccg
tgcctgagtg  gcgtgcccag  ggaggccgct  ctccttcagt  aaatgtaaca  cagtcgaggc
acgtcatcgg  gcagccttcc  ctgtgtgcca  acgcagcct  tcgcttctga  aaaccaaact
ccagccgctg  ccagtcggga  cttggtcgcc  cggcgctgcc  agaatgctcc  actgccagcc
ggccccctg  cctcggtttc  cctctgttt  agtggcgaca  caggcaccca  gctttgggt
ggtgctgacg  ctcccaggg  tgccaggagc  cactgggaca  gggtgaggct  cccagacgct
cctcgaggtg  cccagctctc  caggagctt  ctgccccaag  gcgttcttga  gggatctgct
ccttaacccc  ccagtgcctt  ggcgagggca  ggttccaagc  cacagacgcc  tgccccgagt
ggactttgcg  gccagtccct  gggtgccttc  ctgggccctg  cttgccagt  gagggttcct
aacgggtggg  ttcawtggcc  tggcccvagc  gagcccccac  ctgcattgac  cttaggccca
tagagagggc  ctgtcccggt  gctgcccggt  ccaaggatct  ggtcgctgcc  ccaggggac
tgatgggcaa  gagtcgcccc  tgtgctgga  ctgtgaccat  ccctgatggg  gcctgaccgc
gggagctgag  gaagcgccgc  tccaccgtct  gccctccaag  gacccgcatg  gaggcagtgg
gctggcagct  tcctgctgct  ccctgtcaga  gtcaaagcac  aaatcctcag  gacgggctca
agggccaggg  cagccgaggg  aagctccagg  tggggaccac  gtcttcctga  ggttggtgcc
cactgggctgg  gacccttgc  agtggggtgg  cctcccctct  gtctgcctgg  tgaggagc
cgtgggcgtg  gggacgtgac  tgaataaagc  caccatgggt  ggatgtgctt  gg         3'
```

SEQ ID NO:3

FIG. 9E

MERKRWECPALPQGWEREEVPRRSGLSAGHRDVFYYSPSGKKFRSKPQLA
RYLGGSMDLSTFDFRTGKMLMSKMNKSRQRVRYDSSNQVKGKPDLNTALP
VRQTASIFKQPVTKITNHPSNKVKSDPQKAVDQPRQLFWEKKLSGLNAFD
IAEELVKTMDLPKGLQGVGPGCTDETLLSAIASALHTSTMPITGQLSAAV
EKNPGVWLNTTQPLCKAFMVTDEDIRKQEELVQQVRKRLEEALMADMLAH
VEELARDGEAPLDKACAEDDDEEEEEEEPDPDPEMEHV SEQ ID NO:4

FIG. 9F

```
Lipman-Pearson Protein Alignment
Ktuple: 2; Gap Penalty: 4; Gap Length Penalty: 12
                                    Similarity                    Gap        Consensus
Seq1(1>411)    Seq2(1>291)           Index        Gap Number    Length       Length
human dMTase1 protein  human dMTase2 protein
(148>397)      (4>253)                76.0            0            0           250
(148>397)      (4>253)                76.0            0            0           250
    v150       v160       v170       v180       v190       v200       v210
KRMDCPALPPGWKKEEVIRKSGLSAGKSDVYYFSPSGKKFRSKPQLARYLGNTVDLSSFDFRIGKMPSK
KR :CPALP.GW.:EEV R:SGLSAG..DV:Y:SPSGKKFRSKPQLARYLG.::DLS:FDFRIGKM: SK
KRWECPALPQGWEREEVPRRSGLSAGHRDVFYYSPSGKKFRSKPQLARYLGGSMDLSTFDFRIGKMLNSK
    ^10        ^20        ^30        ^40        ^50        ^60        ^70 v220       v230       v240       v250       v260       v270       v280
LQKNKQRLRNDPLNQKGKPDLNTTLPIRQTASIFKQPVTKVINHPSNKVKSDPQRMNEQPRQLFWEKRL
::K::QR:R D: NQ KGKPDLNT:LP:RQTASIFKQPVTK.:TNHPSNKVKSDPQ: :QPRQLFWEK:L
MNKSRQRVRYDSSNQVKGKPDLNTALPVRQTASIFKQPVTKITNHPSNKVKSDPQKAVDQPRQLFWEKKL
    ^80        ^90        ^100       ^110       ^120       ^130       ^140
```

FIG. 9G

```
              v290        v300       v310       v320       v330       v340       v350
QGLSASDVTEQIIKIMELPKGLQGVGPGSNDETLLSAVASALHTSSAPITGQVSAAVEKNPAWMLNTSQP
GL:A  D::E:::KIM:LPKGLQGVGPG..DETILLSA:ASALHTS: PITGQ:SAAVEKNP:WMLNT:QP
SGINAFDIAEELVKIMDLPKGLQGVGPGCTDETLLSATASALHTSIMPITGQLSAAVEKNPGWMLNTTQP
          ^150       ^160       ^170       ^180       ^190       ^200       ^210 v360       v370       v380       v390
LCKAFTVIDEDIRKQEERVQQVRKKLEEALMADILSRAAD
LCKAF:VTIDEDIRKQEE  VQQVRK:LEEEALMAD:L::..:
LCKAFMVTIDEDIRKQEELVQQVRKRLEEALMADMLAHVEE
          ^220       ^230       ^240       ^250
```

FIG-9H

Mouse DNA demethylase-dMTase1 and predicted amino acid sequence

```
5'cgctctgcg ggcggggcgg gtctccggga ttccaagggc tcggttacgg aagaagcgca
  gagccggctg gggaggggc  tggatgcgcg cgcacccggg cgcaggccgc tgctgcccgg
  agcaggagga ggggagagc  gcgcggggcg gcagcggcgc tggcggcgac tccgccatag
  agcaggggg  ccaggcagc  gcgctcgctc cgtccccggt gagcggcgtg cgcagggaag
  gcgctcgggg cggcggccgt ggccggggg  ggtggaagca ggcggcccgg ggcggcggcg
  tctgtggccg tggccgtggc cgtggccggg gtcggggccg tggccggggc cggggccggg
  gccgcggccg tcccagagt  ggcggcagcg gccttggcg  cgacggcggc ggcggcgcgg
  gccgctgcgg cgtcggcagc ggtggcggcg ggggatcct  gcgggatcct gtccctttcc
  cgtcggggag ctcggggccg gggcctcccc gggcccaggg gaccggagc  cacggagagc gggaagagga
  tggactgccc ggccctcccc cccggatgga agaaggagga agtgatccga aaatcagggc
  tcagtgctgg caagagcgat gtctactact tcagtccaag tggtaagaag ttcagaagta
  aacctcagct ggcaagatac ctgggaaatg ctgtttgacct tagcagtttt gacttcagga
  ccggcaagat gatgcctagt aaattacaga agaacaagca gagactccgg aatgaccccc
  tcaatcagaa caagggtaaa ccagacctga acacaacatt gccaattaga caaactgcat
  caattttcaa gcaaccagta accaaattca cgaaccaccc gagcaataag gtgaagtcag
  accccccagcg gatgaatgaa caaccacgtc agcttttctg ggagaagagg ctacaaggac
  ttagcgcatc agatgtaaca gaacaaatta taaaaaccat ggagctacct aaaggtcttc
  aaggagtcgg tccaggtagc aatgacgaga ccctcctgtc tgctgtggcc agtgctttac
```

*FIG-19*

```
acacaagctc tgcgcccatc acaggacaag tctctgctgc cgtggaaaag aaccctgctg
tttggcttaa cacatctcaa cccctctgca aagctttcat tgttacagat gaagacatta
ggaaacagga agagcgagtc caacaagtac gcaagaaact ggaggaggca ctgatggccg
acatcctgtc ccggctgcg gacacggagg aagtagacat tgacatggac agtggagatg
aggcgtaaga atatgatcag gtaactttcg actgaccttc cccaagagca aattgctaga
aacagaatta aaacatttcc actgggtttc gcctgtaaga aaaagtgtac ctgagcacat
agcttttta tagcactaac caatgccttt ttagatgtat tttgatgta tatatctatt
attccaaatg atgtttattt tgaatcctag gacttaaaat gagtctttta taatagcaag
cagggccctt ccggtgcagt gcagctttga ggccaggtgc agtctactgg aaaggtagca
cttacgtgaa atatttgttt ccccacagt tttaatataa acagatcagg agtaccaaat
aagtttccca attaaagatt attatacttc actgtatata aacagatttt tatactttat
tgaaagaaga tacctgtaca ttcttccatc atcactgtaa agacaaataa atgactatat
tcac    3'
```

SEQ ID NO:5

FIG. 9J

MRAHPGGGRCCPEQEEGESAAGGSGAGGDSAIEQGGQGSALAPSPVSGVR
REGARGGGRGRWKQAARGGGVCGRGRGRGRGRGRGRGRGRGRGRPQSG
GSGLGGDGGAGGCGVGSGGGVAPRRDPVPFPSGSSGPGPRGPRATESG
KRMDCPALPPGWKKEEVIRKSGLSAGKSDVYFSPSGKKFRSKPQLARYL
GNAVDLSSFDFRTGKMMPSKLQKNKQRLRNDPLNQNKGKPDLNTTLPIRQ
TASIFKQPVTKFTNHPSNKVKSDPQRMNEQPRQLFWEKRLQGLSASDVTE
QIIKTMELPKGLQGVGPGSNDETLLSAVASALHTSSAPITGQVSAAVEKN
PAVWLNTSQPLCKAFIVTDEDIRKQEERVQQVRKKLEEALMADILSRAAD
TEEVDIDMDSGDEA

SEQ ID NO: 6

FIG. 9K

Mouse DNA demethylase-dMTase2 and predicted amino acid sequence

```
5' cacgcgcggg cgggtgggcg gagcggcccc cctagcgggg gctgtgaagc gcggggaggg
   ggccgagcgg gtggcgaagc cggcgcgcgc ccgcgctgggg gcggagggcg gaggccgtg
   ggacagaaca gctgcggcga gtgcgcggga ccgaatcggcg acgagcccgg
   gggtcgcaaa ttgcagaaag ggcggcgggcg gcggcatcgg ccacggcggg cggaaaagcc
   gggcgcaat ggagcggaag agtgggagt gcccggcgct gcccgcaggg cccgcagggc tgggaaaggg
   aagaagtgcc caggaggtcg gggctgtcgg ccggccacag ggatgtcttt tactatagcc
   ccagcgggaa gaagttccgc agcaagccac aactggcacg ttacctgggc ggatccatgg
   acctcagcac cttcgacttc cgcaccggaa agatgttgat gaacaagatg aataagagtc
   gccagcgtgt gcgctatgat tcttccaacc agtcctgac ctgaacaccg
   cgctgcctgt acggcagact gcatccatct gcatccaag gtgaccaag atcaccaacc
   acccagcaa caaggtcaag agcgacccgc agaaggcagt ggaccagccg agcagcttt
   tctgggagaa gaagctaagt ggattgagtg cctttgacat tgcagaagaa ctggtcagga
   ccatggactt gcccaagggc ctgcagggag ctgcagggcc tggcccctgg ctgtacagat gagacgctgc
   tgtcagccat tgcgagtgct ctacacacca gcaccctgcc cattacaggc cagctctctg
   cagccgtgga gaagaaccct ggtgtgtggc tgaacactgc acagccactg tgcaaagcct
   tcatggtgac agatgacgac atcaggagac gtacagcag ggtacagcag gtacggaagc
   gcctggagga ggcactgatg gccgacatgc gccgagacg gccgagacg
   ggggaaggcacc actggacaag aggagcaaag ccctgtgcag aggaggaaga ggaggaggag
```

Fig. 76

```
aagagccgga gccagagcga gtgtagcaca ggtgccctgc ccaagtctgg gctgcagact
gccttcagcc ttgcctggac caggtagggg ccagacctgt aggaggcagc cgtccacctc
ctttccaaag cctcctgctt ccaggtctca gtgcagggag cccctgtgga ccttgaactc
acttgtccct gcgctgcctg gcaggaagcc ccacactgaa agcagatgag cagtgaccca
actgagaggc cacctggaca cagtcacctc cctgcctcct tatcatagga caaggccttg
cttggcaccg aggagctggg agccgtgttg ggtgctggag gaagtttctg gaaacacacc
tggctatgcc caccttatgt ccctaaggct attacaggcc agggtttgga ctgctccggc
ccacagggct gcccagcctc cccacactga gggtcagcag cccaccagga agtcactttc
cttcaataaa ctgatggtag gaacttgtg 3'
```

SEQ ID NO:7

*Fig. 9M*

MERKRWECPALPQGWEREEVPRRSGLSAGHRDVFYYSPSPGKKFRSKPQLA
RYLGGSMDLSTFDFRTGKMLMNKMNKSRQRVRYDSSNQVKGKPDLNTALP
VRQTASIFKQPVTKITNHPSNKVKSDPQKAVDQPRQLFWEKKLSGLSAFD
IAEELVRTMDLPKGLQGVGPGCTDETLLSAIASALHTSTLPITGQLSAAV
EKNPGVWLNTAQPLCKAFMVTDDDIRKQEELVQQVRKRLEEALMADMLAH
VEELARDGEAPLDKACAEEEEEEEEEPEPERV

SEQ ID NO:8

FIG. 5

```
Lipman-Pearson Protein Alignment
Ktuple: 2;  Gap Penalty: 4;  Gap Length Penalty: 12
                                    Similarity    Gap     Gap     Consensus
Seq1(1>414)      Seq2(1>285)        Index         Number  Length  Length
mouse dMTase1 protein  mouse dMTase2 protein
(151>400)        (4>253)             75.2          0       0      250
(151>400)        (4>253)             75.2          0       0      250 v160      v170      v180      v190      v200      v210      v220
KRMDCPALPPGMKKEEVIRKSGLSAGKSDVYYFSPSGKKFRSKPQLARYLGNAVDLSSFFDFRIGKMPSK
KR :CPALP.GM..EEV R:SGLSAG..DV:Y:SPSGKKFRSKPQLARYLG..:DLS:FDFRIGKM: :K
KRMECPALPQGMEREEVPRRSGLSAGHRDVFYYSPSGKKFRSKPQLARYLGGSMDLSTFDFRIGKMLMNK
              ^10       ^20       ^30       ^40       ^50       ^60       ^70 v230      v240      v250      v260      v270      v280      v290
LQKNKQRLRNDPLNQNKGKPDINTTLPIRQTASIFKQPVIKFTNHPSNKVKSDPQRMNEQPRQLFWEKRL
::K::QR:R D: NQ KGKPDINT:LP:RQTASIFKQPVTK:TNHPSNKVKSDPQ: :QPRQLFWEK:L
MNKSRQRVRYDSSNQVKGKPDINIALPVRQTASIFKQPVIKITNHPSNKVKSDPQKAVDQPRQLFWEKKL
              ^80       ^90       ^100      ^110      ^120      ^130      ^140
```

FIG. 90

```
                v300       v310       v320       v330       v340       v350       v360
QGLSASDVTEQIIKIMELPKGLQGVGPGSNDETLLSAVASALHTSSAPTTGQVSAAVEKNPAWLNTSQP
GLSA D::E::::TM:LPKGLQGVGPG..DETLLSA:ASALHTS: PTTGQ:SAAVEKNP:VWLNT:QP
SGLSAFDIAEELVRTMDLPKGLQGVGPGCIDETLLSAIASALHTSTLPTTGQLSAAVEKNPGWLNTAQP
      ^150       ^160      ^170     ^180      ^190      ^200     ^210 v370       v380       v390       v400
LCKAFIVIDEDIRKQEERVQQVRKKLEEAIMADILSRAAD
LCKAF:VID:DIRKQEE VQQVRK:LEEAIMAD:L::..:
LCKAFMVIDDDIRKQEELVQQVRKRLEEAIMADMLAHVEE
      ^220       ^230      ^240      ^250
```

FIG. 9P

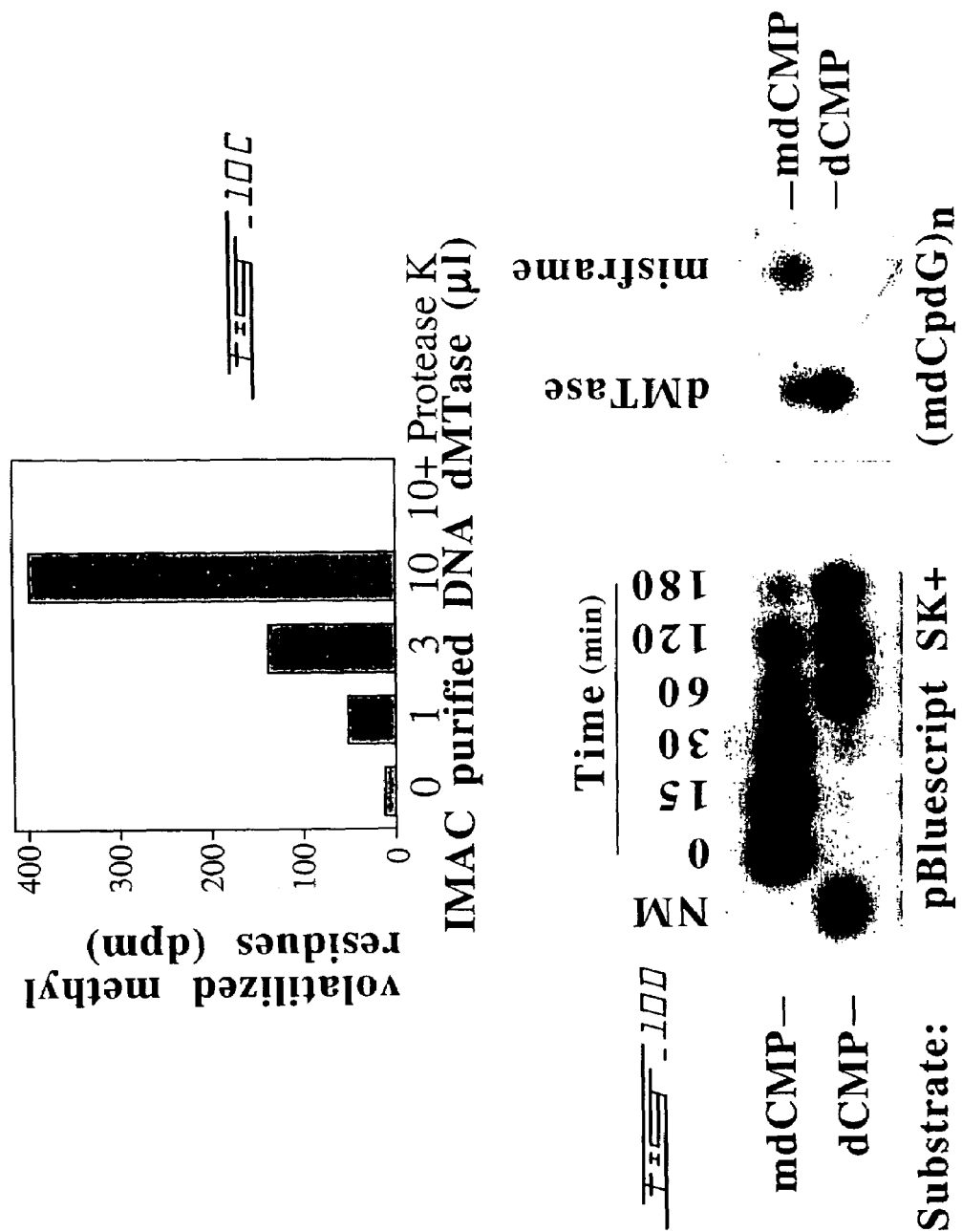

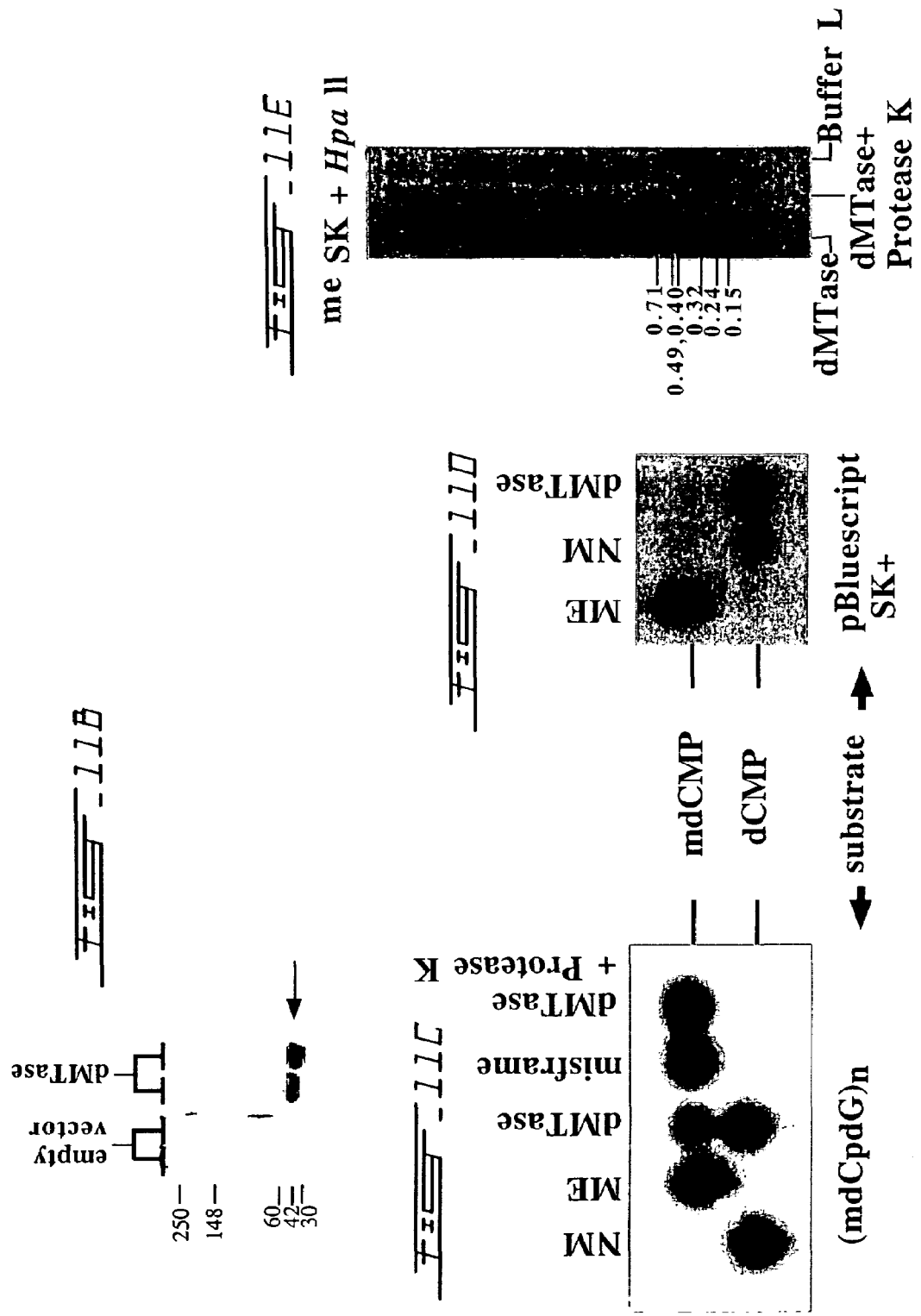

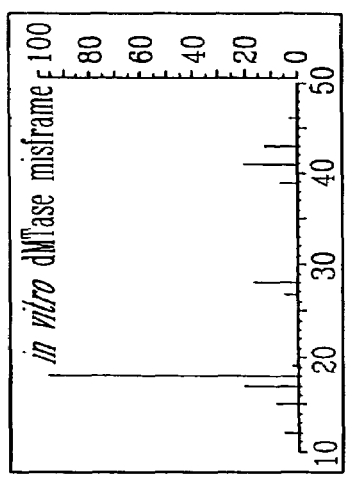
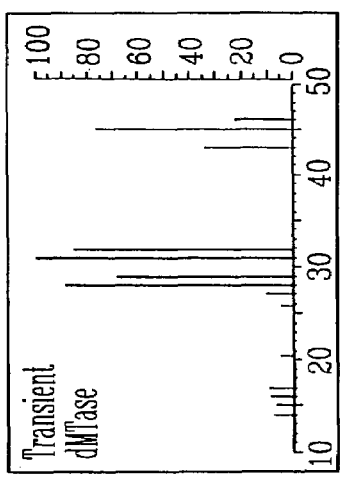
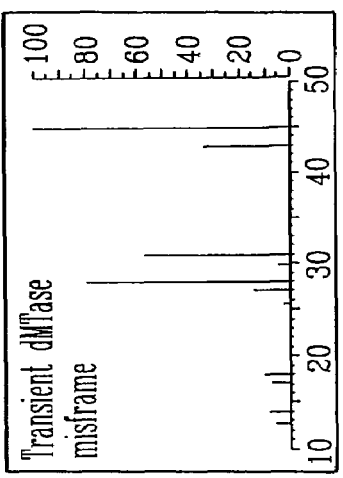
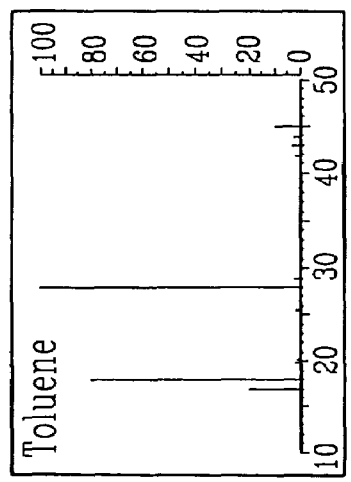
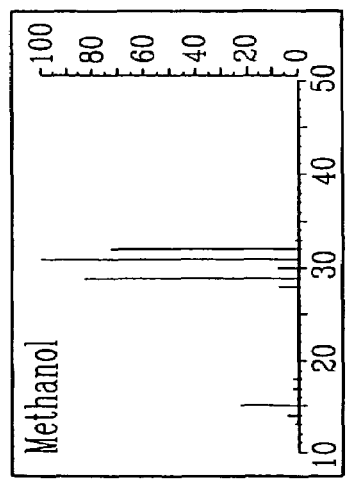
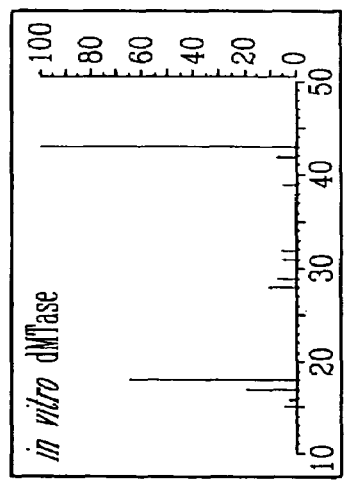
FIG. 12B

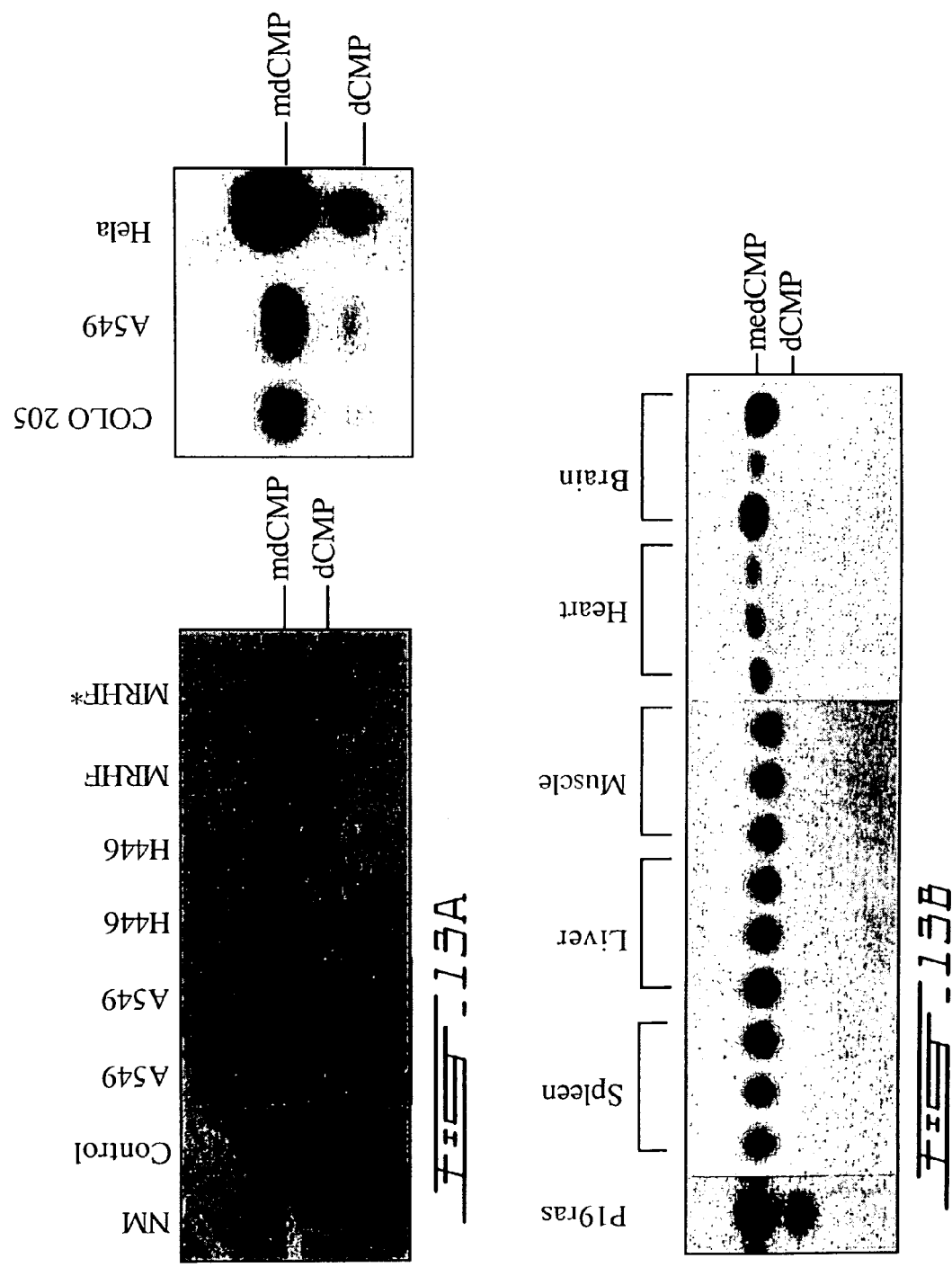

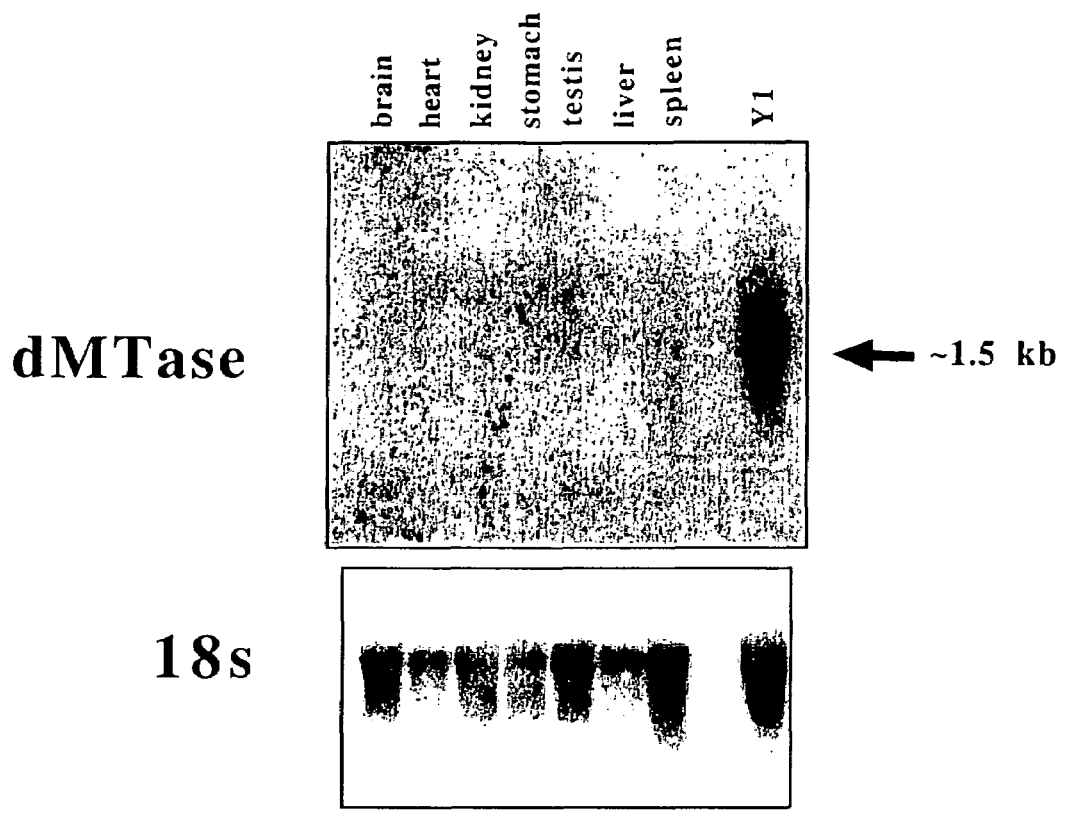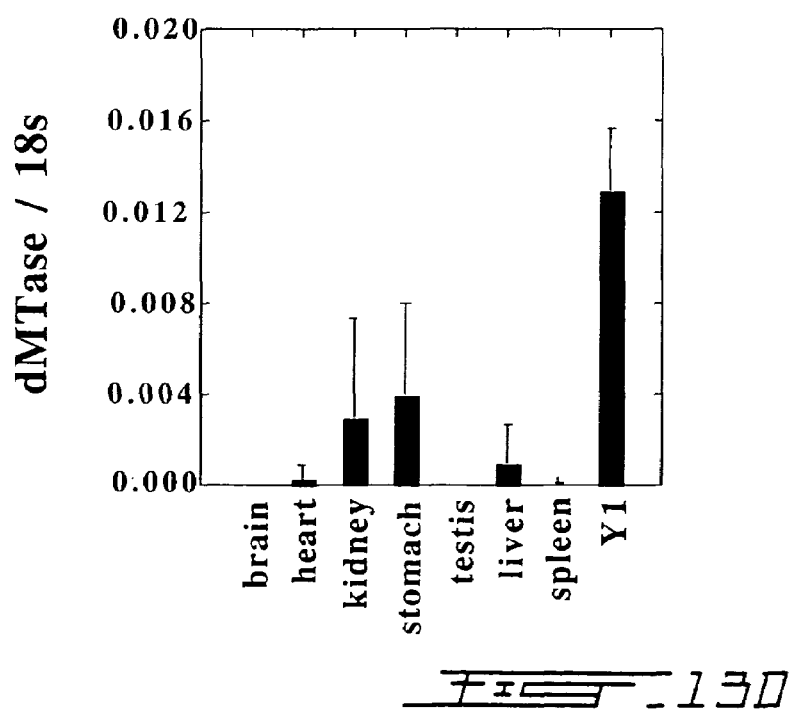
FIG. 13D

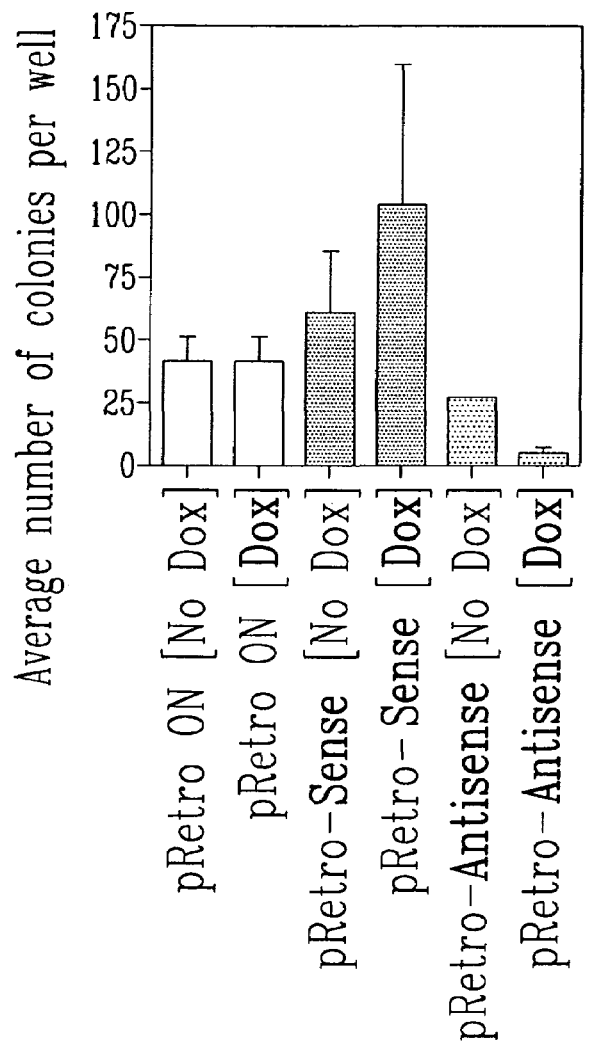
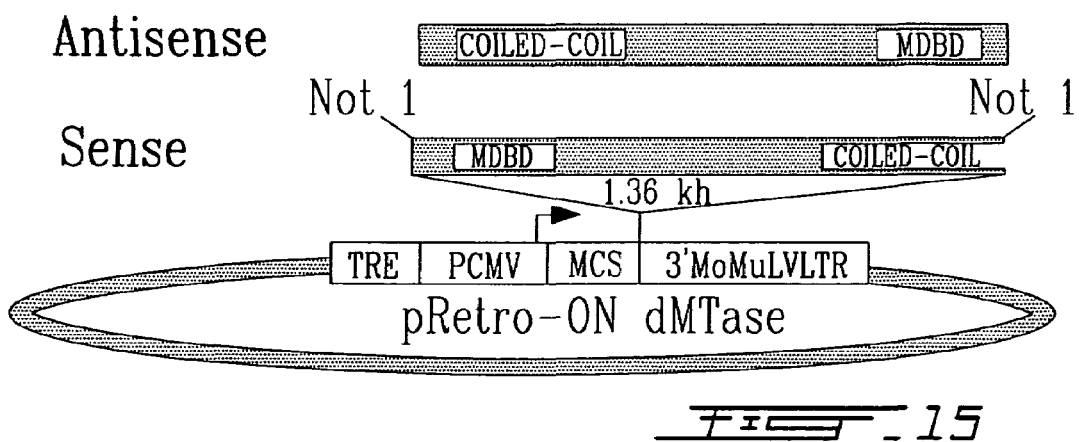
FIG. 15

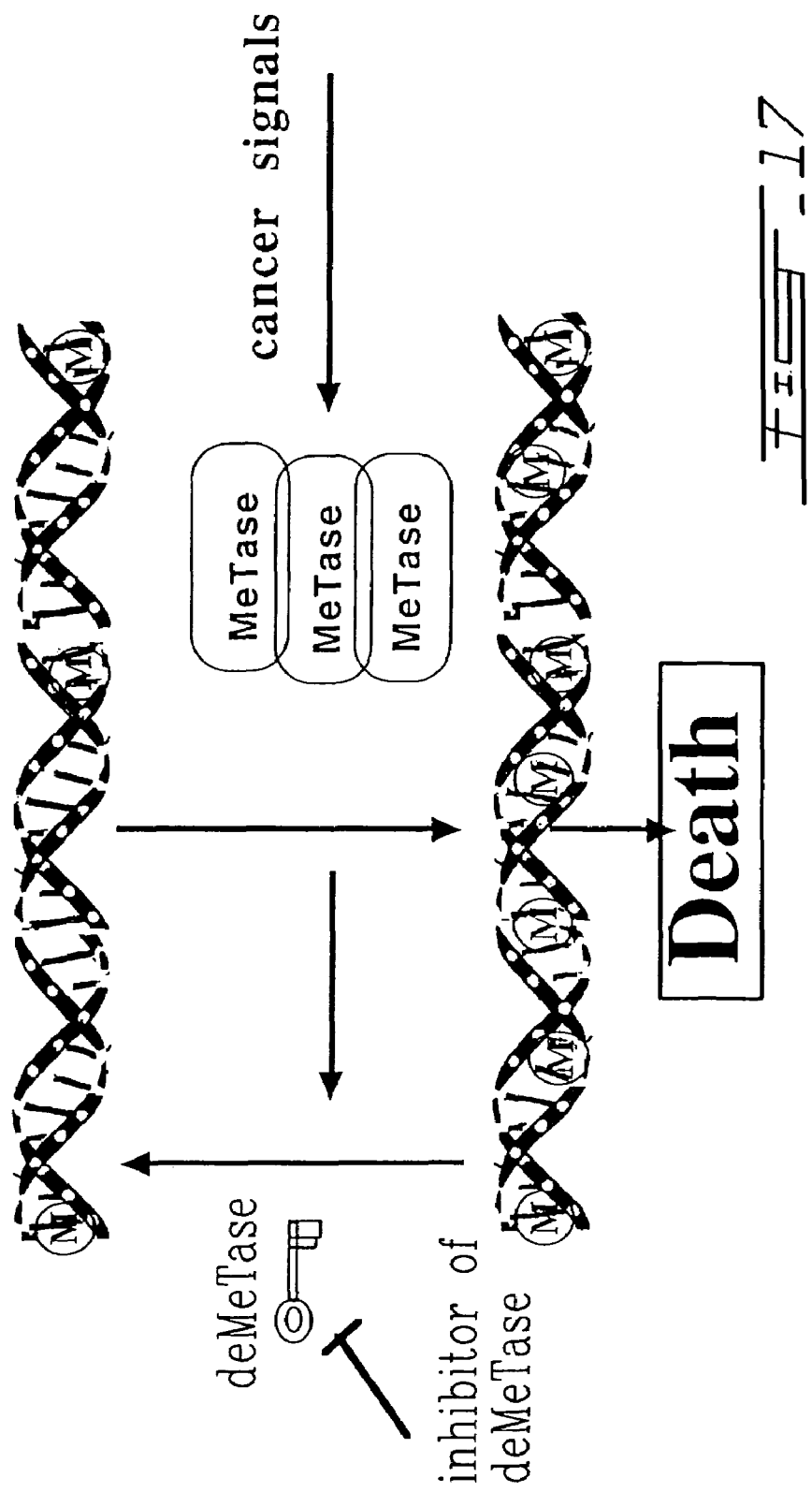

DNA DEMETHYLASE, THERAPEUTIC AND DIAGNOSTIC USES THEREOF

BACKGROUND OF THE INVENTION (a) Field of the Invention

The invention relates to a novel enzyme, DNA demethylase, therapeutic and diagnostic uses thereof.

(b) Description of Prior Art

Many lines of evidence have established that modification of cytosine moieties residing in the dinucleotide sequence CpG in vertebrate genomes is involved in regulating a number of genome functions such as parental imprinting, X-inactivation, suppression of methylation of ectopic genes and differential gene expression (Szyf, M. (1996) Pharmacol. Ther. 70, 1–37). DNA methylation performs its function of differentially marking genes because the distribution of methylated CpGs is tissue- and site-specific forming a pattern of methylation (Szyf, M. (1996) Pharmacol. Ther. 70, 1–37). It is clear that the pattern of methylation is fashioned by a sequence of methylation and demethylation events (Brandeis, M. et al. (1993) Bioassays 15, 709–713) during development and is maintained in the fully differentiated cell (Razin, A. et al. (1980) Science 210, 604–610). While it was originally suggested that DNA demethylation is accomplished by a passive loss of methyl groups during replication (Razin, A. et al. (1980) Science 210, 604–610), it is now clear that an active process of demethylation occurs in embryonal cells (Frank, D. et al. (1991) Nature 351, 239–241), in differentiating cell lines (Razin, A. et al. (1986) Proc. Natl. Acad. Sci. USA 83, 2827–2831; Szyf, M. et al. (1985) Proc. Natl. Acad. Sci. USA 82, 8090–8094) and in response to estrogen treatment (Saluz, H. P. et al. (1986) Proc. Natl. Acad. Sci. USA 83, 7167–7171). Two modes of demethylation have been documented: site specific demethylation that coincides in many instances with onset of gene expression of specific genes and a general genome wide demethylation that occurs during early development in vivo during cellular differentiation and in cancer cells (Feinberg, A. P. et al. (1983) Nature 301, 89–92; Razin, A. et al. (1986) Proc. Natl. Acad. Sci. USA 83, 2827–2831). The global demethylation is consistent with the hypothesis that a general demethylase activity which is activated at specific points in development or oncogenesis exists. It has been hypothesized that one mechanism regulating the pattern of methylation is the control of expression of methyltransferase (Szyf, M. (1991) Biochem. Cell Biol. 69, 764–767) and demethylase activities (Szyf, M. (1994) Trends Pharmacol. Sci. 7, 233–238). Although extensive information has been obtained on the enzymatic activity responsible for methylation and the regulation of its expression in the last two decades (Szyf, M. (1996) Pharmacol. Ther. 70, 1–37), the identity of the demethylase has remained a mystery. It is clear however that to fully understand how patterns of methylation are formed and maintained and to determine their role in development, physiology and oncogenesis, one has to identify the demethylase enzyme(s). Two main difficulties have inhibited the identification of this enzyme. First, it is believed that demethylation of a methylated cytosine is chemically highly unlikely since it involves breaking a very stable C—C bond. Second, demethylation occurs at very defined stages in development (Brandeis, M. et al. (1993) Bioassays 15, 709–713) and identifying an adequate tissue source for this enzyme is critical.

Whereas no bona fide demethylase has been identified to date, alternative biochemical mechanisms involving exchange of methylated cytosines with non-methylated cytosines have been described. One previously proposed mechanism is removal of the methylated base by a glycosylase and its replacement with a non-methylated nucleotide utilizing an "excision-repair" mechanism (Razin, A. et al. (1986) Proc. Natl. Acad. Sci. USA 83, 2827–2831). Glycosylase activities that can remove methylated cytosines from DNA have been demonstrated by Vairapandi and Duker (Vairapandi, M. et al. (1993) Nucl. Acids Res. 21, 5323–5327) and more recently by Jost (Jost, J. P. et al. (1995) J. Biol. Chem. 270, 9734–9739). However it is not clear whether this activity is responsible for the general demethylation observed in cellular differentiation. The fact that the activity identified by Jost acts specifically on hemimethylated sequences (which is not the natural substrate in most cases) and can remove thymidines as well as 5-methylcytosines, supports a repair function for this glycosylase-demethylase (Jost, J. P. et al. (1995) J. Biol. Chem. 270, 9734–9739). An alternative mechanism involving a RNA dependent activity has been recently described by Weiss et al. (Weiss et al., 1996). This proteinase-insensitive RNA dependent activity has been shown to catalyze the excision and replacement of a methylated CpG dinucleotide with a nonmethylated CpG dinucleotide that is contained in a DNA-RNA hybrid molecule (Weiss, A. et al. (1996) Cell 87, 709–718). This activity which was identified in differentiating cells in culture was proposed to be involved in demethylation during development. These previous findings demonstrate that the common accepted model in the filed has been that a bona fide demethylase does not exist.

It has been previously proposed that the extensive hypomethylation observed in cancer cells might be a consequence of activation of demethylase activity by oncogenic pathways (Szyf, M. (1994) Trends Pharmacol. Sci. 7, 233–238; Szyf, M. et al. (1995) J. Biol. Chem. 270, 12690–12696). In accordance with this hypothesis we have shown that ectopic expression of v-Ha-ras had induced demethylation activity in the cells (Szyf, M. et al. (1995) J. Biol. Chem. 270, 12690–12696). Using an assay that directly measures the conversion of 3' $^{32}$P labeled methyl dCMP (mdCMP) into dCMP, we have shown that nuclear extracts prepared from P19-Ras transfectants bear high levels of demethylase activity (Szyf, M. et al. (1995) J. Biol. Chem. 270, 12690–12696). Building on this observation, we hypothesized that cancer cell lines were a good source for demethylase. However, it is not evident that Ras expression in p19 cells does reflect the situation in cancer cells. P19 is an embryonic cell and expression of Ras might be differentiating them.

It would be highly desirable to be provided with a bona fide DNA demethylase (DNA dMTase) to alter developmental programs for therapeutic and biological use.

SUMMARY OF THE INVENTION

In accordance with the present invention, we demonstrate the purification of a bona fide DNA demethylase (DNA dMTase) from a human lung cancer cell line A549, determine its kinetic parameters and substrate specificity. The DNA dMTase activity identified in this study converts methyl-dCMP (mdCMP) residing in the dinucleotide sequence mdCpG into dCMP whereas the methyl group is released as a volatile residue which was identified to be methanol. The activity is purified away from any trace amounts of dCTP, is insensitive to the DNA polymerase inhibitor ddCTP, is not affected by the presence of methyl dCTP (mdCTP) in the reaction and does not exhibit exonuclease or glycosylase activities. The identification of this new enzyme points out to new directions in our understanding of how DNA methylation patterns are formed and altered.

One aim of the present invention is to provide a bona fide DNA demethylase (DNA dMTase).

In accordance with the present invention there is provided a DNA demethylase enzyme having about 40 KDa, and wherein the DNA demethylase enzyme is over-expressed in cancer cells and not in normal cells.

In accordance with the present invention there is provided a cDNA encoding human demethylase which comprises a sequence set forth in SEQ ID NO:1.

In accordance with the present invention there is provided two mouse cDNAs homologous to the human cDNA, wherein the cDNA encoding mouse demethylase having a sequence set forth in SEQ ID NOS:5–7.

In accordance with the present invention there is provided a different human cDNA which encodes a protein homologous to the human demethylase having a sequence set forth in SEQ ID NO:3.

In accordance with the present invention there is provided the use of the expression of demethylase cDNAs to alter DNA methylation patterns of DNA in vitro in cells or in vivo in humans, animals and in plants.

The demethylase cDNAs expression may be under the direction of mammalian promoters, such as CMV.

The demethylase cDNAs expression may be under plant specific promoters to alter methylation in plants and to allow for altering states of development of plants and expression of foreign genes in plants.

The demethylase cDNAs expression may be in the antisense orientation to inhibit demethylase in cancer cells for therapeutic processes.

The expression of demethylase cDNA in mammalian cells may be to alter their differentiation state and to generate stem cells for therapeutics, cells for animal cloning and to improve expression of foreign genes.

In accordance with the present invention there is provided the use of the expression of demethylase cDNAs in bacterial or insect cells for production of large amounts of demethylase.

In accordance with the present invention there is provided the use of the expression of demethylase cDNAs for the production of protein in vertebrate, insect or bacterial or plant cells, such as antibodies against demethylase.

In accordance with the present invention there is provided the use of the sequence of demethylase cDNAs as a template to design antisense oligonucleotides and ribozymes.

In accordance with the present invention there is provided the use of the predicted peptide sequence of demethylase cDNAs to produce polyclonal or monoclonal antibodies against demethylase.

In accordance with the present invention there is provided the use of expression of cDNAs in two hybrid systems in yeast to identify proteins interacting with demethylase for diagnostic and therapeutic purposes.

In accordance with the present invention there is provided the use of expression of cDNAs in bacterial, vertebrate or insect cells to produce large amounts of demethylase for obtaining a x-ray crystal structure and for high throughput screening of demethylase inhibitors for therapeutics and biotechnology.

In accordance with the present invention there is provided a volatile assay for high throughput screening of demethylase inhibitors as therapeutics and anticancer agents which comprises the steps of:

a) using transcribed and translated demethylase cDNAs in vitro to convert methyl-cytosine present in methylated DNA samples to cytosine present in DNA and volatilize methyl group;

b) determining the absence or minute amount of volatilize methyl group as an indication of an active demethylase inhibitor.

In accordance with the present invention there is provided a volatile assay for the diagnostics of cancer in a patient sample which comprises the steps of:

a) determining demethylase activity in patient samples by assaying conversion of methyl-cytosine present in methylated DNA to cytosine present in DNA and its volatilization as methyl groups released as methanol;

b) determining the presence or minute amount of volatilized methyl released as methanol groups as an indication of cancer in the patient sample.

In accordance with the present invention there is provided the use of an antagonist or inhibitor of DNA demethylase for the manufacture of a medicament for cancer treatment, for restoring an aberrant methylation pattern in a patient DNA, or for changing a methylation pattern in a patient DNA.

Such an antagonist is a double stranded oligonucleotide that inhibits demethylase at a Ki of 50 nM, such as

(C$^m$GC$^m$GC$^m$G)

(G$^m$CG$^m$CG$^m$CG$^m$C)n.

The inhibitors include, without limitation an anti-DNA demethylase antibody, an antisense of DNA demethylase or a small molecule such as any derivative of imidazole.

The change of the methylation pattern may activate a silent gene. Such an activation of a silent gene permits the correction of genetic defect such as found for β-thalassemia or sickle cell anemia.

The DNA demethylase of the present invention may be used to remove methyl groups on DNA in vitro such as needed for cloning DNA.

The DNA demethylase of the present invention or its cDNAs may be used, for changing the state of differentiation of a cell to allow gene therapy, stem cell selection or cell cloning.

The DNA demethylase of the present invention or its cDNAs may be used, for inhibiting methylation in cancer cells using vector mediated gene therapy.

In accordance with the present invention there is provided an assay for the diagnostic of cancer in a patient, which comprises determining the level of expression of DNA demethylase by either RT-PCT, ELISA or volatilization assay of the present invention in a sample from the patient, wherein overexpression of the DNA demethylase is indicative of cancer cells.

BRIEF DESCRIPTION OF THE DRAWINGS

FIGS. 1A to 1B illustrate the purification of demethylase (DNA dMTase) from human A549 cells;

FIGS. 3A to 3C illustrate the product of DNA dMTase activity is cytosine and it exhibits no exonuclease or glycosylase activity;

FIGS. 4A–4C illustrate the demethylation reaction releases methanol as a volatile residue;

FIGS. 4E–4F illustrate that the volatile product is methanol;

FIGS. 6A–6D illustrate the substrate Specificity of DNA dMTase;

FIGS. 7A–7D illustrate chromatographic isolation of dMTase from human A549 cells;

FIGS. 8A–8B illustrate the alignment between the methylated DNA binding (MDB) domain of methyl CpG binding protein 2 (MeCP2) and demethylase and the predicted amino acid sequence of human demethylase;

FIG. 8C illustrates the mRNA encoded by demethylase;

FIGS. 9A–9F illustrate the cDNA and their predicted amino acid of demethylases and homologues of the present invention (SEQ ID NOS:1–8);

FIG. 10C illustrates that in vitro translated DNA dMTase releases volatile methyl residues from methylated DNA;

FIG. 10D illustrates that in vitro translated DNA dMTase transform methylated cytosines to cytosines;

FIG. 11B illustrates the polypeptide expressed from transiently transfected demethylase;

FIGS. 11C–11E illustrate that transiently transfected demethylase transforms methylated cytosines to cytosines in a protein dependent manner;

FIG. 12B illustrates that the cloned demethylase releases methanol from methylated DNA;

FIGS. 13A–13C illustrate that the cancer cells express demethylase activity whereas normal cells do not;

FIG. 13D illustrates that demethylase mRNA is highly express in cancer cells;

FIG. 15 illustrates reduced colony formation of HEK 293 cells in cell culture by induced expression of demethylase antisense vector;

FIG. 17 illustrates a model for the inhibition of cancer growth by an inhibition of demethylase.

DETAILED DESCRIPTION OF THE INVENTION

The pattern of methylation is fashioned during development by a sequence of methylation and demethylatiam events. The identity of the demethylase has remained a mystery and alternative biochemical activities have been shown to demethylate DNA but no activity that can truly remove methyl groups from DNA has been shown to date. Utilizing human lung carcinoma cells as a source for demethylase activity we demonstrate that mammalian cells bear a bona fide DNA demethylase (DNA dMTase) activity. DNA dMTase transforms methyl-C to C by catalyzing replacement of the methyl group on the 5 position of C with a hydrogen derived from water. DNA dMTase demethylates both fully methylated and hemimethylated DNA, shows dinucleotide specificity and can demethylate mdCpdG sites in different sequence contexts. This enzyme is different from previously described demethylation activities: it is proteinase sensitive, activated by RNase and releases different products.

DNA dMTase is a novel enzyme showing a new and unexpected activity that has not been previously described in any organism. The finding of a bona fide demethylase, points out new directions in our understanding of the biological role of DNA methylation.

In spite of the fact that it was previously shown that Ras expression in p19 cells can induce demethylation activity. It was not clear whether this demethylation activity is indeed a bona fide demethylase. One would predict that demethylase is present in embryonal cells. It was surprising to see that demethylation activity is present in cancer cells. The finding of high levels of demethylase in A549 cells is indeed an unexpected discovery.

Figure 4D:
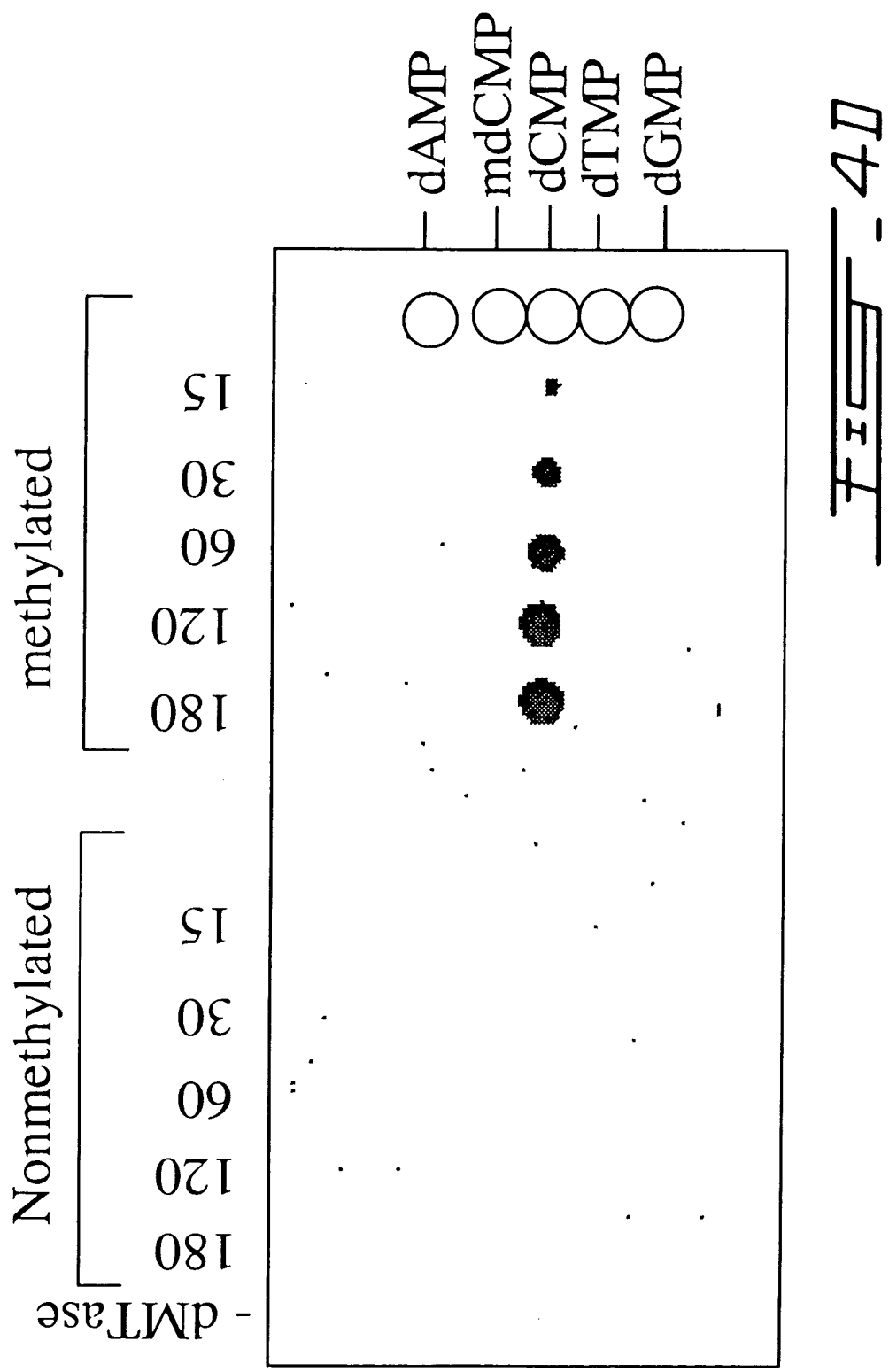
FIG. 4D illustrates the transfer of a proton from water to regenerate cytosine.
Figure 4E:
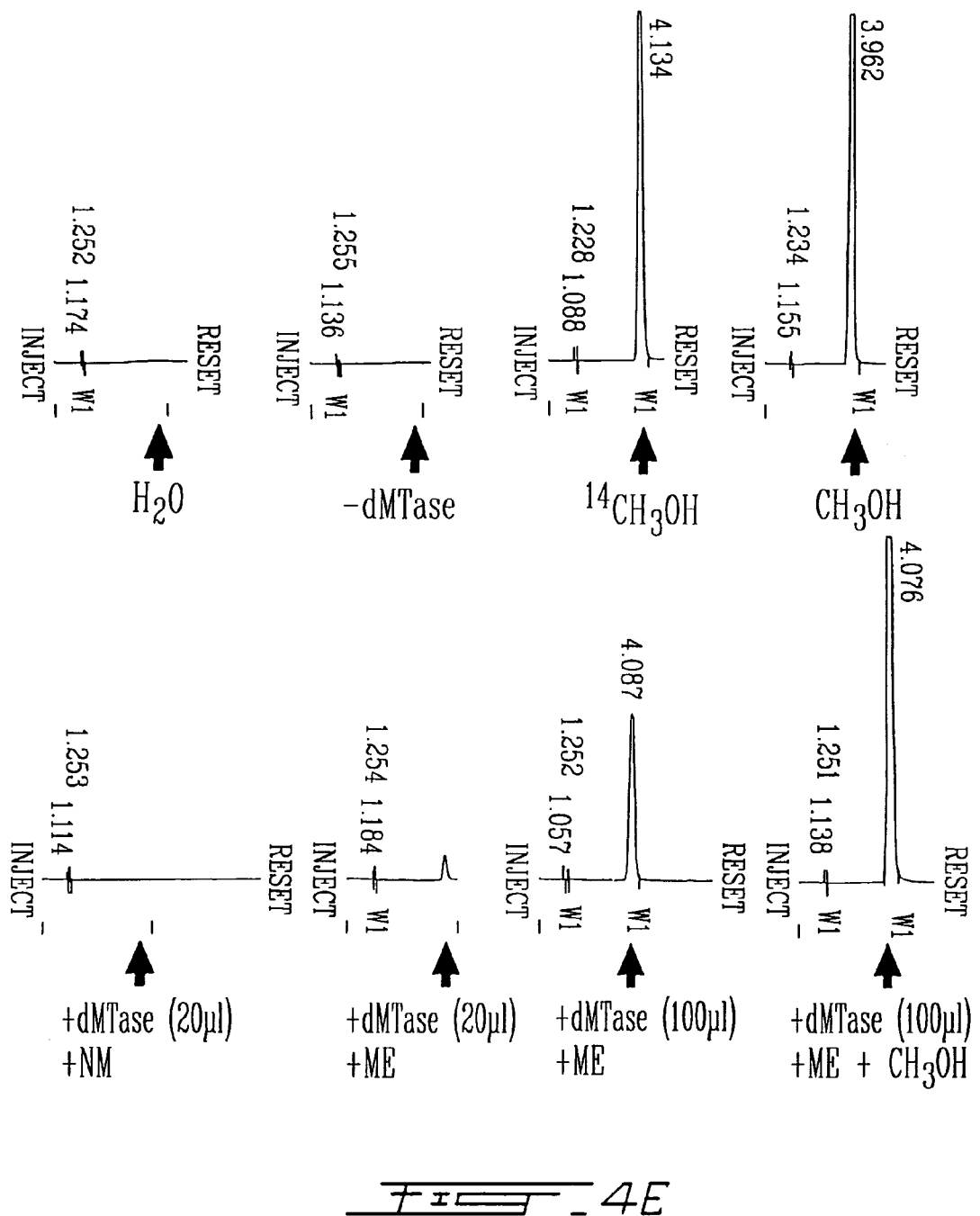

In accordance with the present invention, it is shown and demonstrated that demethylation occurs by removal of a methyl group from methylated cytosine in DNA, that a hydrogen from water replaces the methyl group at the 5' position, that the resulting methyl group reacts with the remaining hydroxyl from water to generate methanol which volatilizes (FIGS. 4E–F). Thus, bona fide demethylation of DNA involves the following reaction:

The cDNA cloned in accordance with the present invention is the demethylase since it can convert methyl-cytosines in DNA to cytosines and volatilize the methyl groups on DNA when transcribed and translated in vitro which are released as methanol. This is a novel cDNA encoding a biochemical activity that has been not described before.

In accordance with the present invention, there is shown a model for the inhibition of cancer growth by an inhibition of demethylase (FIG. 17).

Experimental Procedures

Cell Culture

A549 Lung Carcinoma cells (ATCC: CCL 185) were grown in Dulbecco's modified Eagle's medium (with low glucose) supplemented with 10% fetal calf serum, 2 mM glutamine, 10 U/ml cifrofloxacin. Human Skin Fibroblasts #72–213A MRHF were obtained from BioWhittaker, Bethesda and were grown in Dulbecco's modified Eagle's medium supplement with 2% fetal calf serum, 2 mM glutamine. H446 Lung carcinoma cells (ATCC: HTB 171) was grown in RPMI 1640 medium with 5% fetal calf serum.

Preparation of Nuclear Extract

Nuclear extracts were prepared from A549 cultures at near confluence as previously described (Szyf et al., 1991; Szyf et al., 1995). The cells were trypsinized, collected and washed with phosphate-buffered saline and suspended in buffer A (10 mM Tris, pH 8.0, 1.5 mM $MgCl_2$, 5 mM KCl, 0.5% NP-40) at the concentration of $10^8$ cells per ml for 10 min. at 4° C. Nuclei were collected by centrifugation of the suspension at 1000 g for 10 minutes. The nuclear pellet was resuspended in buffer A (400 μl) and collected as described in the experimental procedures. A nuclear extract was prepared from the pelleted nuclei by suspending them in buffer B (20 mM Tris, pH 8.0, 25% glycerol, 0.2 mM EDTA and 0.4 mM NaCl) at the concentration of $3.3 \times 10^8$ nuclei per ml and incubating the suspension for 15 min. at 4° C. The nuclear extract was separated from the nuclear pellet by centrifugation at 10,000 g for 30 minutes. Nuclear extract were stored in –80° C. for at least two months without loss of activity.

Chromatography on DEAE-Sephadex

A freshly prepared nuclear extract (1 ml, 1.1 mg) was passed through a Microcon™ 100 spin column, the retainant was diluted to a conductivity equivalent to 0.2 M NaCl in buffer L and applied onto a DEAE-Sephadex column (Pharmacia) (1.0×5 cm) that was preequilibrated with buffer L (10 mM Tris-HCl, pH 7.5, 10 mM $MgCl_2$) containing 0.2 M NaCl at a flow rate of 1 ml/min. The column was then washed with 15 ml of the starting buffer (buffer L+0.2 M NaCl) and proteins were eluted with 5 ml of a linear gradient of NaCl (0.2–5.0 M). 0.8 ml fractions were collected and assayed for demethylase activity after desalting through a Microcon™ 10 spin column (Amicon) and resuspension of the retainant in 0.8 ml buffer L. DNA demethylase eluted between 2–5.0 M NaCl.

Chromatography on S-Sepharose

Active DEAE-Sepharose column fractions were pooled, adjusted to 0.1 M NaCl by dilution and loaded onto an S-sepharose column (Pharmacia) (1.0×5 cm) which had been preequilibrated with buffer L containing 0.2 M NaCl at a flow rate of 1 ml/min. Following washing of the column as described in experimental procedures, the proteins were eluted with 5 ml of a linear NaCl gradient (0.2–5.0M). 0.5 ml fractions were collected and assayed for DNA demethylase activity after desalting and concentrating to 0.2 ml using a Microcon™ 10 spin column. DNA demethylase activity eluted around 5.0 M NaCl.

Chromatography on Q-Sepharose

Active fractions from S-sepharose column were pooled, adjusted to 0.2 M NaCl by dilution and applied onto a Q-sepharose (Pharmacia) column (1.0×5 cm) which had been equilibrated as described in the experimental procedures at a flow rate of 1 ml/min. The column was washed and the proteins were eluted with a linear NaCl gradient (0.2–5.0 M). Fractions (0.5 ml) were collected, assayed for demethylase activity after desalting and concentrating to a final volume of 0.2 ml as described in the experimental procedures. The demethylase activity eluted around 4.8–5.0 M NaCl.

Gel-Exclusion Chromatography on DEAE-Sephacel

The pooled fractions of Q-sepharose column were adjusted to 0.2 M NaCl, loaded onto a 2.0×2.0 cm DEAE-Sephacel column (Pharmacia) and eluted with 10 ml of buffer L containing 0.2 M NaCl. The fractions (0.8 ml) were collected and assayed after concentration to about 180 μl with a Microcon™ 10 spin column for DNA demethylase activity. The activity was detected at fraction 4, which is very near the void volume (~200 kDa).

Assay of DNA Demethylase Activity

To directly assay DNA demethylase activity in vitro two independent methods were applied.

(A) To assay the conversion of methyl-dCMP (mdCMP) to dCMP we used a previously described method (Szyf et al., 1995). Briefly, $\alpha^{32}P$ labeled, fully methylated poly [$mdC^{32}PdG$]n substrate was prepared as follows. One hundred ng of a double-stranded fully methylated (mdCpdG) oligomer (Pharmacia) were denatured by boiling, which was followed by partial annealing at room temperature. The complementary strand was extended with Klenow fragment (Boehringer Mannheim) using methyl-5-dCTP (mdCTP, 0.1 mM) (Boehringer Mannheim) and [$\alpha$-$^{32}P$] GTP (100 μCi, 3000 Ci/mmol), and the unincorporated nucleotides were removed by chromatography through a NAP-5 column (Pharmacia). The NAP-5 chromatography was repeated to exclude minor contamination with unincorporated nucleotides. As a control a non-methylated poly[$dC^{32}pdG$]n substrate was similarly prepared except that a nonmethylated dCpdG oligomer served as a template and dCTP was used in the extension reaction. The column fractions (30 μl), described in the experimental procedures were incubated with 1 ng of poly[$mdC^{32}pdG$]n substrate for 1 hour at 37° C. in a buffer L containing 25% glycerol (v/v) and 5 mM EDTA. The reacted DNA as well as a non-methylated poly[$dC^{32}pdG$]n and methylated [$mdC^{32}pdG$]n nonreacted controls were purified by phenol/chloroform extraction and subjected to micrococcal nuclease digestion (100 μg at 10 μl) and calf spleen phosphodiesterase (2 μg) (Boehringer) (Pharmacia) to 3' mononucleotides for 15 hours at 37° C. The digestion products were loaded onto a thin layer chromatography plate (TLC) (Kodak, 13255 Cellulose), separated in a medium containing, 132 ml Isobutyric acid:40 ml water:4 ml ammonia solution, autoradiographed and the intensity of the different spots was determined using a phosphorimager (Fuji, BAS 2000). $^{32}P$ labeled substrates and tritium labeled substrates were phosphoimaged using BAS 2000 plate and BAS-TR2040 phosphorimager plate respectively.

(B) The second method determined removal of methylated residues from methylated DNA by measuring disappearance of $^3H$—$CH_3$ or $^{14}C$—$CH_3$ from the reaction mixture. 100 ng of poly [dCdG]n double stranded DNA was methylated using SssI methylase (New England Biolabs) and an excess of [$^3H$-methyl AdoMet (80 Ci/mmol; New England Nuclear)]. The tritiated methyl group containing DNA was purified from labeled AdoMet using NAP-5 column chromatography. All column purified fractions of DNA demethylase were assayed using the tritiated substrate. In a typical assay, 1 ng of DNA was incubated (at a specific activity of $4 \times 10^6$ dpm/mg) with 30 μl of column fraction for one hour at 37° C. in buffer L. To determine the number of methyl groups remaining in the DNA following incubation with the different fractions, 250 μl of water were added and the mixture was incubated at 65° C. for 5 minutes. One hundred μl of the reaction mixture were withdrawn for liquid scintillation counting. Controls received similar treatment except that in place of a column fraction, an equal volume of buffer L was added. The number of methyl groups that were removed from the DNA by the different fractions was determined by subtracting the remaining counts in each of the fractions from the counts remaining in the control. All tests were carried out in triplicates. The results are presented as picomole methyl group removed. One unit of DNA dMTase activity is defined as: amount of enzyme that releases one picomole of methyl group from methylated dCpdG substrate in one hour at 37° C.

Methyl Removal Assay Using Double-Labeled Substrates

To determine whether the methyl group leaves the DNA and not any non-specific removal of tritium, we prepared SK plasmid DNA containing a tritiated hydrogen at the 6' position of cytosine and thymidine by growing the plasmid harboring bacteria in the presence of deoxy [6-$^3$H] Uridine (22 Ci/mmol; Amersham) (10 µCi/ml). The [6-$^3$H]-cytosine containing pBluescript SK(+) was purified according to standard protocols and was methylated sing an excess of [$^{14}$C-methyl] AdoMet (59 mCi/mmol; mersham) (10 µCi per 100 µl reaction) and SssI methylase. The double labeled DNA substrate was purified twice on a NAP-5 column. 15 µl of DNA dMTase were incubated with 1 ng of double labeled DNA (specific activity of 2000 dpm/ng) for 1 hour at 37° C. Following incubation, the remaining $^{14}$C versus $^3$H counts were determined as described in the experimental procedures by scintillation counting (Wallac). The $^{14}$C counts were normalized against $^3$H counts. The controls received similar treatment except that instead of DNA dMTase, an equal amount of distilled water was added to them.

To determine the number of $^3$H—CH$_3$ in the gaseous phase, 1 ng of $^3$H—CH$_3$ poly [dCpdG] DNA were incubated with DNA dMTase overnight in a sealed tube (Pierce, Ill., USA). 0.8 ml of air were removed from the tube using a gas tight syringe (Hamilton, Reno, Nev.) and injected into a sealed gas tight scintillation vial containing 10 ml OptiPhase scintillation fluid (Wallac, UK) and counted. As a control the DNA was incubated with an equal volume of buffer L and treated similarly.

Synthesis of Other Methylated dC Dinucleotides

Poly [mdC$^{32}$pdA] and [mdc$^{32}$pdT] substrates were prepared as follows. About 0.5 µg of 20 mer oligonucleotides 5' (GG)103', 5' (GT)103' and 5' (GA)103' were boiled and annealed at room temperature with oligonucleotide 5' CCCCCC3', 5' CACACA3' and 5' CTCTCT3' respectively. The complementary strand was extended with Klenow fragment using m5dCTP (Boehringer Mannheim) and either [α$^{32}$P] dATP (100 µCi, 3000 Ci/mmol) or [α$^{32}$P] dTTP (100 µCi, 3000 Ci/mmol) respectively. The unincorporated nucleotides were removed by chromatography through a NAP-5 column. Hemimethylated mdCpG substrate was prepared in a similar manner except that a non-methylated poly dCpdG substrate (Boehringer) was used as template and m5dCTP and [α$^{32}$P]dGTP were used for extension as described in the experimental procedures.

Assay for Nuclease and Glycosylase Activity

[$^{32}$ pmdCpdG]n substrate which included a labeled $^{32}$P 5' to mdC was prepared as follows. About 100 ng of poly dCpdG DNA were boiled and partially annealed at room temperature. [α$^{32}$P]dCTP and cold dGTP were used for complementary strand extension as described in the experimental procedures. The free nucleotides were separated using NAP-5 column chromatography. The purified [$^{32}$ pmdCpdG]n DNA was subjected to methylation by SssI methylase using 320 µM AdoMet. The DNA was repurified twice using a NAP-5 column. The methylated DNA (1 ng) was incubated with either 30 µl DNA dMTase, nuclear extract or buffer L. To determine whether α$^{32}$P labeled residue is excised from the DNA it was directly applied (3 µl) onto a TLC plate. To determine whether the DNA was demethylated it was subjected to digestion with snake venom phosphodiesterase (0.2 mg in a 10 µl reaction volume) (Boehringer Mannheim) which attacks the 3'-OH group releasing 5'-mononucleotides. The resulting mononucleotides were separated on TLC plates and autoradiographed.

To test whether dCTP copurifies with DNA dMTase, which may be involved in activities other than bona fide demethylation, 20 µM of dCTP with 1 µl of α$^{32}$P labeled dCTP (3000 Ci/mmole) was loaded onto the column with nuclear extract. The $^{32}$P counts were measured in the flow through, washes and in the different fractions. About 1.1 million counts were loaded onto the DEAE-Sepharose column and were all recovered up to fraction 8.

To determine whether DNA dMTase contains a DNA polymerase activity, DNA demethylase reactions were performed in presence of 500 µM of ddCTP (Pharmacia) or 500 µM of m5dCTP (Boehringer Mannheim) at initial rate conditions.

To determine whether DNA dMTase is sensitive to RNase or Proteinase K treatment, DNA dMTase was pretreated for 1 h at 56° C. with 200 µg/ml proteinase K (Sigma). A demethylation reaction was carried out with this pretreated fraction in the usual manner using both demethylation assays described in the experimental procedures. To test the effect of RNA digestion on the demethylation reaction, the fractions from different columns were treated with 100 µg/ml RNase A (Sigma).

Demethylation of pBluescript SK(+) Plasmid

About 4 µg plasmid pBluescript SK (Stratagene) was subjected to methylation using SssI methylase. The methylated plasmid (4 ng) was incubated with 30 µl of DNA dMTase Fraction 4 of DEAE-Sephacel column under standard conditions, extracted with phenol: chloroform and precipitated with ethanol. About 1 ng of the plasmid were subjected to digestion with 10 units each of either of the restriction endonucleases EcoRII (GIBCO-BRL), DpnI, HhaI or HpaII (New England Biolabs) before and after methylation as well as after DNA dMTase treatment in a reaction volume of 10 µl for 2 hour at 37° C. Following restriction digestion the plasmids were extracted with phenol:chloroform, ethanol precipitated and resuspended in 10 µl. The plasmids were electrophoresed on a 0.8% (w/w) Agarose gel, transferred onto a Hybond Nylon membrane and hybridized with pBluescript SK(+) plasmid which was $^{32}$P labeled by random-priming (Boehringer Mannheim).

Effect of Redox Reagents (NAD, NADH, NADP, NADPH and FeCl$_3$) on Demethylase Activity The reagents were prepared at 100 µM concentration and added at a final concentration of 10 µM to a standard methyl removal assay under initial rate conditions as described in the experimental procedures. The methyl removal activity in presence of each of the cofactors was compared to a control DNA dMTase reaction.

Determination of Kinetic Parameters

For determination of kinetic parameters, the demethylation reactions were performed using both assays (generation of dCMP and removal of methyl) as described in the experimental procedures except that varying DNA concentrations from 0.1 nM to 2.5 nM were used in a total volume of 50 µl including 30 µl of DNA dMTase. Since it has been established by previous experiments that the reaction proceeds for at least 3 hours, the initial velocity of reaction was measured at one hour intervals. The velocity data was collected at each substrate DNA concentration range stated for both assays. The Km and Vmax values for DNA demethylase activity were determined from double reciprocal plots of velocity versus substrate concentration.

Measurements of Methanol Production Catalyzed by Demethylase by Gas Chromatography Gas chromatography was performed with a Varian™ model 3400 GC equipped with a 30 m Stabilwax™ column (0.053 cm i.d.: Restek Corporation). Nitrogen™ was used as carrier gas at a flow rate of 32 ml/min, the injector and detector chambers were at 200 and 300° C. respectively. The column was maintained at 40° C. for 5 minutes after sample injection.

The demethylase reaction was performed in eppendorf tubes kept within sealed scintillation vials with 300 µl of water as aqueous phase (in radioactive trapping experiments this was replaced by 300 µl of methanol). The demethylase reaction was initiated in buffer L (10 mM $MgCl_2$, 10 mM Tris-HCl pH 8.0) with 500 ng of tritiated SK plasmid (6000 dpm/µl) and 100 µl of demethylase at 37° C. After overnight incubation at 37° C., the aqueous phase surrounding the eppendorf tube was transferred to a fresh eppendorf tube, 2 µl of this mixture was injected in the gas chromatography using a gas tight syringe (Hamilton, Reno, Nev.).

Coupled In Vitro Transcription Translation

The mRNAs encoded by the pcDNA 3.1/His Xpress demethylase constructs described above were transcribed and translated by coupled transcription-translation using Promega™ TNT reticulocyte lysate kit (according to manufacturer's protocol), 2 µg of each construct and 40 µCi of [$^{35}$-S]methionine (1,000 Ci/mmol, Amersham) in a 50 µl reaction volume. To purify non labeled in vitro translated demethylase, coupled in vitro transcription and translation was performed as above but in the presence of cold methionine. The translation products were bound to a Probond™ nickel column (Invitrogen) and demethylase was eluted according to the manufacturer's protocol with increasing concentrations of imidazole. Demethylase is eluted at 350–500 mM imidazole. The imidazole eluted demethylase was dialyzed and concentrated by lyophilization.

Gas Chromatography Coupled with Mass Spectrometry (GC-MS) Analyses for Identification of Volatile Product of Demethylase Catalyzed Reaction as Methanol The demethylation reactions (volume 50 l) were run in conical vials having a total internal volume of 350 microlitres. The vials were closed with a teflon-lined screw cap and left at room temperature for 18 h. The vials were cooled in an ice bath, opened and 10 mg of NaCl and 50 microlitres of toluene were added. The vials were frequently shaken over a period of 1 h. The toluene phases were pipetted into clean vials in a manner to rigorously exclude water carry over. Anhydrous sodium sulfate (5 mg) was added to the toluene extracts to remove water, and the toluene phases were pipetted into autoinjector vials for GC/MS analysis. Aliquots of 3 microlitres were analyzed under the following instrumental conditions: Instrument: Hewlett-Packard 5988A; Column: 30 m×0.25 mm i.d. fused quartz capillary with 0.25 micron DB-1 liquid phase, programmed after an initial hold for 1 min at 70 deg at 5 deg/min to 80 deg, then ramped ballistically to 280 deg for bake-out for 5 min; Injector and interface temperatures: 250 deg; Helium flow rate 1.5 ml/min; Mass spectrometer: ion source 200 deg, 70 eV electron impact ionization, scanning from m/z 10 to 50 in full scan mode was begun 6 s after injection, and ceased at 1.5 min to avoid acquisition of the intense toluene solvent peak.

Human A549 Cells Bear a Demethylase Activity that Could be Purified Away from dCTP and DNA MeTase The use of an appropriate cellular source and a direct assay for demethylase activity are obviously critical. As we have previously shown that demethylase activity was induced in response to ectopic expression of the Ras oncogene (Szyf et al., 1995) we reasoned that cancer cells might bear high levels of demethylase activity. Based on preliminary studies demonstrating the presence of high levels of demethylase activity in the human lung carcinoma cell line A549, we have chosen this cell line for our further studies and purification steps. Previous studies have used indirect measures such as increased sensitivity to methylation-sensitive restriction enzymes as indicators of demethylase activity (Weiss et al., 1996; Jost et al., 1995). To directly measure the conversion of 5-mdCMP in DNA to dCMP, we have utilized a completely methylated $^{32}$P labeled [mdC$^{32}$pdG]n double stranded oligomer which we had previously described (Szyf et al., 1995). Following incubation with the different fractions, the DNA is purified and subjected to cleavage with micrococal nuclease to 3' mononucleotides. The 3' labeled mdCMP and dCMP are separated by thin layer chromatography (TLC) and the conversion of mdCMP to dCMP is directly determined. This assay provides a stringent test for bona fide demethylation and discriminates it from previously described 5mCpC replacement activities (Jost et al., 1995; Weiss et al., 1996). The glycosylase-demethylase activity described by Jost et al. (Jost et al., 1995) will require the presence of a ligase activity and an energy source for replacement of mdC with C to be detected by our assay, whereas the demethylase activity described by Weiss et al. will not be detected since it replaces the intact mdC$^{32}$pdG dinucleotide with a cold dCpdG without altering its state of methylation (Weiss et al., 1996).

Figure 1A:
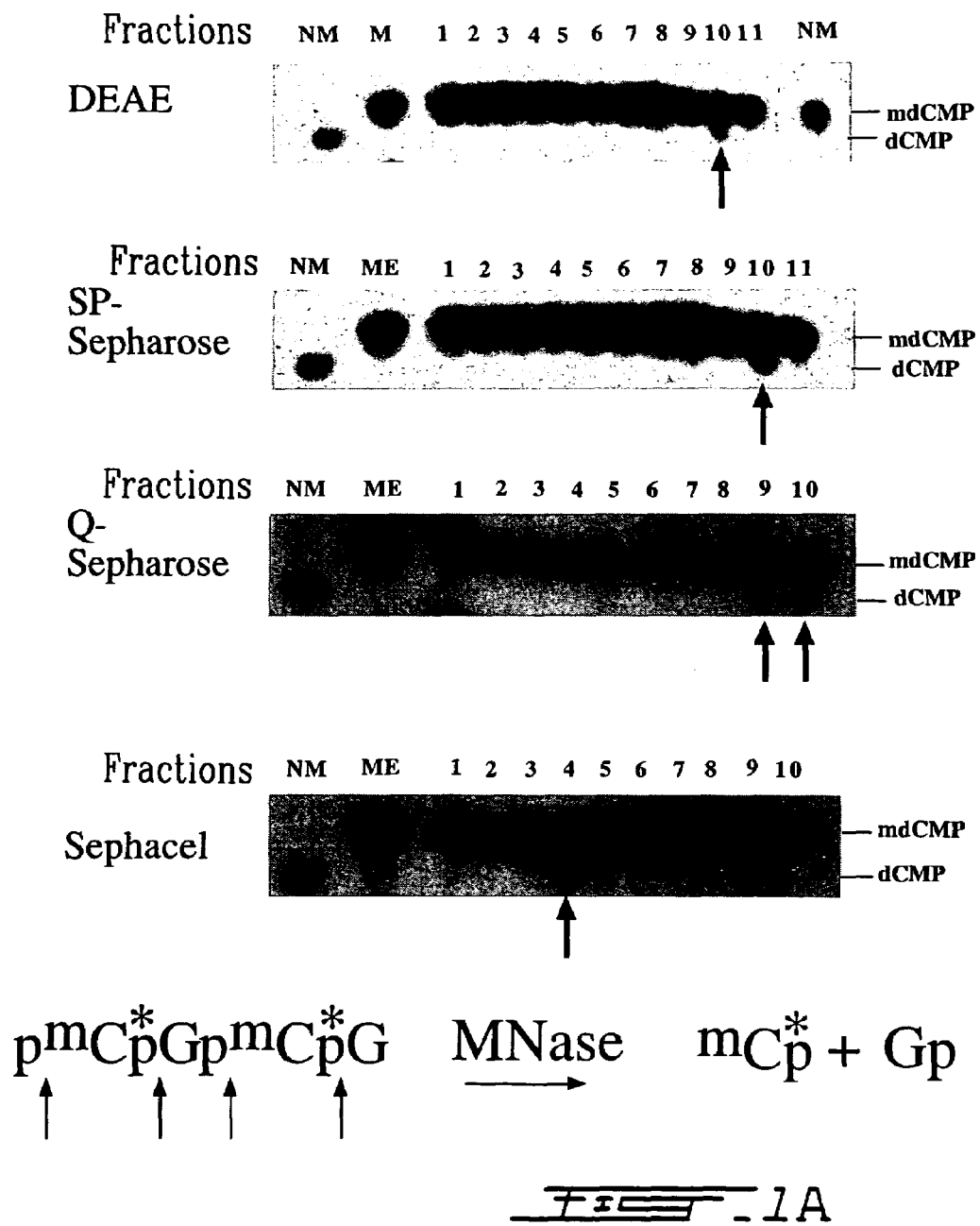

Nuclear extracts were prepared from A549 cells, applied onto a DEAE-Sephadex column, eluted with a linear gradient from 0.2–5.0M NaCl and the fractions were assayed for demethylase (dMTase) activity as described in the experimental procedures. As shown in FIG. 1(A) a clear peak of dMTase activity is eluted at the high salt fraction 10.

Conversion of methylated cytosine to cytosine: Nuclear extracts prepared from A549 cells (1.1 mg) were passed through an AMICON™ 100 spin column. The retainant (98.56 mg, 0.2 mg/ml) was loaded onto a DEAE-Sepharose column, the different chromatographic column fractions eluted by a linear NaCl gradient (0.2–5M) were desalted and (30 µl) incubated with 1 ng of [mdC$^{32}$pdG]n double stranded oligomer for 1 hour at 37° C., digested to 3' mononucleotides and analyzed on TLC as described in the experimental procedures. Control methylated (ME) and nonmethylated (NM) [dC$^{32}$pdG]n substrates were digested to 3' mononucleotides and loaded on the TLC plate to indicate the expected position of dCMP and mdCMP. The active fraction is indicated by an arrow. This fraction was loaded on S-Sepharose followed by Q-Sepharose and DEAE-Sephacel fractionation.

The first chromatography step purified the dMTase activity from the bulk of nuclear protein (FIG. 1B) and is a very effective purification step.

DNA dMTase activity as measured by the release of volatile methyl residues. The different column fractions were incubated with 1 ng (4×10$^6$ dpm/µg) of [$^3$H]—CH$_3$-[mdCpdG]n oligomer and the release of volatile methyl residues was determined (−) and presented as total dpn). The results are an average of three independent determinations. Protein concentration was determined using the Bio-Rad Bradford kit (−). The elution profile of 20 µM of [$^{32}$P]-α- dCTP incubated with the protein was determined by scintillation counting of the different DEAE fractions (−) and presented as fraction of dCTP loaded on the column.

To exclude the possibility that the DNA dMTase activity detected in our assay is carried by the DNA MeTase, we assayed the fractions for DNA MeTase activity using a hemimethylated DNA substrate as previously described (Szyf et al., 1991). As observed in FIG. 1B DNA MeTase activity is detected in the second and third fractions, thus our fractionation separated DNA dMTase away from the DNA MeTase suggesting that they are independent proteins.

There is a remote possibility that the demethylation observed is not a bona fide demethylation but a consequence of a glycosylase removal of mC, followed by removal of the remaining deoxyribose-phosphate by AP (apyrimidine) nuclease, repair of the gap catalyzed by DNA polymerase using trace dCTP contained in the fraction and ligation of the break with ligase in the presence of residual ATP. For this hypothesis to be consistent with our data, four independent enzymes and two cofactors have to cofractionate with DNA dMTase. To exclude the possibility that a trace amount of dCTP is bound to DNA dMTase active fraction, we have added 20 µM of $^{32}$P labeled dCTP (10×10$^6$ cpm) to the nuclear extract and determined its elution profile on the DEAE column. Less than background cpm (10 cpm) were detected in the DNA dMTase active fraction suggesting that our first column purifies dCTP away from the DNA dMTase at least 1×10$^6$ fold (FIG. 1B). If any dCTP is present in the nuclear extract, the remaining concentration after fractionation on DEAE is well below the Kms of the known DNA polymerases. The possibility that dCTP is so tightly bound to the enzyme that it could not be replaced by the exogenous $^{32}$P labeled dCTP is very remote since an enzyme using dCTP as substrate must readily exchange dCTP.

The active fraction 10 was further fractionated sequentially on the following columns: S-Sepharose and Q-Sepharose. The DNA dMTase eluted at the high salt fraction from both columns as determined by the [mdC$^{32}$pdG]n demethylation assay (FIG. 1A). The ion exchange chromatography was followed by chromatography on DEAE-Sephacel.

The fact that we have maintained our activity even after 4 fractionation steps (Table 1) and that only a single polypeptide is apparent after the last purification step argues strongly against the possibility that the activity detected in our study is a repair or replacement activity. Any replacement mechanism must involve a number of proteins and additional cofactors and substrates. In summary, the chromatography of the demethylase activity in A459 cells provides strong support to the hypothesis that mammalian cells bear a bona fide demethylase activity.

DNA dMTase Releases a Volatile Derivative

A bona fide demethylation has to result in release of the methyl group as a volatile derivative such as $CO_2$, methanol, methane or formaldehyde. We have therefore incubated a {[$^3$H]-CH$_3$-dCpdG}n double stranded oligonucleotide with the different column fractions and the rate of release of the tritiated methyl from the aqueous phase was determined by scintillation counting of the remaining radioactivity in the reaction mix. As demonstrated in FIG. 1b (diamond), the dMTase active fractions release labeled methyl groups from the methylated substrate.

Figures 2A, 2B:
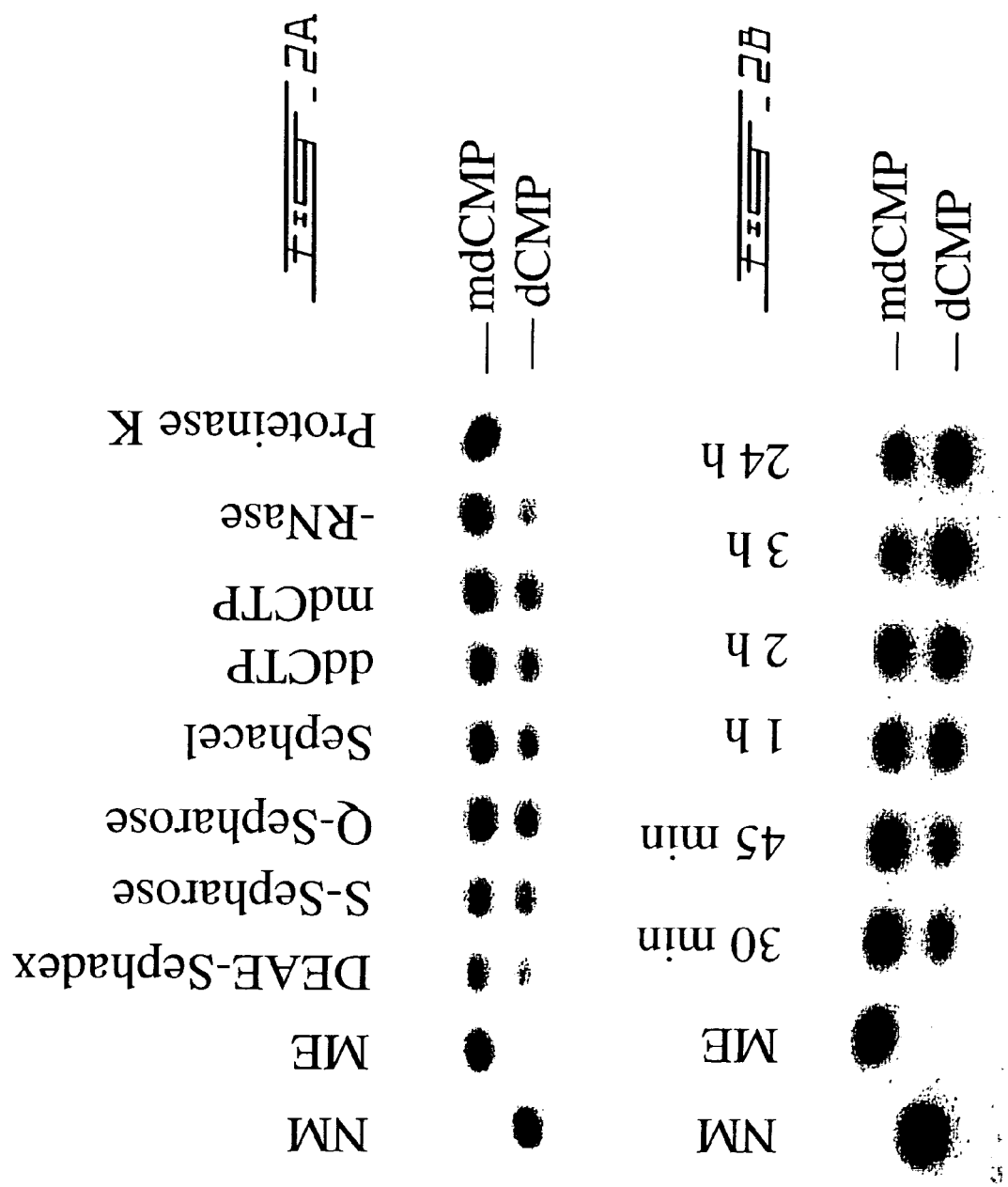
FIGS. 2A and 2C illustrate that DNA dMTase is a protein inhibited by RNA and not by ddCTP, mdCTP.
FIGS. 2B and 2D illustrate the kinetics of DNA dMTase activity.
Figure 2D:
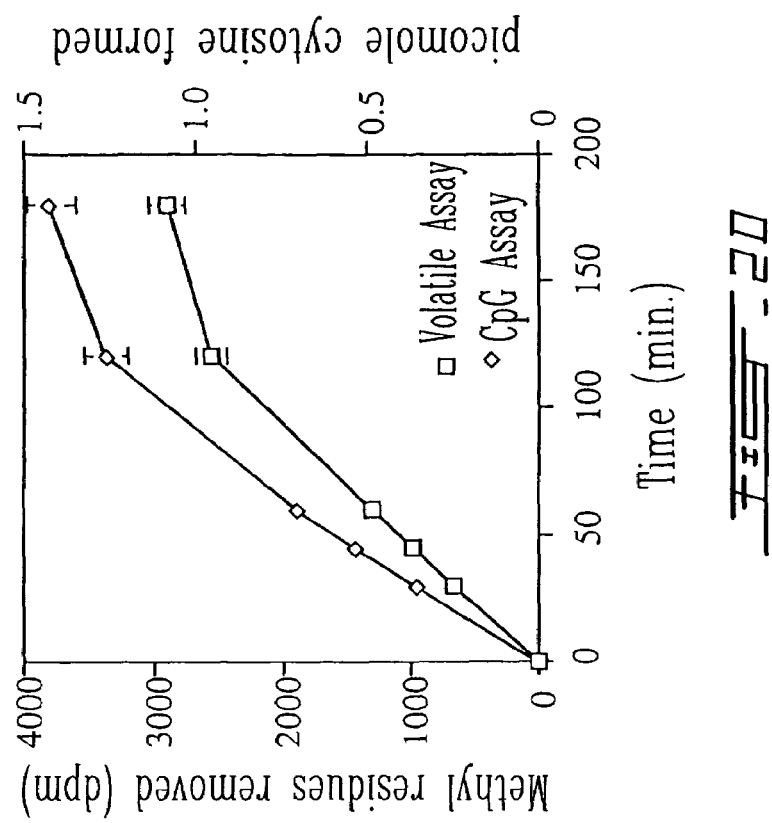
Figure 2C:
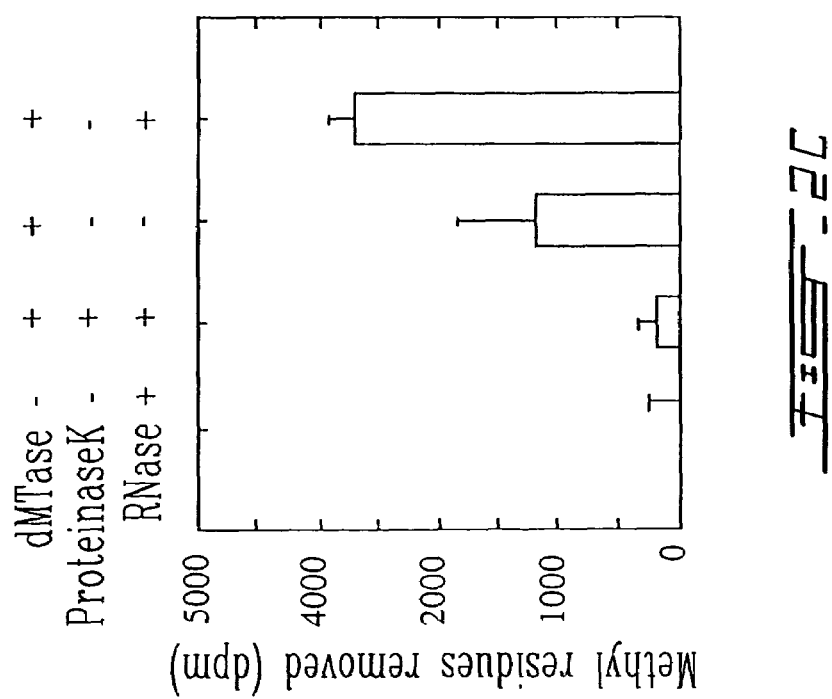

DNA dMTase is a Protein which is Inhibited by RNA, does not Involve an Exchange Activity and does not Require Additional Cofactors DNA dMTase activity measured either as transformation of mdC to C (FIG. 2a) or as release of volatile methyl residues (FIG. 2c) is abolished after proteinase K treatment and is not inhibited but rather enhanced following RNase treatment. 500 µM of ddCTP which inhibits DNA polymerase does not inhibit demethylation of the [mdC32pdG]n substrate, nor is it inhibited by high concentrations of methyl-dCTP (500 µM) (FIG. 2a), which is consistent with the hypothesis that demethylation does not involve an excision and replacement mechanism. If a replacement mechanism is involved in demethylation, the presence of mdCTP should result in incorporation of methylated cytosines and essential inhibition of demethylation. Thus, the DNA dMTase identified here is a protein and not an RNA and is unequivocally different from the previously published RNA based or glycosylase based demethylase activities.

The DNA dMTase reaction proceeds without any requirement for additional substrates such as dCTP, redox factors such as NADH and NADPH or energy sources such as ATP (data not shown). As observed in FIGS. 2b and 2d, the DNA dMTase reaction maintains its initial velocity up to 90 minutes and continues up to 120 minutes. This time course is inconsistent with dependence on enzyme-bound additional nonreplenishable substrates such as dCTP or ATP or a nonreplenishable redox factor such as NADH or NADPH. Exhausting the nonreplenishable substrate or redox factor would have resulted in rapid deceleration of the initial velocity.

A Product of the Demethylation Reaction is Deoxycytosine in DNA

What is the product of the demethylation reaction? The results presented above (FIGS. 1a, 2a and b) based on a one dimension TLC separation show that DNA dMTase generates dC from mdC in DNA. To further substantiate this conclusion, we subjected DNA dMTase treated DNA to remethylation with the CpG MeTase M. Sss I which can transfer a methyl group exclusively to dC. The results presented in FIG. 3a show that the demethylated product of DNA dMTase is dC since it is completely remethylated with M.Sss I. The identity of the demethylated product as dC was further established by a two-dimension TLC analysis demonstrating that the product of dMTase comigrates with a cold dCMP standard in both dimensions (FIG. 3b).

DNA dMTase does not release a nucleotide, a phosphorylated base or phosphate from methylated DNA when incubated with a [32 pmdCpdG]n substrate which included a labeled $^{32}$P 5' to mdC or our standard methylated substrate (FIG. 1) where $^{32}$P is 3' to the m5dC (FIG. 3c). Nuclear extracts which obviously contain a number of glycosylases and nucleases release phosphorylated derivatives in the same assay (FIG. 3c). dMTase transforms the methyl cytosine in the [32 pmdCpdG]n substrate to cytosine as demonstrated when the reacted DNA is digested to 5' mononucleotides (FIG. 3c +V PDS) and analyzed by TLC. Since this reaction does not involve release of a $^{32}$P derivative (FIG. 3c −V PDS), it demonstrates that dMTase transforms methylated cytosines to cytosines on DNA without disrupting the integrity of the DNA substrate by glycosylase or nuclease activity.

The Second Product of the dMTase Reaction is Methanol

What is the identity of the leaving group? The results presented in FIG. 1b suggest that the labeled methyl leaves the DNA as a volatile compound. The demethylase reaction involves release of the methyl group per se whereas the cytosine base ring remains in the aqueous phase. FIG. 4a demonstrates this point by using a methylated plasmid labeled with a $^3$H-hydrogen at the sixth position of cytosine and [14C]-methyl at the fifth position of cytosine as a substrate.

The three most obvious candidates the methyl group is leaving as are formaldehyde, carbon dioxide, and methanol. Methadone trapping for labeled formaldehyde detection and sodium hydroxide trapping for labeled carbon dioxide detection were both negative in identifying the form in which the methyl group is leaving in the dMTase reaction (data not shown). The other possible chemical form that the methyl group may leave the DNA as, is methanol. Since methanol is a volatile compound, a simple method to measure generation of methanol is a scintillation-volatilization assay (see FIG. 4b for description). Volatilization assays have been previously used to measure release of methanol in demethylation reactions. The demethylation reaction mix containing the labeled {[$^3$H]-CH$_3$-dCpdG}n substrate with either dMTase or no enzyme, as a control, is added to an uncapped 0.5 ml tube which is placed in a sealed scintillation vial containing scintillation fluid. Released methanol is volatile, diffuses out of the open reaction tube and is mixed with the excess of the scintillation fluid in the vial registering as counts in the scintillation counter. As a control indicating that methanol is volatilized under the conditions of our assay, we incubated approximately equal counts of radioactively labeled methanol under the same conditions and measured the counts in a scintillation counter at different time points. As observed in FIG. 4c the majority of methanol in the reaction tube volatilizes from the reaction tube into the scintillation fluid following an overnight incubation at 37° C. The experiment shown in FIG. 4b demonstrates that volatilized label is released from methylated DNA only in the presence of dMTase.

The identity of the volatile group has been determined to be methanol by a gas chromatography (GC) analysis. The demethylation and control reactions (indicated in FIG. 4e) were performed in an uncapped tube placed in a sealed scintillation vial containing a larger volume (300 μl) of water. The volatile residue diffuses into the surrounding water and mixes with it. A 2 μl sample of the surrounding water was injected into a GC column as described in the methods. As shown in FIG. 4e, the volatile compound released by dMTase in a dose response manner coelutes with methanol. Release of methanol is observed only in the presence of both dMTase and methylated DNA. No methanol is released when dMTase is reacted with nonmethylated DNA, demonstrating that methanol is a product of demethylation of DNA.

The leaving group was also identified as methanol using gas chromatography coupled with Mass spectrometry (GC-MS). As illustrated in FIG. 4f., incubation of methylated DNA with dMTase (dMTase+ME–DNA) results in release of a peak with the retention time and mass spectrum (peaks are identified at 32 and 29 atomic mass which are the atomic masses of methanol and ionized methanol respectively) which is consistent with its identification as methanol. Incubation of dMTase with nonmethylated DNA does not release methanol indicating that methanol is a product of the demethylation reaction. No methanol is released when the samples are incubated with dMTase treated with protease K indicating that the release of methanol from methylated DNA is catalyzed by an enzymatic activity.

Demethylation Involves Transfer of a Hydrogen from Water to Regenerate Cytosine

Figure 5:
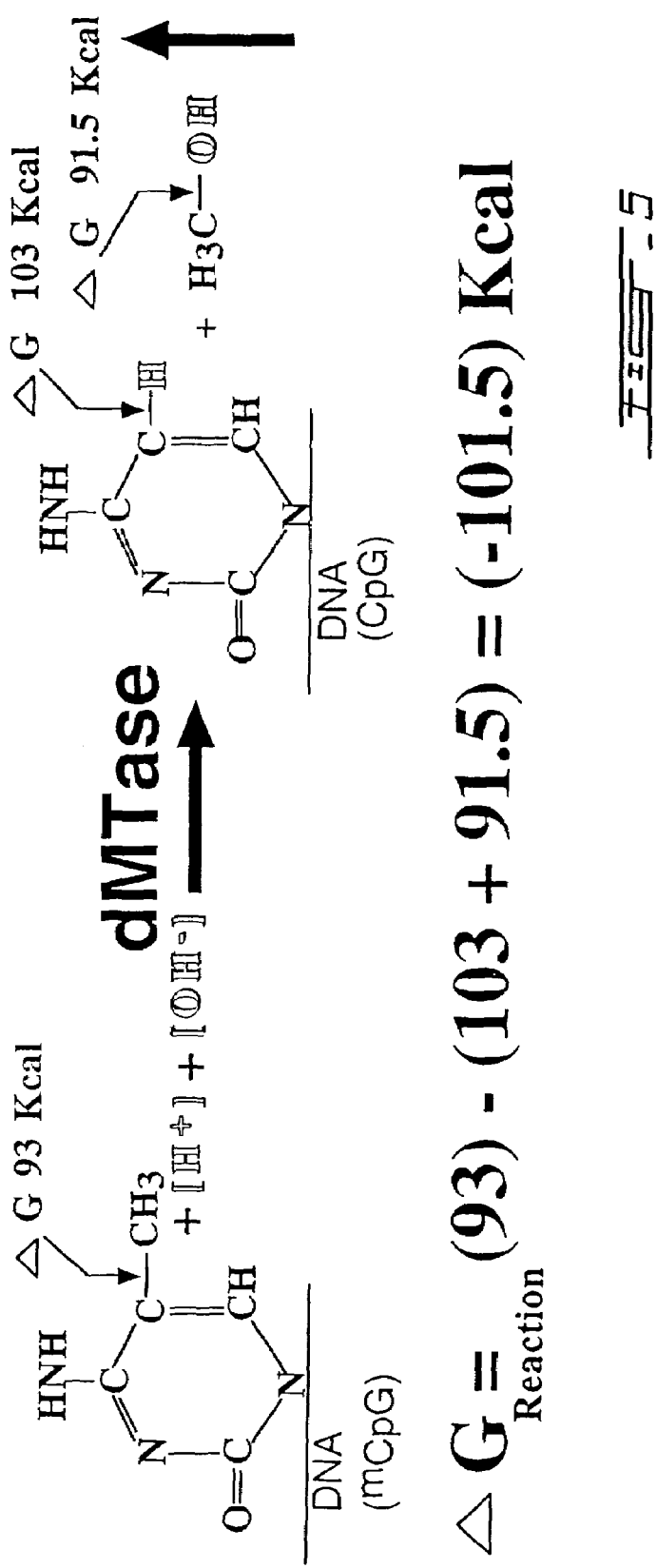
FIG. 5 illustrates the suggested demethylation reaction.

If demethylation involves removal of the methyl moiety from mdC, a hydrogen has to be transferred to the carbon at the 5' position to regenerate cytosine. Since no redox factors are involved, what is the source of the hydrogen? To test the hypothesis that the source of the hydrogen is water, we incubated either non labeled [mdCpdG]n or [dCpdG]n double stranded DNA with DNA dMTase for different time periods in the presence of tritiated water, following which the DNAs were digested to 3' dNMPs, separated on TLC with non-radioactive standards for each of the 5 possible dNMPs and exposed to a tritium sensitive phosphorimaging plate. As seen in FIG. 4d, dMTase catalyzes the transfer of a tritiated hydrogen from water to dCMP in methylated DNA in a time dependent manner only when methylated DNA is used as a substrate. Based on the experiments described in FIGS. 3 and 4 we propose that dMTase catalyzes the exchange of the methyl group at the 5' position of cytosine in DNA with hydrogen from water and the methyl group reacts with the remaining hydroxyl group to form methanol (FIG. 5).

Substrate and Sequence Specificity of DNA dMTase

Figure 6A:
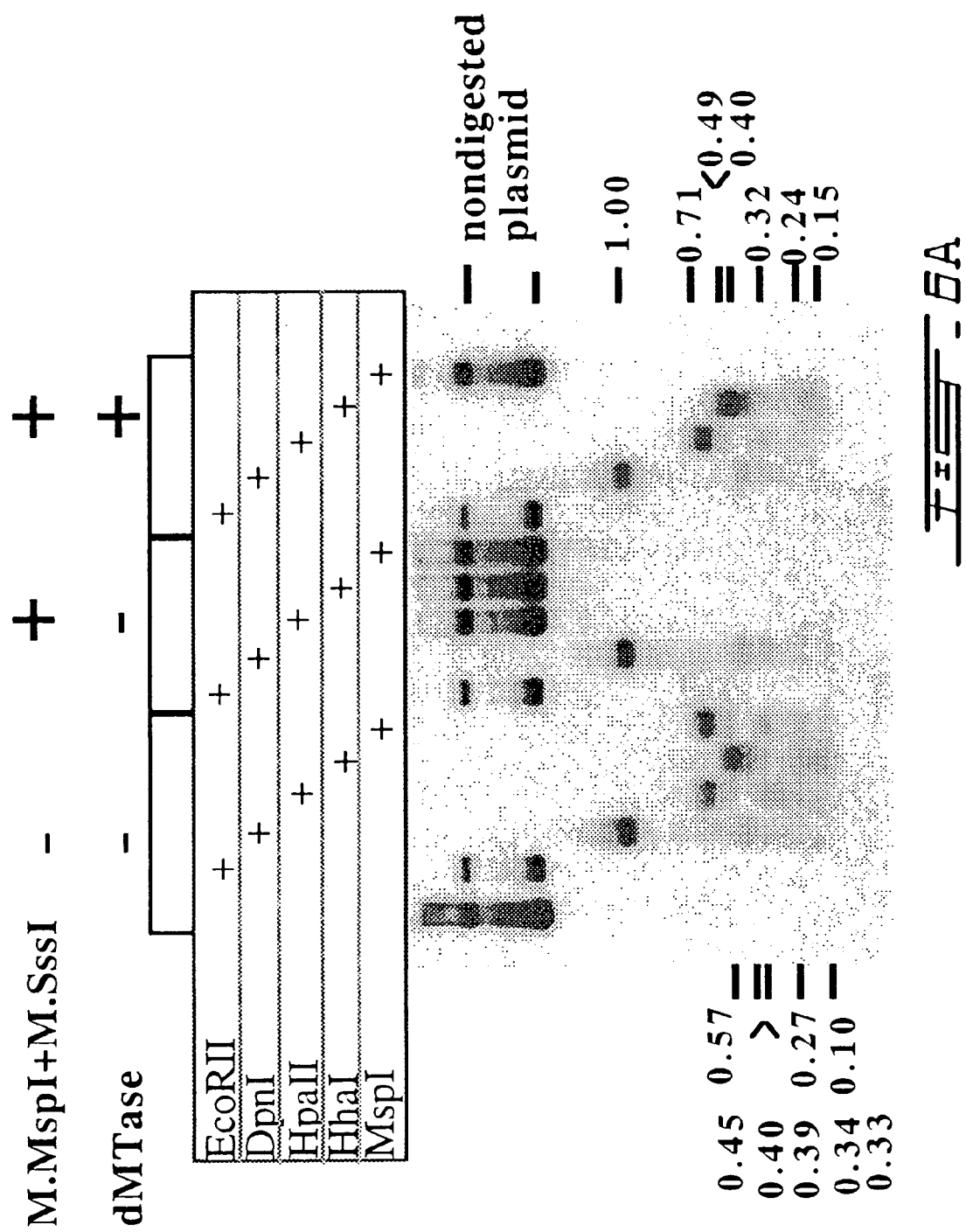
Figure 6C:
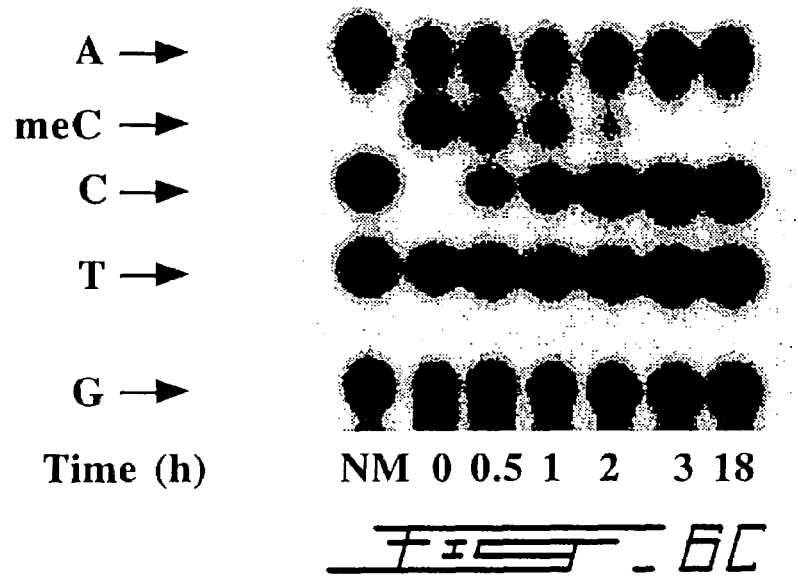
Figure 6D:
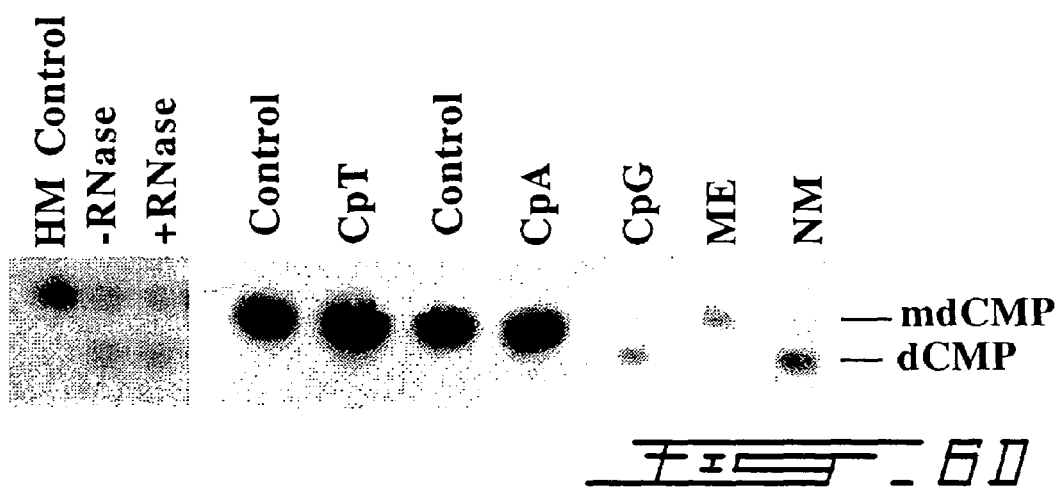

Methylation of CpG dinucleotides is the most characterized modification occurring in genomic DNA8,48. The results presented in FIG. 6 demonstrate that DNA dMTase is a general DNA dMTase activity that demethylates fully or hemimethylated dCpdG in DNA flanked by a variety of sequences which are distributed at different frequencies, but does not demethylate methylated adenines or methylated cytosines that do not reside in the dinucleotide CG. First, as shown in FIG. 6a, a plasmid DNA methylated in vitro at all dCpdG sites with M.Sss I and all d*CdCdGdG sites with M. Msp I (which methylates the external C in the sequence *CCGG, thus enabling the determination of demethylation at the CC dinucleotide) and in vivo with the E. coli DCM MeTase at dCmdCdA/dTdGdG sites and with the DAM MeTase at dGmdAdTdC sites (adenine methylated) was treated with dMTase and the state of methylation of the plasmid was determined using the indicated methylation sensitive restriction enzymes. dMTase demethylates C*G methylated sites as indicated by the sensitivity of the dMTase treated plasmid to Hpa II and Hha I but does not demethylate C*C, C*A or C*T methylated sites as indicated by the resistance to Msp I and Eco RII restriction enzymes, or adenine methylation as indicated by its sensitivity to Dpn. I. Second, bisulfite mapping analysis of methylation of 5 methylated C*G sites residing in a M.Sss I in vitro methylated pMetCAT plasmid following dMTase treatment shows that all C*G sites are demethylated irrespective of their flanking sequences thus excluding the possibility that demethylation is limited to CCGG or CGCG sequences (FIG. 6b). Third, dMTase does not demethylate two fully methylated cytosine bearing oligomers [dmC32pdA]n, [mdC32pdT]n demonstrating that mdCpdA and mdCpdT are not demethylated by DNA dMTase (FIG. 6d). Fourth, dMTase demethylates a hemimethylated synthetic substrate [dCpdG]n*[mdC32pdG]n (FIG. 6d). Demethylation of SK is complete under these conditions (FIG. 6a) whereas demethylation of a methylated [mdCpdG]n substrate is not complete under the same conditions (FIG. 6d). This can reflect differences in the sequence composition of the substrate and the frequency of methylated cytosines. The [mdCpdG]n contains on average 16 fold more methylated cytosines per molecule than plasmid DNA. Alternatively, these differences might reflect discrepancies in the assays used, restriction enzyme digestion versus a nearest neighbor analysis. To address this discrepancy we have labeled a fully methylated SK plasmid with [$\alpha^{32}$P]dCTP, 5-methyl-dCTP and the other dNTPs, subjected it to dMTase treatment and digested it to mononucleotides at different time points following the initiation of the reaction and subjected the samples to a TLC analysis. As shown in FIG. 6c, the SK plasmid is fully demethylated at 3 hours which is consistent with the results obtained with methylation sensitive restriction enzymes (FIG. 6a).

The Km of DNA dMTase for hemimethylated and fully methylated DNA was determined by measuring the initial velocity of the reaction at different concentrations of substrate (Table 2). The calculated Km for hemimethylated DNA is 6 nM which is two fold higher than the Km for DNA methylated on both strands, 2.5–3 nM (Table 2). It is unclear yet whether this small difference in affinity to the substrate has any significance in a cellular context. Thus similar to the DNA MeTase DNA dMTase shows dinucleotide sequence selectivity but in difference from DNA MeTase which shows preference to hemimethylated substrates dMTase prefers fully methylated DNA which is consistent with a role for DNA dMTase in altering established methylation patterns.

TABLE 1

Purification of DNA dMTase

| Purification step | Total protein (μg) | Total dpm | pMole/μg | pMole/μg/h | Fold Purification |
|---|---|---|---|---|---|
| Nuclear extract | 6000 | 1107.2 | $5.5 \times 10^{-5}$ | $1.833 \times 10^{-5}$ | — |
| DEAE-Sephadex | 3.75 | 5844 | 0.4674 | 0.156 | 8445.5 |
| SP-Sepharose | 0.77 | 5106 | 1.989 | 0.663 | 35939.84 |
| Q-Sepharose | 0.46 | 5335 | 3.4 | 1.13 | 62860.65 |
| DEAE-Sephacel | 0.018 | 1834 | 30.57 | 10.19 | 552243.2 |

TABLE 2

Kinetic parameters for DNA dMTase

| Method | $K_m$ (DNA) | $V_{max}$ (pMole/h) |
|---|---|---|
| Methylated oligo CpG | 2.5 nM | 340 |
| Hemi-methylated CpG | 6.0 nM | 402 |
| Methylated SK-DNA | 3.3 nM | 40.42 |

Cloning and Construction of Demethylase Expression Vectors

PCR Amplification of the MBD Domain of the Putative Demethylase Candidate cDNA

One μg of total RNA prepared from the human small lung carcinoma cell line A549 was reverse transcribed using Superscript reverse transcriptase and random primers (Boehringer) in a 25 μl reaction volume according to conditions recommended by the manufacturer (GIBCO-BRL). Five μl of reverse transcribed cDNA were subjected to an amplification reaction with Taq polymerase (Promega, 1 unit) using the following set of primers: sense 5' CTGGCAAGAGCGATGTC 3' SEQ ID NO:9, antisense 5' AGTCTGGTTTACCCTTATTTTG 3' SEQ ID NO:10.

Amplification conditions were: step 1. 95° C. 1 min.; step 2: 94° C. 0.5 min; step 3: 45° C. 0.5 min; step 4: 72° C. 1.5 min; steps 2–4 were repeated 30 times. MgCl$_2$ was adjusted to 1 mM according to conditions recommended by the manufacturer. The PCR products were cloned in pCR2.1 vector (InVitrogen) and the sequence of the cDNAs was verified by dideoxy-chain termination method using a T7 DNA sequencing kit (Pharmacia). The amplified fragment was excised from the plasmid with EcoRI, labeled with a Boehringer random prime labeling kit according to manufacturer's protocol and alpha $^{32}$P-dCTP. The labeled probe was used to screen a HeLa cell cDNA library in λTriplEx phage (Clontech) according to standard procedures. Positive clones were identified and further purified by serial dilutions for 4 rounds. The insert in the pTriplEx plasmid was excised from the phage according to manufacturer's protocols and the identity of the insert was verified by sequencing. The insert was excised by NotI restriction and subcloned into either the inducible expression vector: Retro tet on (Clontech) in the sense and antisense orientation or the pcDNA3.1/His Xpress vector in all three frames and in the antisense orientation.

Transfection and Expression of Demethylase in Vertebrate Cells

Ten μg of either Retro tet on demethylase or pcDNA 3.1/His Xpress demethylase are mixed with 8 μl of transfection lypophilic reagent Pfx-2 (Invitrogen) and placed upon 100,000 mouse (3T3 Balb/c, human (A549) or monkey cells (CV-1) according to manufacturer's protocol in OPTI-MEM medium for 4 hours. Cells are harvested after 48 hours and demethylation and demethylase activity is determined by measuring total genomic DNA methylation using standard techniques or a cotransfected in vitro methylated plasmid using a HpaII/MspI restriction enzyme analysis. Cellular transformation is measured by a soft agar assay.

Demethylation of pBluescript SK(+) Plasmid

About 4 μg plasmid pBluescript SK (Stratagene) was subjected to methylation using SssI methylase. The methylated plasmid (4 ng) was incubated for different time points as indicated with 30 μl of DNA dMTase Fraction 4 of DEAE-Sephacel™ column under standard conditions, extracted with phenol: chloroform and precipitated with ethanol. About 1 ng of the plasmid were subjected to digestion with 10 units each of either of the restriction endonuclease EcoRII (GIBCO-BRL), DpnI, or HpaII (New England Biolabs) before and after methylation as well as after DNA dMTase treatment in a reaction volume of 10 μl for 2 hour at 37° C. Following restriction digestion the plasmids were extracted with phenol:chloroform, ethanol precipitated and resuspended in 10 μl. The plasmids were electrophoresed on a 0.8% (w/w) Agarose gel, transferred onto a Hybond™ Nylon membrane and hybridized with pBluescript SK(+) plasmid which was $^{32}$P labeled by random-priming (Boehringer Mannheim).

dMTase activity coelutes with a ~45 KDa polypeptide when sized under denaturing conditions but migrates as a higher molecular weight complex under non denaturing conditions. dMTase was purified up to 500,000 fold by four chromatographic steps (Table 1). We first determined the identity of the polypeptide associated with dMTase activity by SDS-PAGE analysis of the active fractions. As observed in FIG. 7a, a cluster of 4 polypeptide bands from ~44 KDa to 35 KDa coelute with dMTase activity in the last two chromatographic steps (the lower fragment might be a degradation product as evidenced by its abundance in the later chromatographic steps). However when the active DEAE-Sephacel fraction is size fractionated on a 4% non denaturing acrylamide column, the dMTase activity elutes at the high molecular weight of ~170 KDa (FIG. 7c, fraction 63). SDS-PAGE analysis of this fraction (63) reveals only two bands (FIG. 7b) observed in the active chromatographic fractions (FIG. 7a) To further determine whether dMTase is found in a multimeric complex, fraction 63 was size fractionated on a glycerol gradient (FIG. 7d) and DNA dMTase activity eluted at the ~170 kDa range. As only two main small polypeptides were identified in fraction 63 (approximately 35–43 KDa), dMTase is probably found in either a homomeric complex if only one of the two peptides is dMTase or a heteromeric complex if both polypeptides are associated with dMTase activity.

a. Identification of a Lead DNA dMTase Candidate by Homology Search of dbEST

As the purification of dMTase suggests that the dMTase is of very low abundance, only ~19 ng of dMTase could be isolated from 6 mg of nuclear extract (Table 1), we opted for cloning the dMTase based on its following functional properties. First, since dMTase specifically demethylates methylated CG dinucleotides, we assumed that it should bear the ability to recognize methylated CG dinucleotides. Second, the demethylase transforms methylated cytosine in DNA to cytosine. Third, the demethylase releases the methyl group as a volatile compound.

Previous reports have shown that proteins interacting with methylated DNA share a common domain (MDBD). A TBLASTN search of the dbEST database identified a novel expression tag cDNA (from a T-cell lymphoma *Homo sapiens* cDNA 5' end) (gb/AA361957/AA361957 EST71295) and the mouse homologue ((gb/W97165/W97165 mf90g05.r1) from Soares mouse embryo NbME13.5) with unknown function that bears homology to the MDBD (FIG. 8a). A search of the GenBank database verified that it is a novel cDNA that has not been included in GenBank. Alignment of the novel EST and MeCP2 and MeCP1 associated protein has revealed no homology beyond the previously characterized MDBD which is consistent with a different function for this methylated DNA binding protein. A 201 bp fragment bearing the sequence identified in the search was reverse transcribed and amplified from human lung cancer cell line A549 RNA and was used to screen a cDNA library from Hela cells. The largest insert cloned was of 1.36 kb size and its sequence identity with the EST sequence was determined. The cDNA is novel and has no homologue in GenBank and no function has ever been assigned to it. A virtual translation of the protein identified an open reading frame (ORF) of 262 amino acids (FIG. 8b). The ORF may extend further 5' as no in frame stop codon was found upstream of this ATG. However, RACE analyses and further searches of the dbEST have failed to identify 5' sequences upstream to the one identified in our screening.

A BLAST search of the candidate protein using the Predict protein server against a database of protein domain families has identified only the MDBD domain and found no homologue to the sequence in the data base search. No other functional motifs were identified by the Prosite analysis. This is consistent with a novel biochemical function for this protein. A coiled coil prediction of the sequence identified a coiled coil domain which is known to play a role in protein protein interactions.

The identified cDNA encodes an mRNA that is widely expressed in human cells as revealed by a Northern blot analysis of human poly A+ mRNA (FIG. 8c) as one major transcript of ~1.6 kb which is close to the size of the cloned cDNA, verifying that the cloned cDNA does not represent a highly repetitive RNA but rather a mRNA encoded by a single or low copy number gene.

In Vitro Translated Candidate cDNA Bears dMTase Activity

Figure 10A:
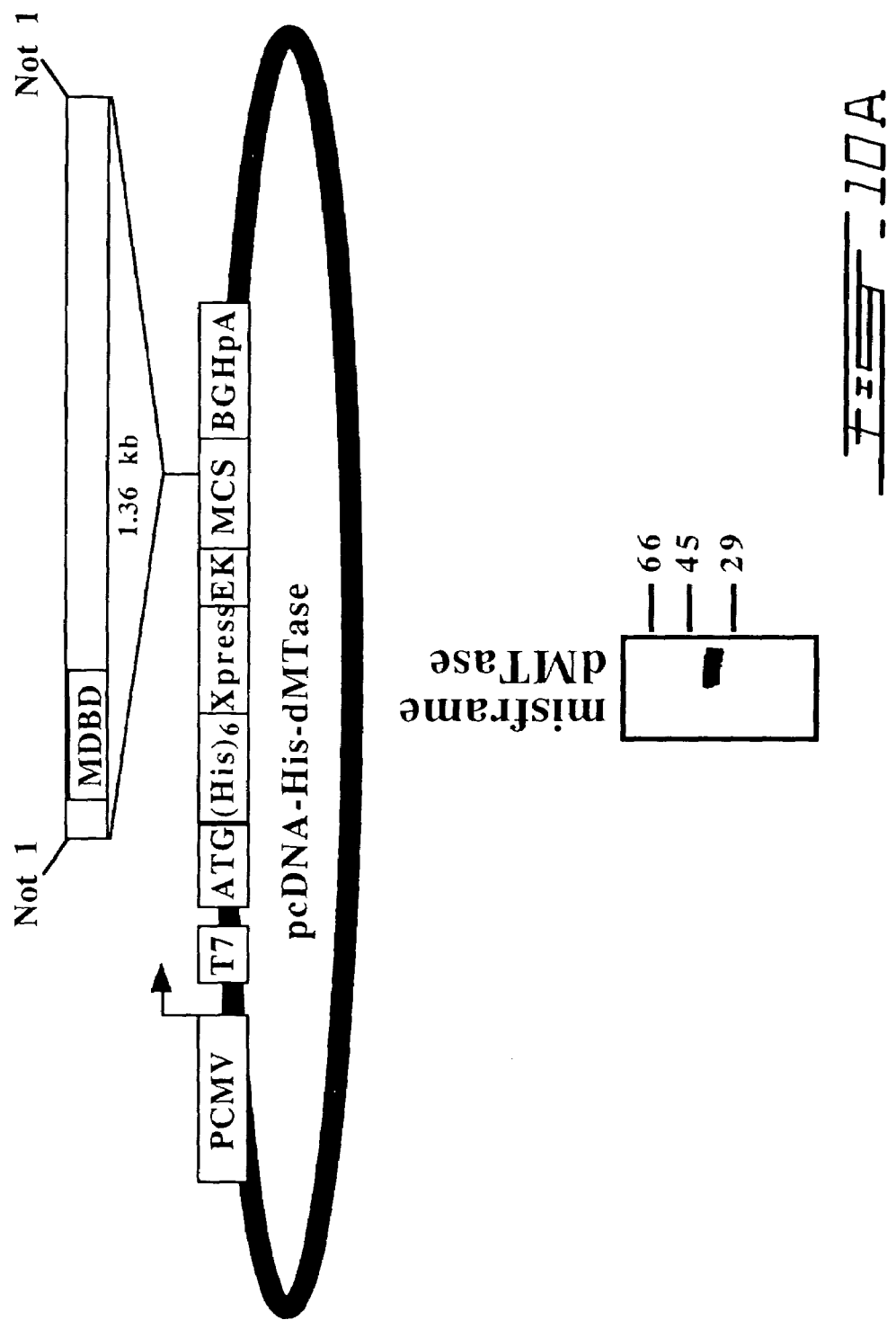
FIGS. 10A–B illustrate a mammalian expression vector of dMTase and in vitro translated dMTase polypeptide.

A conclusive proof for the existence of a single protein that bona fide demethylates DNA is to demonstrate that an in vitro translated candidate cDNA can volatilize methyl groups from methylated DNA and transform a methyl cytosine to cytosine in an isolated system. The candidate dMTase cDNA was subcloned it into a pcDNA3.1/His Xpress (INVITROGEN) expression vector in the putative translation frame (pcDNA3.1His A) and in a single base frame shift (pcDNA3.1His B), and was in vitro transcribed and translated in the presence of $^{35}$S-methionine and the resulting translation products were resolved by SDS-PAGE. Autoradiography revealed a ~40 KDa protein (FIG. 10a). The apparent size of the in vitro translated protein is shorter by ~3–5 KDa from the apparent size of the purified protein. The cloned cDNA might be missing some upstream amino acids as discussed above or might be differently modified in human cells.

Figure 10B:
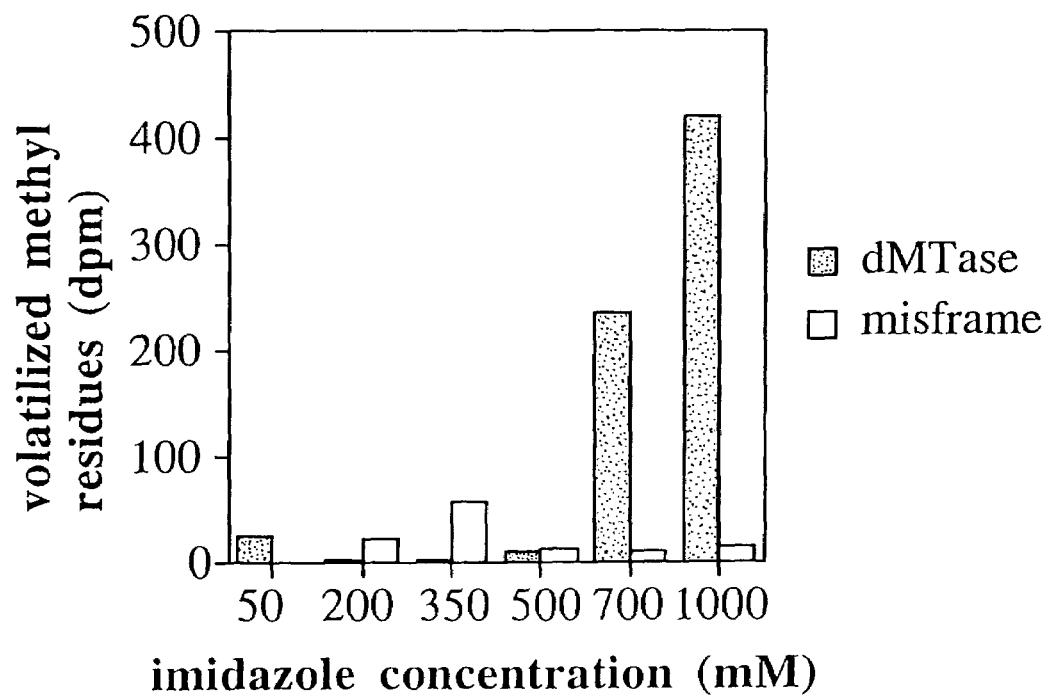

Two tests established whether the in vitro translated candidate cDNA is a bona fide dMTase. We first tested whether in vitro translated protein (purified on a Ni2+ charged agarose resin) can volatilize and release methyl residues in [$^3$H$_1$—CH$_3$-DNA using a radioactive trapping volatilization assay. To verify that the volatilized counts are true $^3$H counts, a spectrum analysis was performed. As demonstrated in FIG. 10b no volatilization of tritiated methyl residues is observed in the misframe dMTase (misframe) whereas in vitro translated putative dMTase cDNA catalyzes the volatilization of $^3$H-CH$_3$ residues which are trapped in the scintillation cocktail.

Second, in vitro translated dMTase cDNA transforms CH$_3$-cytosine residing in [$^{32}$P]-α-dGTP labeled plasmid DNA or in [methyl-dC32pdG]n double stranded oligomer DNA to cytosine, whereas a frame shift in vitro translated dMTase does not demethylate DNA (FIG. 10d). This demonstrates that the dMTase activity is dependent on the dMTase translation product and not a contaminating activity found in the in vitro translation kit that copurifies with the putative dMTase. The reaction carried out by the in vitro translated dMTase displays: dependence on the dose of in vitro translated product (FIG. 10c), time dependence (FIG. 10d) and dependence on translated protein (FIG. 10b & d misframe, FIG. 10c protease K treatment). Taken together, these results strongly suggest that the cDNA cloned here codes for a bona fide enzymatic DNA demethylase activity.

Figure 11A:
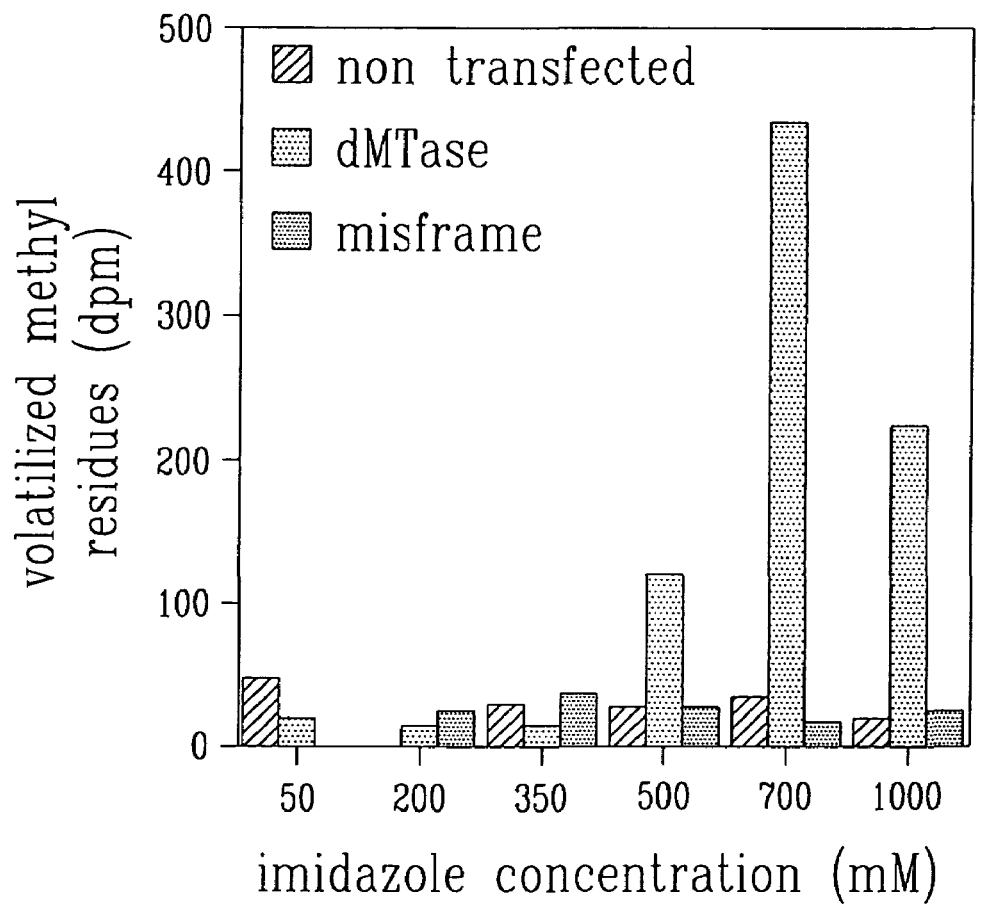
FIG. 11A illustrates that transiently transfected demethylase releases volatile residues from methylated DNA.
Figure 11F:
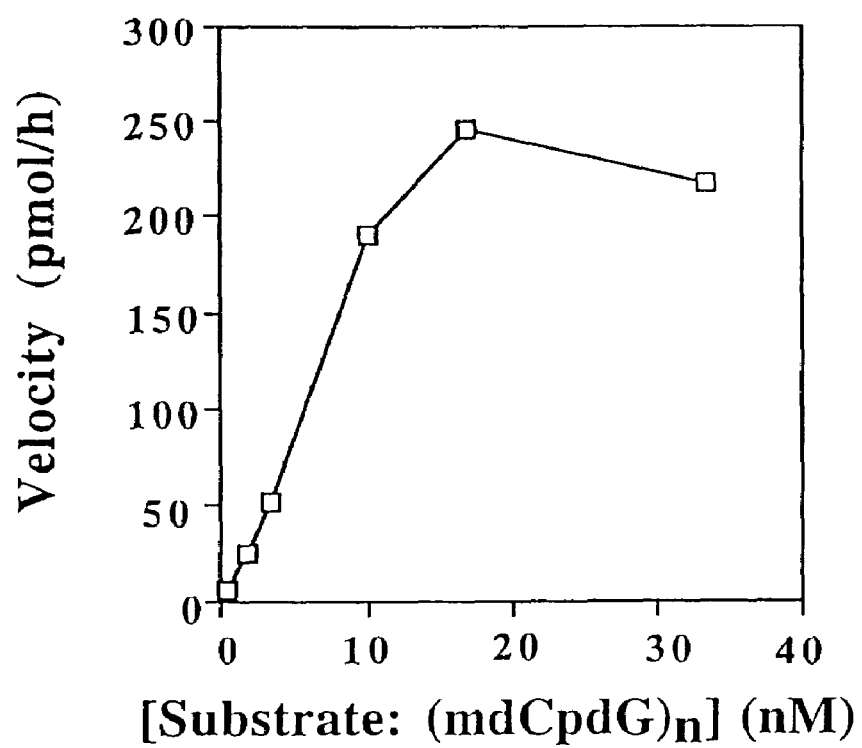
FIG. 11F illustrates that the transformation of methylated cytosine to cytosine by transiently transfected demethylase depends on the concentration of substrate.

Transiently Transfected dMTase cDNA Demethylates DNA dMTase cDNA and the pcDNA3.1His C vector control were transiently transfected into human embryonal kidney cells to test whether the cDNA can direct expression of dMTase activity in human cells. The His-tagged proteins were bound to Ni2+ agarose resin and eluted from the resin with increasing concentrations of imidazole. The expression of the transfected dMTase was verified by a Western blot analysis (FIG. 11b). The imidazole fractions were assayed for their ability to volatilize and release methyl residues in [$^3$H]—CH$_3$-DNA using a radioactive trapping volatilization assay 1. As observed in FIG. 11a, imidazole fractions from dMTase transfected cells volatilize [$^3$H]—CH$_3$ whereas no tritiated counts are detected in DNA treated with imidazole fractions from cells transfected with a misframe mutation of dMTase or non transfected cells. The transiently expressed dMTase transforms methylated cytosine in DNA to cytosine residing in two different substrates (FIGS. 11c & 11d), in a protein dependent manner (FIGS. 11c & 11e), and the reaction displays substrate dependence and saturability (FIG. 11f). Transiently expressed dMTase was loaded on a non denaturing glycerol gradient to determine its native MW. Similar to dMTase purified from human cells, cloned and purified dMTase activity fractionated at the 160–190 KDa range (data not shown). This is consistent with self association of cloned dMTase possibly mediated by the coiled-coil domain.

Figure 12A:
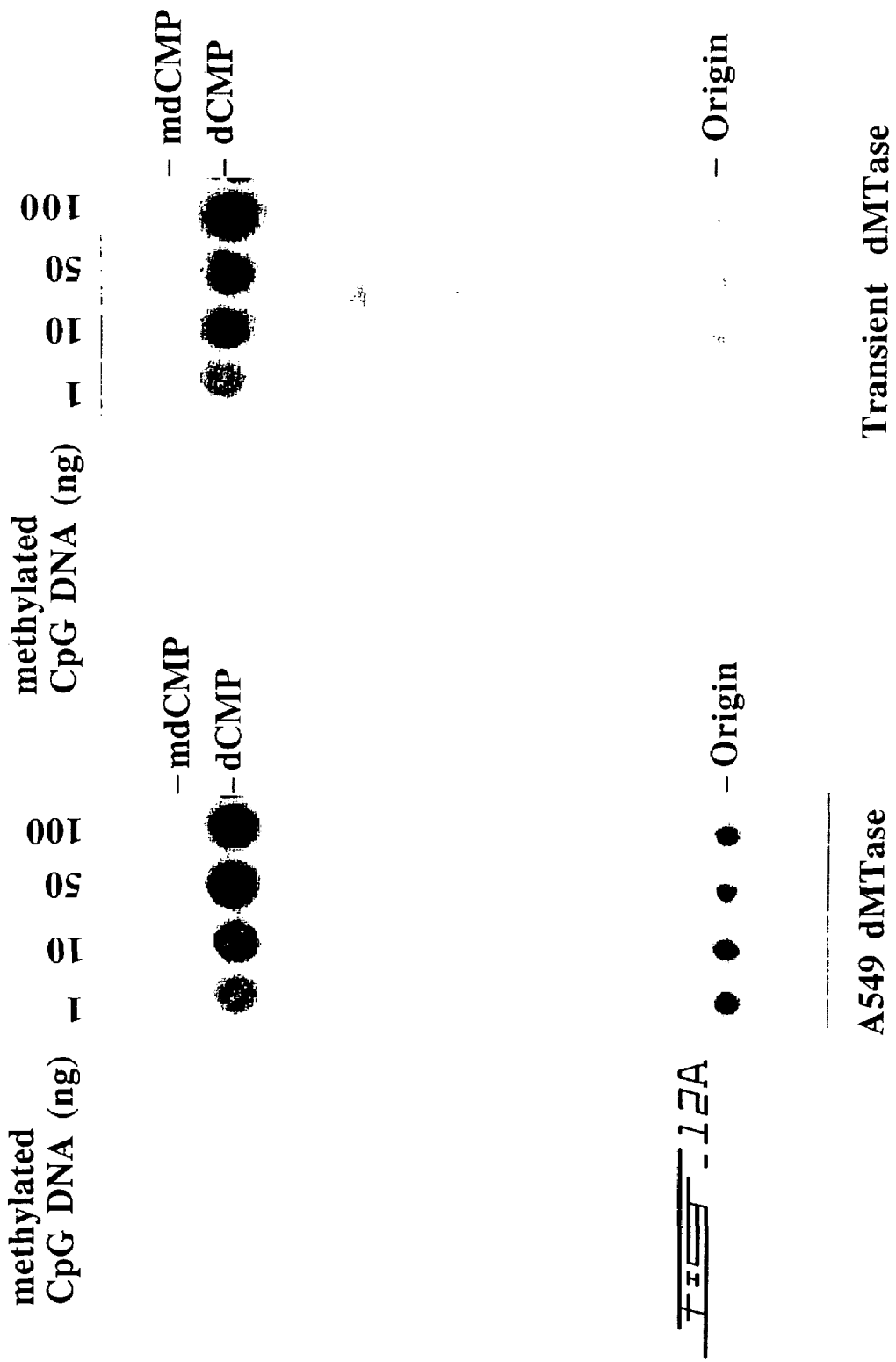
FIG. 12A illustrates that transiently transfected demethylase catalyzes the transfer of a proton from tritiated water to regenerate cytosine.

Cloned DNA dMTase Catalyzes a Hydrolysis of 5-methyl-Cytosine to Release Methanol We determined the mechanism by which methyl residues are released by the cloned dMTase (from FIG. 11) and compared it to the purified bona fide dMTase activity. Increasing amounts of non labeled (methyl-dCpdG] DNA were incubated with either the bona fide dMTase activity purified from A549 cells or the cloned dMTase in the presence of [$^3$H] water for 3 hours followed by digestion to mononucleotides, a thin layer chromatography and autoradiography. As FIG. 12a shows, both reactions replace the methyl group in 5-methyl-cytosine with a proton donated from water as indicated by the presence of [$^3$H] label in cytosine.

The identity of the leaving methyl group in the demethylation reaction catalyzed by the purified bona fide dMTase activity was shown to be methanol. In order to identify the form that the methyl residue leaves as in the demethylation reaction catalyzed by the cloned dMTase an identical gas chromatography/mass spectrometry analysis of the reaction products was performed as in1. Only the properly translated form of dMTase (both in vitro translated and transiently transfected and purified) is able to produce ions characteristic of methanol in a mass spectrometric analysis (mass of 32 and 29, FIG. 12b). These results suggest that the demethylation reaction catalyzed by the cloned dMTase is hydrolysis of the 5-methyl-cytosine to cytosine and methanol as described for the purified dMTase1.

DNA dMTase Activity is Undetectable in Nontransformed Cells

The assays for dMTase activity described here and the cloning of DNA dMTase cDNA enables a study of its expression at different cellular states. Global hypomethylation of DNA is a common observation in cancer cells. This has been a perplexing observation, since DNA MeTase activity is elevated in cancer cells. Hyperactivation of DNA MeTase has been proposed to play a role in cancer development. This paradox raises questions on the proposed role of the elevated levels of DNA MeTase in cancer cells. One simple explanation that has been previously suggested to resolve this paradox is that cancer cells express induced levels of DNA dMTase. We compared the DNA dMTase activity in equal concentrations of DEAE-Sephadex fractionated nuclear extracts (fractions 9–10) prepared from a number of carcinoma cell lines H446, Colo 205, Hela, and A549 with a similar preparation from human skin fibroblast cells at initial rate conditions using [mdC32pdG]n double stranded oligomer as a substrate. As observed in FIG. 13a, whereas DNA dMTase activity is readily observed in all carcinoma cell lines, it is undetectable in nontransformed human cells. The absence of dMTase activity in human primary cells reflects the situation in vivo since dMTase activity is undetectable in preparations from different murine tissues whereas dMTase activity is present in a murine carcinoma cell line P19 that was transfected with the H-Ras protooncogene, or human tumors carried as xenografts in the same strain of mouse (FIG. 1a: COLO 205, A549. Hela).

Figure 13C:
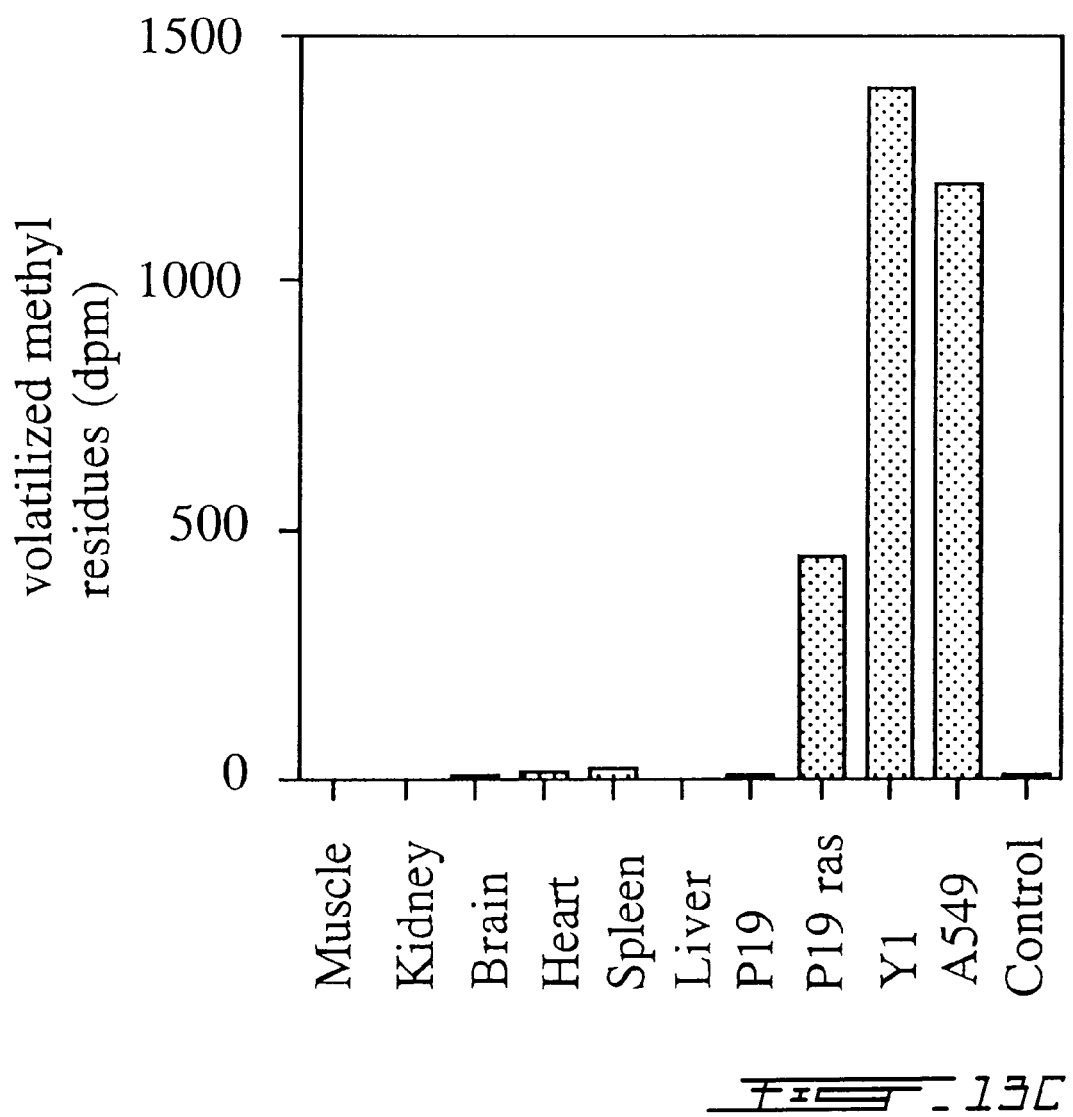
Figure 14A:
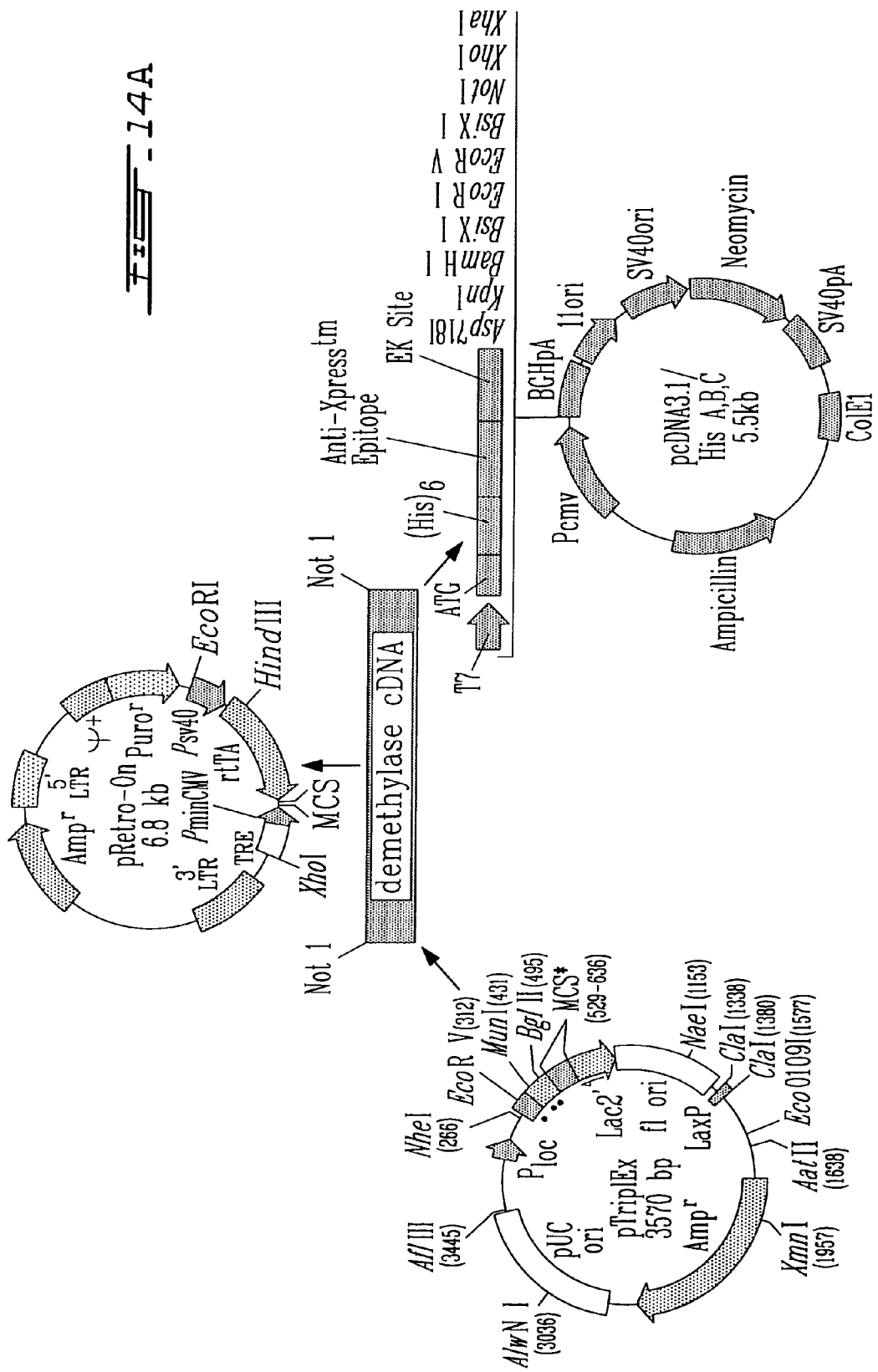
FIG. 14A illustrates demethylase bacterial retroviral and mammalian expression vector.
Figure 14B:
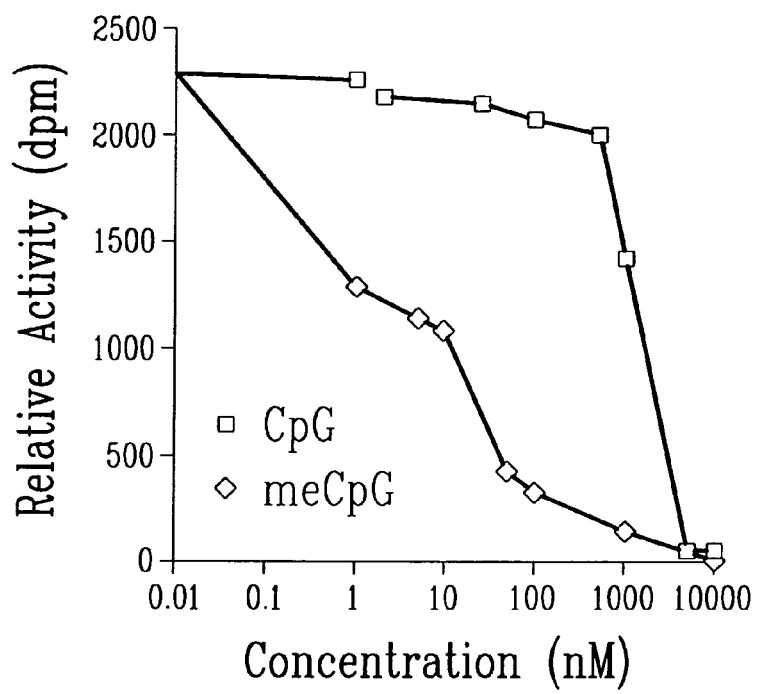
FIG. 14B illustrates inhibition of demethylase activity by a specific inhibitor.
Figure 14C:
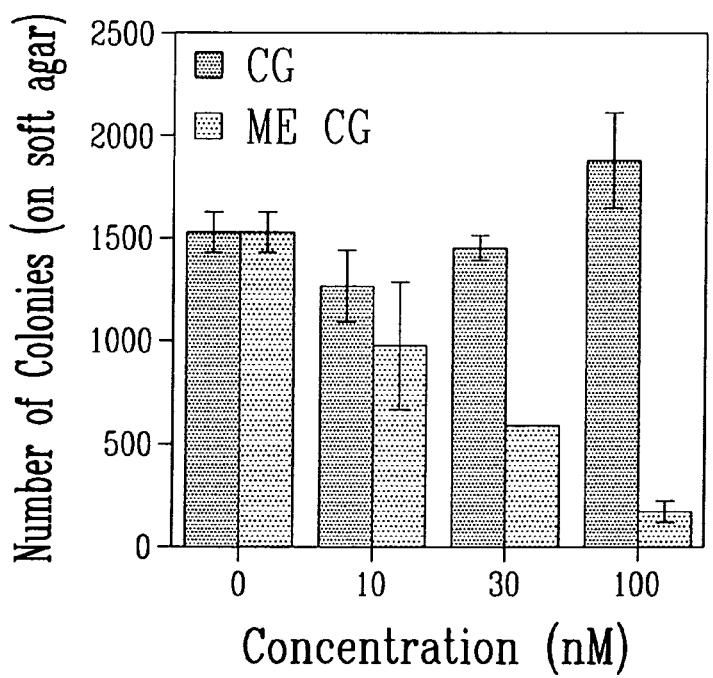
FIG. 14C illustrates inhibition of growth on soft agar of colonies of tumor cells in vitro by an inhibition of demethylase.

These conclusions were verified using the radioactive-trapping volatilization assay shown in FIG. 13c.

Since dMTase mRNA has been detected using a sensitive poly A+ Northern blot in all normal human tissues, we tested the hypothesis that the absence of detected dMTase activity in normal tissues reflects a quantitative difference in DNA dMTase mRNA between normal tissues and cancer lines. A Northern blot analysis and quantification of dMTase mRNA by a slot blot analysis shown in FIG. 13d using total RNA supports this hypothesis. Whereas minute levels of dMTase mRNA are detected in normal tissues, high levels of dMTase are expressed in a murine carcinoma cell line Y1 that bears a 30 fold amplification of Ha-ras.

A second DNA Demethylase dMTase2 Identified in Human and Mouse cDNA sequences, predicted amino acid sequences, and GenBank accession numbers of both dMTase1 and dMTase2 from human and mouse are shown. We claim that the high level of identity of the two proteins (FIGS. 9c and e) suggests that the two proteins can perform the same function, DNA demethylation. The N-terminals of dMTase1 and dMTase2 contain a Methylated DNA Binding Domain (MBD) and near their C-terminals is a coiled-coil domain, however the middle portions of the protein sequences have no homology to any know structural or catalytic motif. Importantly, their middle regions are still extensively homologous suggesting that the catalytic site of the demethylase activity lies in this area on both proteins.

Induced Expression of DNA Demethylase in the Antisense Orientation Inhibits Tumorigenesis Ex Vivo To test the hypothesis that inhibition of DNA dMTase can inhibit tumorigenesis tetracycline inducible vectors carrying the human dMTase1 cDNA in either the sense or antisense orientation were constructed and transiently transfected into HEK 293 cells, treated for 48 hours either in the presence or absence of doxycycline (a tetracycline analogue), selected for the last 24 hours with puromycin, and then plated on soft agar and allowed to grow for seven days. After seven days colonies were scored and the data presented clearly show that doxycycline induced expression of the dMTase1 cDNA in the antisense orientation reduced colony formation (FIG. 15).

Imidazole is a Small Molecule Inhibitor of DNA Demethylase Activity

Figure 16:
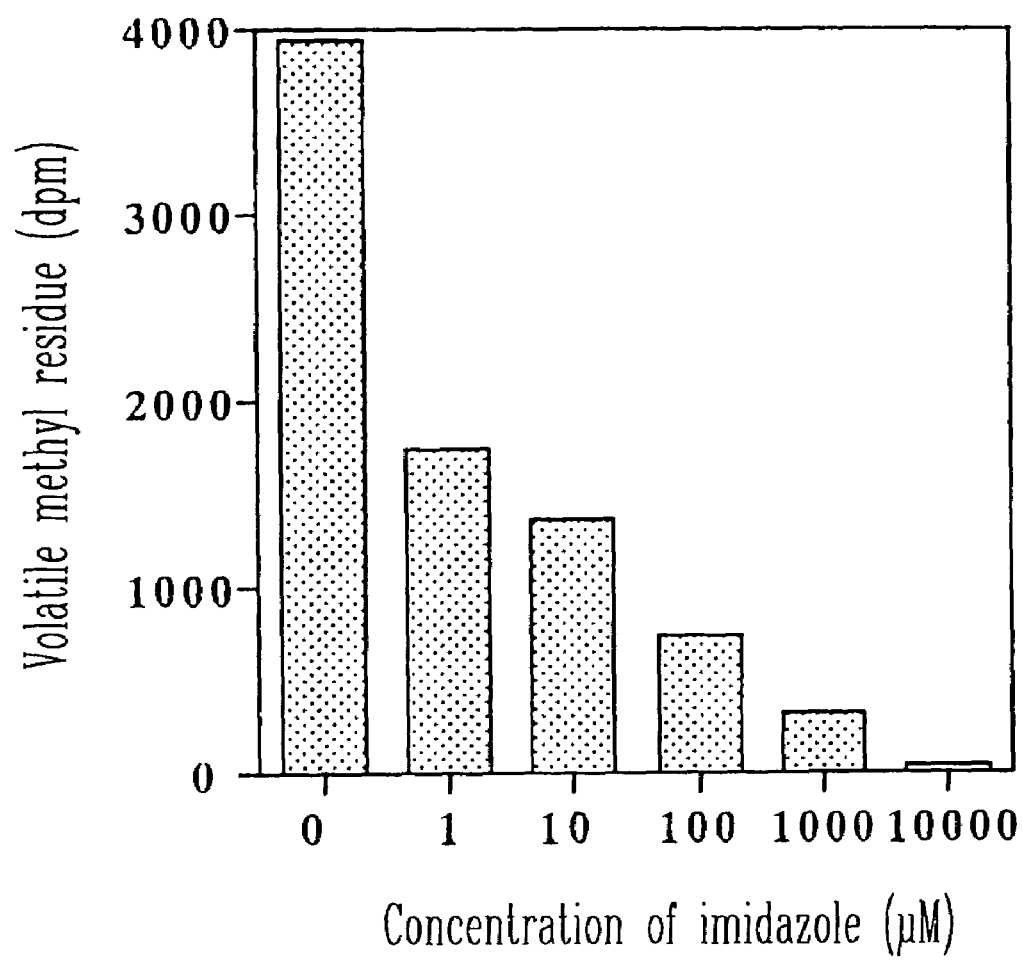
FIG. 16 illustrates the inhibition of demethylase by a small molecule inhibitor imidazole.

A template small molecule, imidazole, was tested for the ability to inhibit DNA dMTase activity. In a volatilization of radioactive methyl residues assay, concentrations from 1 μM to 10 mM of imidazole were incubated in a typical volatilization of radioactive methyl residues as described above. The graph clearly demonstrates a dose dependent inhibition of DNA dMTase activity by imidazole, and validates a rationale for testing imidazole based molecules as inhibitors of DNA dMTase activity (FIG. 16).

Identification of DNA Demethylase cDNAs and Protein Sequences

FIG. 9a illustrates cDNA sequence of human dMTase1 (SEQ ID NO:1) and its predicted amino acid sequence (SEQ ID NO:2), including its Genbank location. FIG. 9b illustrates cDNA sequence of human dMTase2 (SEQ ID NO:3) and its predicted amino acid sequence(SEQ ID NO:4), including its GenBank location. FIG. 9c illustrates protein sequence alignment of human dMTase1 and human dMTase2. FIG. 9d illustrates cDNA sequence of mouse dMTase1 (SEQ ID NO:5) and its predicted amino acid sequence (SEQ ID NO:6), including its GenBank location. FIG. 9e illustrates cDNA sequence of mouse dMTase2 (SEQ ID NO:7) and its predicted amino acid sequence (SEQ ID NO:8), including its GenBank location. FIG. 9f illustrates protein sequence alignment of mouse dMTase1 and mouse dMTase2.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of altering a demethylation activity of DNA demethylase in an isolated human cell, the method comprising inhibiting DNA demethylase with an antagonist selected from the group consisting of a double stranded $C^mG$ oligonucleotide, an anti-DNA demethylase antibody, antisense oligonucleotide of DNA demethylase, and imidazole, wherein said DNA demethylase comprises amino acids 150–411 of SEQ ID NO:2.

2. The method according to claim 1, wherein said antagonist is a double stranded $C^mG$ oligonucleotide that inhibits DNA demethylase at a Ki of 50 nM.

3. The method according to claim 2, wherein said oligonucleotide is

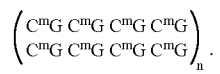

4. The method according to claim 1, wherein said antagonist is an anti-DNA demethylase antibody.

5. The method according to claim 1, wherein said antagonist is an antisense oligonucleotide of DNA demethylase.

6. The method according to claim 1, wherein said antagonist is imidazole.

* * * * *

SEQUENCE LISTING

<160> NUMBER OF SEQ ID NOS: 10

<210> SEQ ID NO 1
<211> LENGTH: 1804
<212> TYPE: DNA
<213> ORGANISM: Unknown
<220> FEATURE:
<223> OTHER INFORMATION: cDNA encoding human demethylase

<400> SEQUENCE: 1

| | | | | | |
|---|---|---|---|---|---|
| ccgctctgcg | gcgggcgg | gtctccggga | ttccaagggc | tcggttacgg | aagaagcgca | 60 |
| gagccggctg | gggaggggc | tggatgcgcg | cgcacccggg | gggaggccgc | tgctgcccgg | 120 |
| agcaggagga | ggggagagc | gcggcgggcg | gcagcggcgc | tggcggcgac | tccgccatag | 180 |
| agcagggggg | ccagggcagc | gcgctcgctc | cgtccccggt | gagcggcgtg | cgcagggaag | 240 |
| gcgctcgggg | cggcggccgt | ggccggggc | ggtggaagca | ggcggcccgg | ggcggcggcg | 300 |
| tctgtggccg | tggccgtggc | cgtggccggg | gtcggggccg | tggccggggc | cggggccggg | 360 |
| gccgcggccg | tccccagagt | ggcggcagcg | gccttggcgg | cgacggcggc | ggcggcgcgg | 420 |
| gcggctgcgg | cgtcggcagc | ggtggcggcg | tcgccccccg | gcgggatcct | gtccctttcc | 480 |
| cgtcggggag | ctcggggccg | gggcccaggg | gacccccggg | cacggagagc | gggaagagga | 540 |
| tggactgccc | ggccctcccc | cccggatgga | agaaggagga | agtgatccga | aaatcagggc | 600 |
| tcagtgctgg | caagagcgat | gtctactact | tcagtccaag | tggtaagaag | ttcagaagta | 660 |
| aacctcagct | ggcaagatac | ctgggaaatg | ctgttgacct | tagcagtttt | gacttcagga | 720 |
| ccggcaagat | gatgcctagt | aaattacaga | agaacaagca | gagactccgg | aatgaccccc | 780 |
| tcaatcagaa | caagggtaaa | ccagacctga | acacaacatt | gccaattaga | caaactgcat | 840 |
| caattttcaa | gcaaccagta | accaaattca | cgaaccaccc | gagcaataag | gtgaagtcag | 900 |
| accccagcg | gatgaatgaa | caaccacgtc | agcttttctg | ggagaagagg | ctacaaggac | 960 |
| ttagcgcatc | agatgtaaca | gaacaaatta | taaaaaccat | ggagctacct | aaaggtcttc | 1020 |
| aaggagtcgg | tccaggtagc | aatgacgaga | cccttctgtc | tgctgtggcc | agtgctttac | 1080 |
| acacaagctc | tgcgcccatc | acaggacaag | tctctgctgc | cgtggaaaag | aaccctgctg | 1140 |
| tttggcttaa | cacatctcaa | cccctctgca | aagctttcat | tgttacagat | gaagacatta | 1200 |
| ggaaacagga | agagcgagtc | caacaagtac | gcaagaaact | ggaggaggca | ctgatggccg | 1260 |
| acatcctgtc | ccgggctgcg | gacacggagg | aagtagacat | tgacatggac | agtggagatg | 1320 |
| aggcgtaaga | atatgatcag | gtaactttcg | actgaccttc | cccaagagca | aattgctaga | 1380 |
| aacagaatta | aaacatttcc | actgggtttc | gcctgtaaga | aaaagtgtac | ctgagcacat | 1440 |
| agcttttttaa | tagcactaac | caatgccttt | ttagatgtat | ttttgatgta | tatatctatt | 1500 |
| attccaaatg | atgtttattt | tgaatcctag | gacttaaaat | gagtctttta | taatagcaag | 1560 |
| cagggccctt | ccggtgcagt | gcagctttga | ggccaggtgc | agtctactgg | aaaggtagca | 1620 |
| cttacgtgaa | atatttgttt | cccccacagt | tttaatataa | acagatcagg | agtaccaaat | 1680 |

```
aagtttccca attaaagatt attatacttc actgtatata aacagatttt tatactttat    1740
tgaaagaaga tacctgtaca ttcttccatc atcactgtaa agacaaataa atgactatat    1800
tcac                                                                  1804
```

<210> SEQ ID NO 2
<211> LENGTH: 411
<212> TYPE: PRT
<213> ORGANISM: Unknown
<220> FEATURE:
<223> OTHER INFORMATION: predicted amino acid of human demethylase

<400> SEQUENCE: 2

```
Met Arg Ala His Pro Gly Gly Arg Cys Cys Pro Glu Gln Glu Glu
 1               5                  10                  15

Gly Glu Ser Ala Ala Gly Gly Ser Gly Ala Gly Gly Asp Ser Ala Ile
                20                  25                  30

Glu Gln Gly Gly Gln Gly Ser Ala Leu Ala Pro Ser Pro Val Ser Gly
                35                  40                  45

Val Arg Arg Glu Gly Ala Arg Gly Gly Arg Gly Arg Gly Arg Trp
 50                  55                  60

Lys Gln Ala Gly Arg Gly Gly Val Cys Gly Arg Gly Arg Gly Arg
 65                  70                  75                  80

Gly Arg Gly Arg Gly Arg Gly Arg Gly Arg Gly Arg Gly Arg
                85                  90                  95

Pro Pro Ser Gly Gly Ser Gly Leu Gly Gly Asp Gly Gly Cys Gly
                100                 105                 110

Gly Gly Gly Ser Gly Gly Gly Ala Pro Arg Arg Glu Pro Val Pro
                115                 120                 125

Phe Pro Ser Gly Ser Ala Gly Pro Gly Pro Arg Gly Pro Arg Ala Thr
                130                 135                 140

Glu Ser Gly Lys Arg Met Asp Cys Pro Ala Leu Pro Pro Gly Trp Lys
145                 150                 155                 160

Lys Glu Glu Val Ile Arg Lys Ser Gly Leu Ser Ala Gly Lys Ser Asp
                165                 170                 175

Val Tyr Tyr Phe Ser Pro Ser Gly Lys Lys Phe Arg Ser Lys Pro Gln
                180                 185                 190

Leu Ala Arg Tyr Leu Gly Asn Thr Val Asp Leu Ser Ser Phe Asp Phe
                195                 200                 205

Arg Thr Gly Lys Met Met Pro Ser Lys Leu Gln Lys Asn Lys Gln Arg
                210                 215                 220

Leu Arg Asn Asp Pro Leu Asn Gln Asn Lys Gly Lys Pro Asp Leu Asn
225                 230                 235                 240

Thr Thr Leu Pro Ile Arg Gln Thr Ala Ser Ile Phe Lys Gln Pro Val
                245                 250                 255

Thr Lys Val Thr Asn His Pro Ser Asn Lys Val Lys Ser Asp Pro Gln
                260                 265                 270

Arg Met Asn Glu Gln Pro Arg Gln Leu Phe Trp Glu Lys Arg Leu Gln
                275                 280                 285

Gly Leu Ser Ala Ser Asp Val Thr Glu Gln Ile Ile Lys Thr Met Glu
                290                 295                 300

Leu Pro Lys Gly Leu Gln Gly Val Gly Pro Gly Ser Asn Asp Glu Thr
305                 310                 315                 320

Leu Leu Ser Ala Val Ala Ser Ala Leu His Thr Ser Ser Ala Pro Ile
                325                 330                 335
```

```
Thr Gly Gln Val Ser Ala Ala Val Glu Lys Asn Pro Ala Val Trp Leu
            340                 345                 350

Asn Thr Ser Gln Pro Leu Cys Lys Ala Phe Ile Val Thr Asp Glu Asp
        355                 360                 365

Ile Arg Lys Gln Glu Glu Arg Val Gln Gln Val Arg Lys Lys Leu Glu
        370                 375                 380

Glu Ala Leu Met Ala Asp Ile Leu Ser Arg Ala Ala Asp Thr Glu Glu
385                 390                 395                 400

Met Asp Ile Glu Met Asp Ser Gly Asp Glu Ala
                405                 410

<210> SEQ ID NO 3
<211> LENGTH: 1589
<212> TYPE: DNA
<213> ORGANISM: Unknown
<220> FEATURE:
<223> OTHER INFORMATION: cDNA sequence of human dMTase2

<400> SEQUENCE: 3
```

| | |
|---|---:|
| cacgcgcggg cgggtgggcg gagcggcccc cctagcgggg gctgtgaagc gcggggaggg | 60 |
| ggccgagcgg gtggcgaagc cggcgcgcgc ccggctgggg gcggagggcg gaggcccgtg | 120 |
| ggacagaaca gctgcggcga gtggcggcgg cggagggagc cgaatcggcg acgagcccgg | 180 |
| gggtcgcaac ttgcagaagc ggcggcggcg gcggcatcgg ccacggcggg cggaaaagcc | 240 |
| ggggcgcaat ggagcggaag aggtgggagt gcccggcgct cccgcagggc tgggaaaggg | 300 |
| aagaagtgcc caggaggtcg gggctgtcgg ccggccacag ggatgtcttt tactatagcc | 360 |
| ccagcgggaa gaagttccgc agcaagccac aactggcacg ttacctgggc ggatccatgg | 420 |
| acctcagcac cttcgacttc cgcaccggaa agatgttgat gaacaagatg aataagagtc | 480 |
| gccagcgtgt gcgctatgat tcttccaacc aggtcaaggg caagcctgac ctgaacaccg | 540 |
| cgctgcctgt acggcagact gcatccatct tcaagcaacc ggtgaccaag atcaccaacc | 600 |
| accccagcaa caaggtcaag agcgacccgc agaaggcagt ggaccagccg aggcagcttt | 660 |
| tctgggagaa gaagctaagt ggattgagtg cctttgacat tgcagaagaa ctggtcagga | 720 |
| ccatggactt gcccaagggc ctgcagggag tgggccctgg ctgtacagat gagacgctgc | 780 |
| tgtcagccat tgcgagtgct ctacacacca gcaccctgcc cattacaggc cagctctctg | 840 |
| cagccgtgga agaaccctgg tgtgtggc tgaacactgc acagccactg tgcaaagcct | 900 |
| tcatggtgac agatgacgac atcaggaagc aggaggagct ggtacagcag gtacggaagc | 960 |
| gcctggagga ggcactgatg gccgacatgc tagctcatgt ggaggagctt gcccgagacg | 1020 |
| gggaggcacc actggacaag gcctgtgcag aggaggaaga ggaggaggaa gaggaggagg | 1080 |
| aagagccgga gccagagcga gtgtagcaca ggtgccctgc ccaagtctgg gctgcagact | 1140 |
| gccttcagcc ttgcctggac caggtagggg ccagacctgt aggaggcagc cgtccacctc | 1200 |
| ctttccaaag cctcctgctt ccaggtctca gtgcagggag ccctgtggga ccttgaactc | 1260 |
| acttgtccct gcgctgcctg gcaggaagcc ccacactgaa agcagatgag cagtgaccca | 1320 |
| actgagaggc cacctggaca cagtcacctc cctgcctcct tatcatagga caaggccttg | 1380 |
| cttggcaccg aggagctggg agccgtgttg ggtgctggag gaagtttctg gaaacacacc | 1440 |
| tggctatgcc caccttatgt ccctaaggct attacaggcc agggtttgga ctgctccggc | 1500 |
| ccacagggct gccagcctc cccacactga gggtcagcag cccaccagga agtcactttc | 1560 |
| cttcaataaa ctgatggtag gaacttgtg | 1589 |

<210> SEQ ID NO 4
<211> LENGTH: 291
<212> TYPE: PRT
<213> ORGANISM: Unknown
<220> FEATURE:
<223> OTHER INFORMATION: predicted amino acid sequence of human dMTase2

<400> SEQUENCE: 4

```
Met Glu Arg Lys Arg Trp Glu Cys Pro Ala Leu Pro Gln Gly Trp Glu
 1               5                  10                  15

Arg Glu Glu Val Pro Arg Arg Ser Gly Leu Ser Ala Gly His Arg Asp
            20                  25                  30

Val Phe Tyr Tyr Ser Pro Ser Gly Lys Lys Phe Arg Ser Lys Pro Gln
        35                  40                  45

Leu Ala Arg Tyr Leu Gly Gly Ser Met Asp Leu Ser Thr Phe Asp Phe
    50                  55                  60

Arg Thr Gly Lys Met Leu Met Ser Lys Met Asn Lys Ser Arg Gln Arg
65                  70                  75                  80

Val Arg Tyr Asp Ser Ser Asn Gln Val Lys Gly Lys Pro Asp Leu Asn
                85                  90                  95

Thr Ala Leu Pro Val Arg Gln Thr Ala Ser Ile Phe Lys Gln Pro Val
            100                 105                 110

Thr Lys Ile Thr Asn His Pro Ser Asn Lys Val Lys Ser Asp Pro Gln
        115                 120                 125

Lys Ala Val Asp Gln Pro Arg Gln Leu Phe Trp Glu Lys Lys Leu Ser
    130                 135                 140

Gly Leu Asn Ala Phe Asp Ile Ala Glu Glu Leu Val Lys Thr Met Asp
145                 150                 155                 160

Leu Pro Lys Gly Leu Gln Gly Val Gly Pro Gly Cys Thr Asp Glu Thr
                165                 170                 175

Leu Leu Ser Ala Ile Ala Ser Ala Leu His Thr Ser Thr Met Pro Ile
            180                 185                 190

Thr Gly Gln Leu Ser Ala Ala Val Glu Lys Asn Pro Gly Val Trp Leu
        195                 200                 205

Asn Thr Thr Gln Pro Leu Cys Lys Ala Phe Met Val Thr Asp Glu Asp
    210                 215                 220

Ile Arg Lys Gln Glu Glu Leu Val Gln Gln Val Arg Lys Arg Leu Glu
225                 230                 235                 240

Glu Ala Leu Met Ala Asp Met Leu Ala His Val Glu Glu Leu Ala Arg
                245                 250                 255

Asp Gly Glu Ala Pro Leu Asp Lys Ala Cys Ala Glu Asp Asp Glu
            260                 265                 270

Glu Asp Glu Glu Glu Glu Glu Glu Pro Asp Pro Asp Pro Glu Met
        275                 280                 285

Glu His Val
    290
```

<210> SEQ ID NO 5
<211> LENGTH: 1966
<212> TYPE: DNA
<213> ORGANISM: Unknown
<220> FEATURE:
<223> OTHER INFORMATION: cDNA sequence of mouse dMTase1

<400> SEQUENCE: 5 ggggcgtgg cccccgagaag gcggagacaa gatggccgcc catagcgctt ggaggaccta    60

-continued

```
agaggcggtg gccggggcca cgccccgggc aggagggccg ctctgtgcgc gcccgctcta    120
tgatgcttgc gcgcgtcccc cgcgcgccgc gctgcgggcg gggcgggtct ccgggattcc    180
aagggctcgg ttacggaaga agcgcagcgc cggctgggga gggggctgga tgcgcgcgca    240
cccgggggga ggccgctgct gcccggagca ggaggagggg gagagtgcgg cgggcggcag    300
cggcgctggc ggcgactccg ccatagagca gggggggccag ggcagcgcgc tcgccccgtc    360
cccggtgagc ggcgtgcgca gggaaggcgc tcggggcggc ggccgtggcc gggggcggtg    420
gaagcaggcg ggccggggcg gcggcgtctg tggccgtggc cggggccggg gccgtggccg    480
gggacgggga cggggccggg gccggggccg cggccgtccc ccgagtggcg gcagcggcct    540
tggcggcgac ggcggcggct gcggcggcgg cggcagcggt ggcggcggcg ccccccggcg    600
ggagccggtc cctttcccgt cggggagcgc ggggccgggg cccaggggac cccgggccac    660
ggagagcggg aagaggatgg attgcccggc cctccccccc ggatggaaga aggaggaagt    720
gatccgaaaa tctgggctaa gtgctggcaa gagcgatgtc tactacttca gtccaagtgg    780
taagaagttc agaagcaagc ctcagttggc aaggtacctg gaaatactg ttgatctcag    840 cagttttgac ttcagaactg gaaagatgat gcctagtaaa ttacgaaga acaaacagag    900 actgcgaaac gatcctctca atcaaaataa gggtaaacca gacttgaata caacattgcc    960
aattagacaa acagcatcaa ttttcaaaca accggtaacc aaagtcacaa atcatcctag   1020
taataaagtg aaatcagacc acaacgaatt gaatgaacag ccacgtcagc ttttctggga   1080
gaagaggcta caaggactta gtgcatcaga tgtaacagaa caaattataa aaaccatgga   1140
actacccaaa ggtcttcaag gagttggtcc aggtagcaat gatgagaccc ttttatctgc   1200
tgttgccagt gctttgcaca caagctctgc gccaatcaca gggcaagtct ccgctgctgt   1260
ggaaaagaac cctgctgttt ggcttaacac atctcaaccc ctctgcaaag cttttattgt   1320
cacagatgaa gacatcagga aacaggaaga gcgagtacga caagtacgca agaaattgga   1380
agaagcactg atggcagaca tcttgtcgcg agctgctgat acagaagaga tggatattga   1440
aatggacagt ggagatgaag cctaagaata tgatcaggta actttcgacc gactttcccc   1500
aagrgaaaat tcctagaaat tgaacaaaaa tgttccact ggcttttgcc tgtaagaaaa   1560
aaaatgtacc cgagcacata gagcttttta atagcactaa ccaatgcctt tttagatgta   1620
tttttgatgt atatatctat tattcaaaaa atcatgttta ttttgagtcc taggacttaa   1680
aattagtctt ttgtaatatc aagcaggacc ctaagatgaa gctgagcttt tgatgccagg   1740
tgcaatctac tggaaatgta gcacttacgt aaaacatttg ttccccccac agttttaata   1800
agaacagatc aggaattcta aataaatttc ccagttaaag attattgtga cttcactgta   1860
tataaacata tttttatact ttattgaaag gggacacctg tacattcttc catcatcact   1920
gtaaagacaa ataaatgatt atattcacaa aaaaaaaaaa aaaaaa                 1966
```

<210> SEQ ID NO 6
<211> LENGTH: 414
<212> TYPE: PRT
<213> ORGANISM: Unknown
<220> FEATURE:
<223> OTHER INFORMATION: predicted amino acid sequence of mouse dMTase1

<400> SEQUENCE: 6

Met Arg Ala His Pro Gly Gly Arg Cys Cys Pro Glu Gln Glu Glu
 1               5                  10                  15

Gly Glu Ser Ala Ala Gly Gly Ser Gly Ala Gly Gly Asp Ser Ala Ile

```
                    20                  25                  30
Glu Gln Gly Gly Gln Gly Ser Ala Leu Ala Pro Ser Pro Val Ser Gly
                35                  40                  45

Val Arg Arg Glu Gly Ala Arg Gly Gly Arg Gly Arg Gly Arg Trp
 50                  55                  60

Lys Gln Ala Ala Arg Gly Gly Val Cys Gly Arg Gly Arg Gly Arg
 65                  70                  75                  80

Gly Arg Gly Arg Gly Arg Gly Arg Gly Arg Gly Arg Gly Arg Gly Arg
                85                  90                  95

Pro Gln Ser Gly Gly Ser Gly Leu Gly Gly Asp Gly Gly Gly Ala
                100                 105                 110

Gly Gly Cys Gly Val Gly Ser Gly Gly Val Ala Pro Arg Arg Asp
                115                 120                 125

Pro Val Pro Phe Pro Ser Gly Ser Ser Gly Pro Gly Pro Arg Gly Pro
    130                 135                 140

Arg Ala Thr Glu Ser Gly Lys Arg Met Asp Cys Pro Ala Leu Pro Pro
145                 150                 155                 160

Gly Trp Lys Lys Glu Glu Val Ile Arg Lys Ser Gly Leu Ser Ala Gly
                165                 170                 175

Lys Ser Asp Val Tyr Tyr Phe Ser Pro Ser Gly Lys Lys Phe Arg Ser
                180                 185                 190

Lys Pro Gln Leu Ala Arg Tyr Leu Gly Asn Ala Val Asp Leu Ser Ser
                195                 200                 205

Phe Asp Phe Arg Thr Gly Lys Met Met Pro Ser Lys Leu Gln Lys Asn
    210                 215                 220

Lys Gln Arg Leu Arg Asn Asp Pro Leu Asn Gln Asn Lys Gly Lys Pro
225                 230                 235                 240

Asp Leu Asn Thr Thr Leu Pro Ile Arg Gln Thr Ala Ser Ile Phe Lys
                245                 250                 255

Gln Pro Val Thr Lys Phe Thr Asn His Pro Ser Asn Lys Val Lys Ser
                260                 265                 270

Asp Pro Gln Arg Met Asn Glu Gln Pro Arg Gln Leu Phe Trp Glu Lys
                275                 280                 285

Arg Leu Gln Gly Leu Ser Ala Ser Asp Val Thr Glu Gln Ile Ile Lys
    290                 295                 300

Thr Met Glu Leu Pro Lys Gly Leu Gln Gly Val Gly Pro Gly Ser Asn
305                 310                 315                 320

Asp Glu Thr Leu Leu Ser Ala Val Ala Ser Leu His Thr Ser Ser
                325                 330                 335

Ala Pro Ile Thr Gly Gln Val Ser Ala Val Glu Lys Asn Pro Ala
                340                 345                 350

Val Trp Leu Asn Thr Ser Gln Pro Leu Cys Lys Ala Phe Ile Val Thr
                355                 360                 365

Asp Glu Asp Ile Arg Lys Gln Glu Arg Val Gln Gln Val Arg Lys
    370                 375                 380

Lys Leu Glu Glu Ala Leu Met Ala Asp Ile Leu Ser Arg Ala Ala Asp
385                 390                 395                 400

Thr Glu Glu Val Asp Ile Asp Met Asp Ser Gly Asp Glu Ala
                    405                 410

<210> SEQ ID NO 7
<211> LENGTH: 2392
<212> TYPE: DNA
<213> ORGANISM: Unknown
```

<220> FEATURE:
<223> OTHER INFORMATION: cDNA sequence of mouse dMTase2

<400> SEQUENCE: 7

| | | | | | |
|---|---|---|---|---|---|
| agcgggccga | ggagccgggc | gcaatggagc | ggaagaggtg | ggagtgcccg | gcgctcccgc | 60 |
| agggctggga | gagggaagaa | gtgcccagaa | ggtcgggggct | gtcggccggc | cacagggatg | 120 |
| tcttttacta | tagcccgagc | gggaagaagt | tccgcagcaa | gccgcagctg | gcgcgctacc | 180 |
| tgggcggctc | catggacctg | agcaccttcg | acttccgcac | gggcaagatg | ctgatgagca | 240 |
| agatgaacaa | gagccgccag | cgcgtgcgct | acgactcctc | caaccaggtc | aagggcaagc | 300 |
| ccgacctgaa | cacggcgctg | cccgtgcgcc | agacggcgtc | catcttcaag | cagccggtga | 360 |
| ccaagattac | caaccacccc | agcaacaagg | tcaagagcga | cccgcagaag | gcggtggacc | 420 |
| agccgcgcca | gctcttctgg | gagaagaagc | tgagcggcct | gaacgccttc | gacattgctg | 480 |
| aggagctggt | caagaccatg | gacctcccca | agggcctgca | gggggtggga | cctggctgca | 540 |
| cggatgagac | gctgctgtcg | gccatcgcca | gcgccctgca | cactagcacc | atgcccatca | 600 |
| cgggacagct | ctcggccgcc | gtggagaaga | accccggcgt | atggctcaac | accacgcagc | 660 |
| ccctgtgcaa | agccttcatg | gtgaccgacg | aggacatcag | gaagcaggaa | gagctggtgc | 720 |
| agcaggtgcg | gaagcggctg | gaggaggcgc | tgatggccga | catgctggcg | cacgtggagg | 780 |
| agctggcccg | tgacggggag | gcgccgctgg | acaaggcctg | cgctgaggac | gacgacgagg | 840 |
| aagacgagga | ggaggaggag | gaggagcccg | accggacccc | ggagatggag | cacgtctagg | 900 |
| gcagaggccc | tgccgagagc | ccgtgctgcc | tgctggagcc | gcctgcagac | gcggtcctcg | 960 |
| gccccacgtg | aaccaggctc | ggcggcgaag | cccagccttg | gagacaccca | ggaggaaggc | 1020 |
| cgtgctcctg | gctccctcct | cggcccgtcc | ccacttcccg | gggcctcggg | gcacacagct | 1080 |
| ggggctgccc | ccacccgaaa | gaccctccac | gctcgtcctc | tacagagtcc | ggcttcggga | 1140 |
| agtgccgggt | gctcctgggc | cctgcctggc | tccctacgac | ctttgggctc | gaggccagct | 1200 |
| cctcccatg | cccgctgtcc | cagctccttg | agactggaga | gcagccagca | ggtgcccggc | 1260 |
| agctcggcgc | cacggcttgc | tgacagctgg | gagggtttct | cggtctggag | gcgtagtttt | 1320 |
| gaaactcaca | tcacccactg | tgcagcgtga | ggacgggact | ctggtctgct | gtgggggca | 1380 |
| tgcaggacgg | cgccactctc | tgccctgcca | tgcggctggt | ggtgccacag | agcctcaccg | 1440 |
| tgcctgagtg | gcgtgcccag | ggaggccgct | ctccttcagt | aaatgtaaca | cagtcgaggc | 1500 |
| acgtcatcgg | gcagccttcc | ctgtgtgcca | acgccagcct | tcgcttctga | aaaccaaact | 1560 |
| ccagccgctg | ccagtcggga | cttggtcgcc | cggcgctgcc | agaatgctcc | actgccagcc | 1620 |
| ggccccctg | cctcggtttc | ccttctgttt | agtggcgaca | caggcaccca | gctttgggt | 1680 |
| ggtgctgacg | ctcccagggg | tgccaggagc | cactgggaca | gggtgaggct | cccagacgct | 1740 |
| cctcgaggtg | cccagctctc | cagggagctt | ctggcccaag | gcgttcttga | gggatctgct | 1800 |
| ccttaacccc | ccagtgcctt | ggcgagggca | ggttccaagc | cacagacgcc | tgccccgagt | 1860 |
| ggactttgcg | gccagtccct | gggtgccttc | ctgggcctg | cttgcccagt | gagggttcct | 1920 |
| aacgggtggg | ttcawtggcc | tggcccvagc | gagcccccac | ctgcattgac | cttaggccca | 1980 |
| tagagagggc | ctgtcccggt | gctgcccag | ccaaggatct | ggtcgctgcc | caggggggac | 2040 |
| tgatgggcaa | gagtcgcccc | tgtggctgga | ctgtgaccat | ccctgatggg | gcctgaccgc | 2100 |
| gggagctgag | gaagcgccgc | tccaccgtct | gccctccaag | gacccgcatg | gaggcagtgg | 2160 |
| gctggcagct | tcctgctgct | ccctgtcaga | gtcaaagcac | aaatcctcag | gacgggctca | 2220 |

```
agggccaggg cagccgaggg aagctccagg tggggaccac gtcttcctga ggttggtgcc    2280
cactggctgg gaccctttgc agtggggtgg cctcccctct gtctgcctgg tgagggagc    2340 cgtgggcgtg gggacgtgac tgaataaagc caccatgggt ggatgtgctt gg           2392
```

<210> SEQ ID NO 8
<211> LENGTH: 285
<212> TYPE: PRT
<213> ORGANISM: Unknown
<220> FEATURE:
<223> OTHER INFORMATION: predicted amino acid sequence of mouse dMTase2

<400> SEQUENCE: 8

```
Met Glu Arg Lys Arg Trp Glu Cys Pro Ala Leu Pro Gln Gly Trp Glu
 1               5                  10                  15

Arg Glu Glu Val Pro Arg Ser Gly Leu Ser Ala Gly His Arg Asp
                20                  25                  30

Val Phe Tyr Tyr Ser Pro Ser Gly Lys Lys Phe Arg Ser Lys Pro Gln
             35                  40                  45

Leu Ala Arg Tyr Leu Gly Gly Ser Met Asp Leu Ser Thr Phe Asp Phe
         50                  55                  60

Arg Thr Gly Lys Met Leu Met Asn Lys Met Asn Lys Ser Arg Gln Arg
65                  70                  75                  80

Val Arg Tyr Asp Ser Ser Asn Gln Val Lys Gly Lys Pro Asp Leu Asn
                 85                  90                  95

Thr Ala Leu Pro Val Arg Gln Thr Ala Ser Ile Phe Lys Gln Pro Val
            100                 105                 110

Thr Lys Ile Thr Asn His Pro Ser Asn Lys Val Lys Ser Asp Pro Gln
         115                 120                 125

Lys Ala Val Asp Gln Pro Arg Gln Leu Phe Trp Glu Lys Lys Leu Ser
    130                 135                 140

Gly Leu Ser Ala Phe Asp Ile Ala Glu Glu Leu Val Arg Thr Met Asp
145                 150                 155                 160

Leu Pro Lys Gly Leu Gln Gly Val Gly Pro Gly Cys Thr Asp Glu Thr
                165                 170                 175

Leu Leu Ser Ala Ile Ala Ser Ala Leu His Thr Ser Thr Leu Pro Ile
            180                 185                 190

Thr Gly Gln Leu Ser Ala Ala Val Glu Lys Asn Pro Gly Val Trp Leu
        195                 200                 205

Asn Thr Ala Gln Pro Leu Cys Lys Ala Phe Met Val Thr Asp Asp
    210                 215                 220

Ile Arg Lys Gln Glu Glu Leu Val Gln Val Arg Lys Arg Leu Glu
225                 230                 235                 240

Glu Ala Leu Met Ala Asp Met Leu Ala His Val Glu Glu Leu Ala Arg
                245                 250                 255

Asp Gly Glu Ala Pro Leu Asp Lys Ala Cys Ala Glu Glu Glu Glu
            260                 265                 270

Glu Glu Glu Glu Glu Glu Glu Pro Glu Pro Glu Arg Val
        275                 280                 285
```

<210> SEQ ID NO 9
<211> LENGTH: 17
<212> TYPE: DNA
<213> ORGANISM: Unknown
<220> FEATURE:
<223> OTHER INFORMATION: sense primer for amplification of MBD domain
      of the putative demethylase candidate cDNA

```
<400> SEQUENCE: 9
ctggcaagag cgatgtc                                                      17

<210> SEQ ID NO 10
<211> LENGTH: 22
<212> TYPE: DNA
<213> ORGANISM: Unknown
<220> FEATURE:
<223> OTHER INFORMATION: antisense primer for amplification of MBD
      domain of the putative demethylase candidate cDNA

<400> SEQUENCE: 10
agtctggttt acccttattt tg                                                22
```